(12) United States Patent
Holinski et al.

(10) Patent No.: US 10,799,706 B2
(45) Date of Patent: Oct. 13, 2020

(54) GARMENT FOR POSITIONING MIDFIELD TRANSMITTER RELATIVE TO IMPLANTED RECEIVER

(71) Applicant: NeuSpera Medical Inc., San Jose, CA (US)

(72) Inventors: Brad Holinski, Newark, CA (US); Alexander Yeh, Los Altos Hills, CA (US); Elia Junco, Palo Alto, CA (US); Timothy Edward Ciciarelli, San Jose, CA (US)

(73) Assignee: NEUSPERA MEDICAL INC., San Jose, CA (US)

( * ) Notice: Subject to any disclaimer, the term of this patent is extended or adjusted under 35 U.S.C. 154(b) by 0 days.

(21) Appl. No.: 16/123,230

(22) Filed: Sep. 6, 2018

(65) Prior Publication Data
US 2020/0078596 A1    Mar. 12, 2020

(51) Int. Cl.
*A61N 1/32* (2006.01)
*A61N 1/372* (2006.01)
(Continued)

(52) U.S. Cl.
CPC ......... *A61N 1/37229* (2013.01); *A61N 1/321* (2013.01); *H02J 50/20* (2016.02);
(Continued)

(58) Field of Classification Search
CPC .................................. A61N 1/372; A61N 1/32
See application file for complete search history.

(56) References Cited

U.S. PATENT DOCUMENTS 7,054,689 B1  5/2006  Whitehurst et al.
8,466,375 B2  6/2013  Cho et al.
(Continued)

FOREIGN PATENT DOCUMENTS

WO    2014187605    11/2014
WO    WO-2017070372 A1    4/2017

OTHER PUBLICATIONS

"International Application Serial No. PCT US2019 049772, International Search Report dated Nov. 8, 2019", 2 pages.
(Continued)

*Primary Examiner* — Carl H Layno
*Assistant Examiner* — Jennifer L Ghand
(74) *Attorney, Agent, or Firm* — Schwegman Lundberg & Woessner, P.A.

(57) ABSTRACT

Systems, devices and methods to facilitate wireless interaction between an implantable therapy delivery device and an external transmitter device are provided. In an example, the systems, devices, and methods discussed herein include or use a garment for receiving and positioning an external transmitter device proximal to an implanted device, and the external transmitter device includes a midfield device configured to provide one or more signals to manipulate evanescent fields outside of tissue to generate a propagating and focused field in the tissue. In an example, the garment includes a receptacle configured to receive and retain the external transmitter device near a tissue interface, and the garment further includes a dielectric portion provided between the receptacle and the tissue interface. In an example, the dielectric portion has a relative permittivity that is approximately the same as the relative permittivity of air.

20 Claims, 30 Drawing Sheets

(51) Int. Cl.
*H02J 50/20* (2016.01)
*H02J 50/10* (2016.01)
*H02J 7/02* (2016.01)
*H02J 50/40* (2016.01)
*H02J 50/80* (2016.01)
*A61B 5/00* (2006.01)

(52) U.S. Cl.
CPC ......... *A61B 5/6804* (2013.01); *A61N 1/37252* (2013.01); *H02J 7/025* (2013.01); *H02J 50/10* (2016.02); *H02J 50/40* (2016.02); *H02J 50/80* (2016.02)

(56) References Cited

U.S. PATENT DOCUMENTS

| | | |
|---|---|---|
| 9,351,790 B2 | 5/2016 | Zemel et al. |
| 9,564,777 B2 | 2/2017 | Yeh et al. |
| 10,010,714 B2 | 7/2018 | Coleman et al. |
| 2011/0282416 A1 | 11/2011 | Hamann et al. |
| 2014/0180365 A1 | 6/2014 | Perryman et al. |
| 2015/0041540 A1* | 2/2015 | Qu ..................... H01Q 1/2225 235/439 |
| 2016/0344238 A1* | 11/2016 | Yeh ................... A61N 1/37229 |
| 2018/0085593 A1 | 3/2018 | Fayram et al. |

OTHER PUBLICATIONS

"International Application Serial No. PCT US2019 049772, Written Opinion dated Nov. 8, 2019", 14 pages.

* cited by examiner

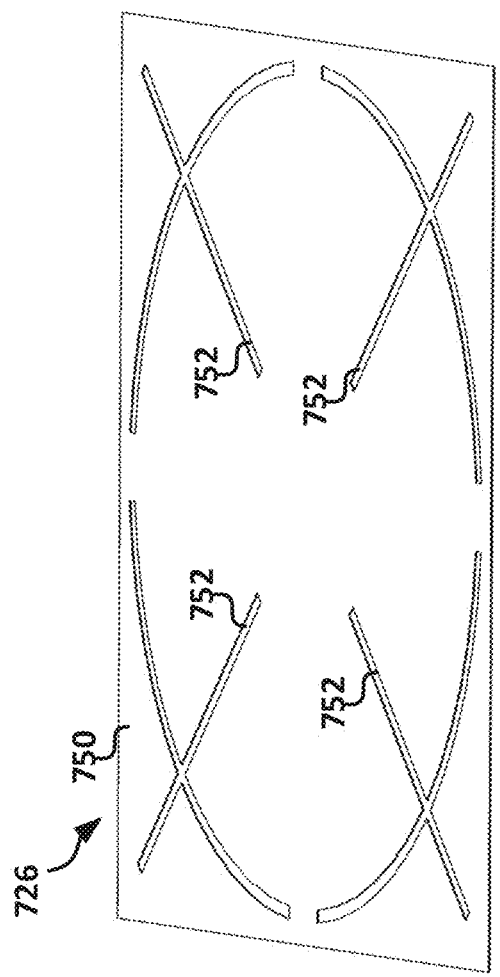
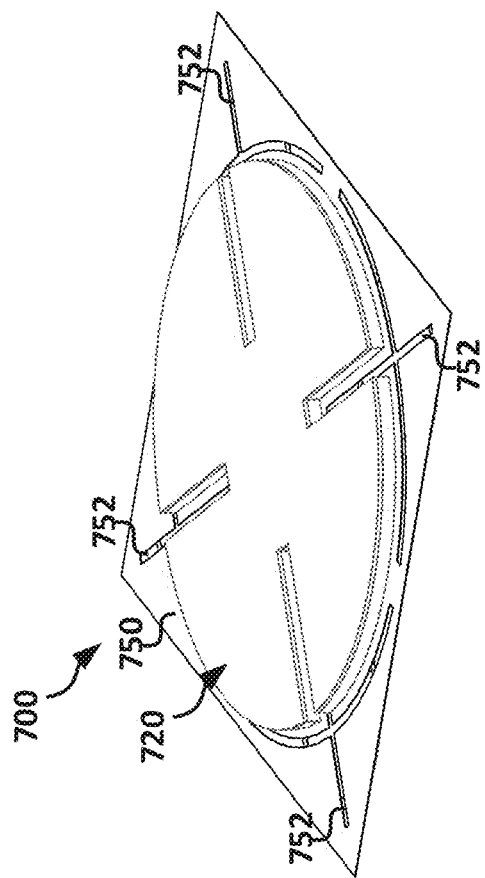

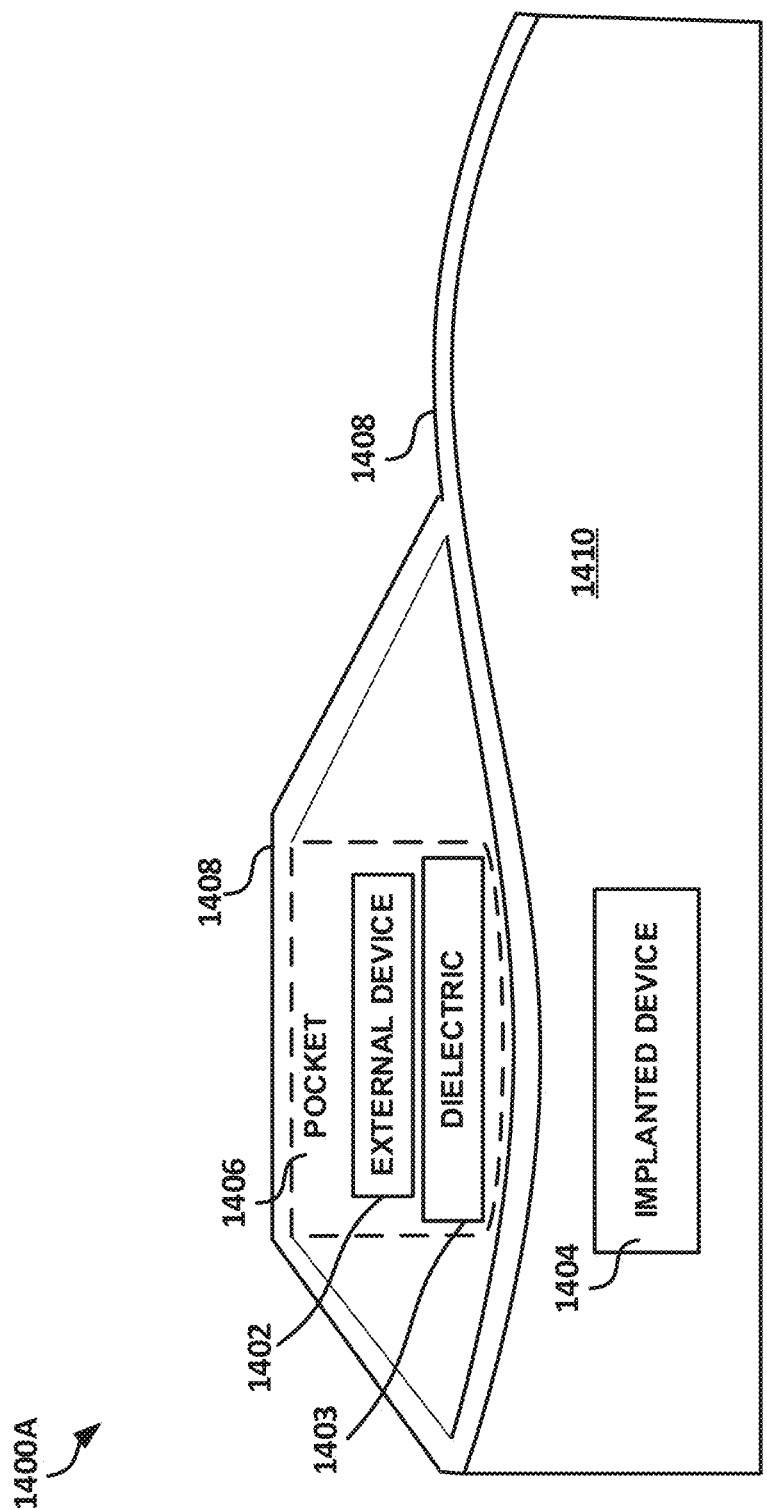

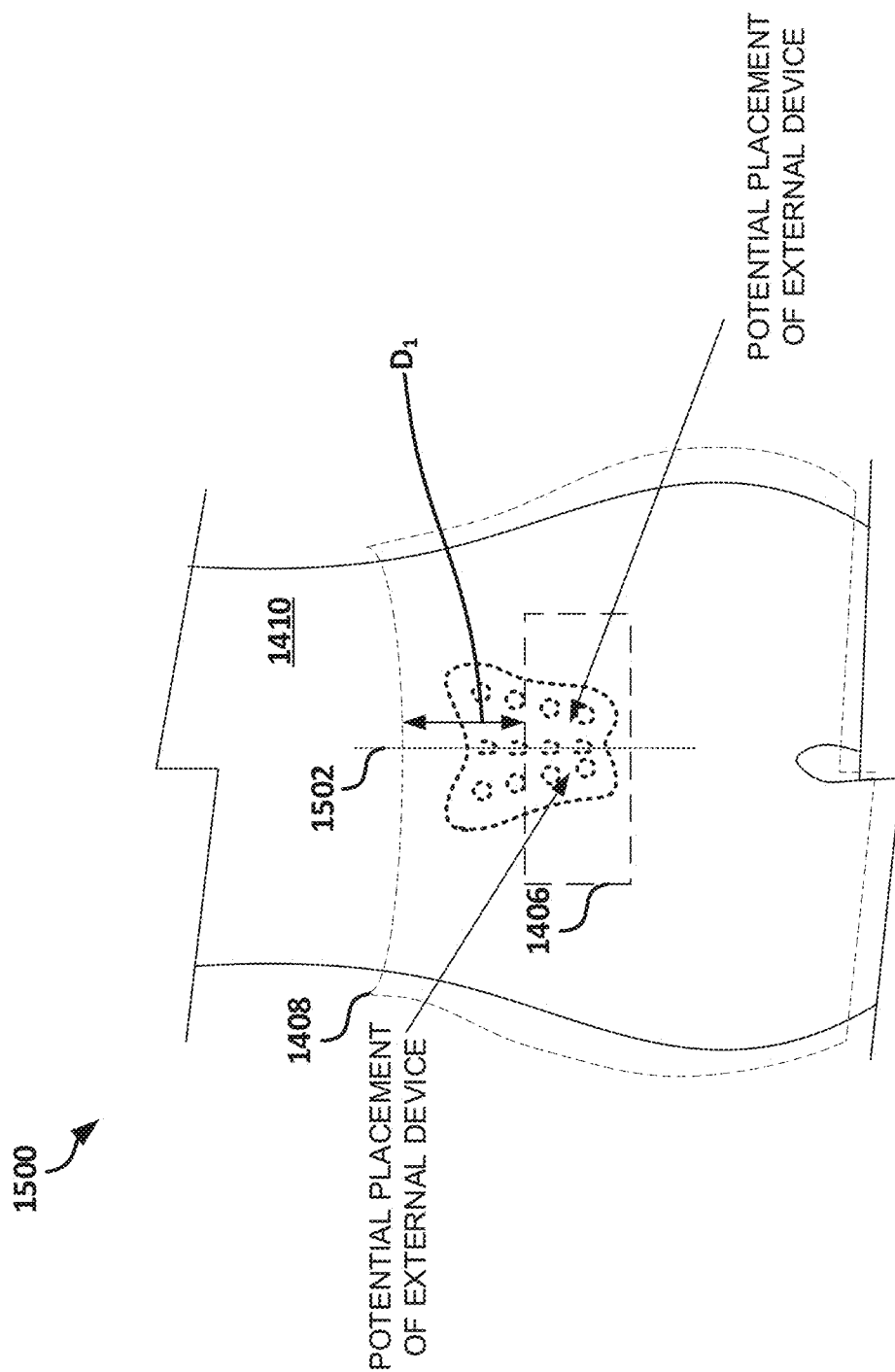

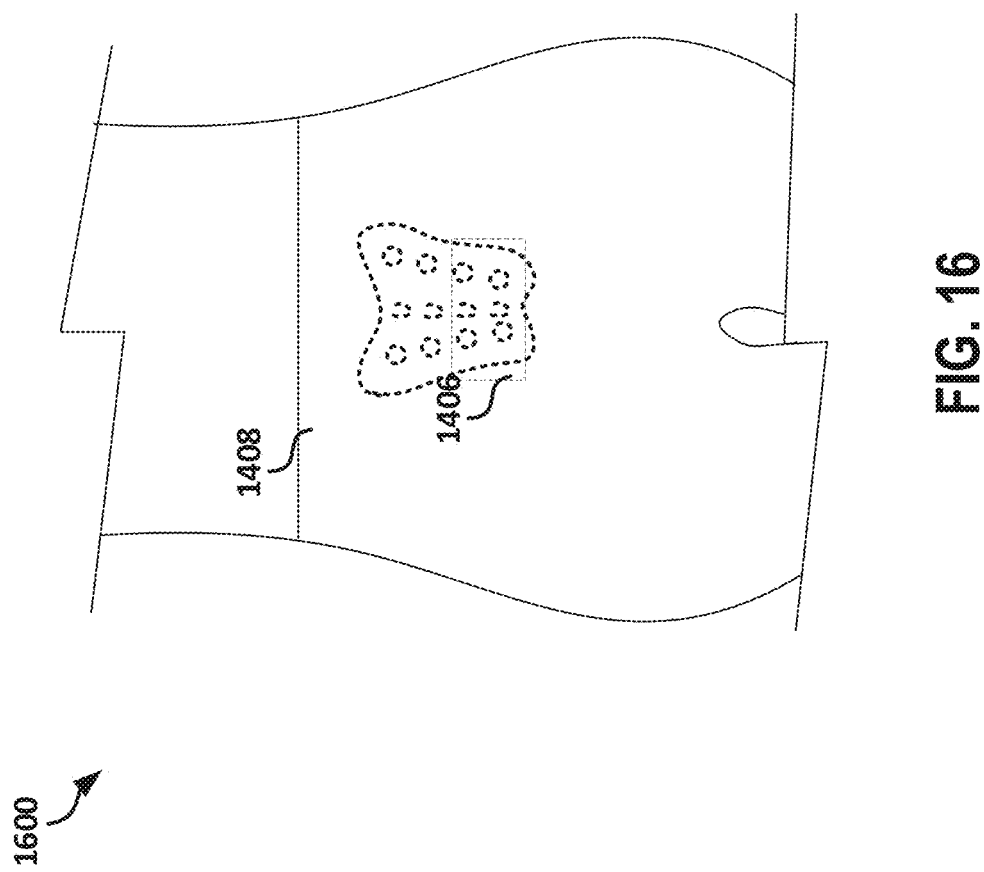

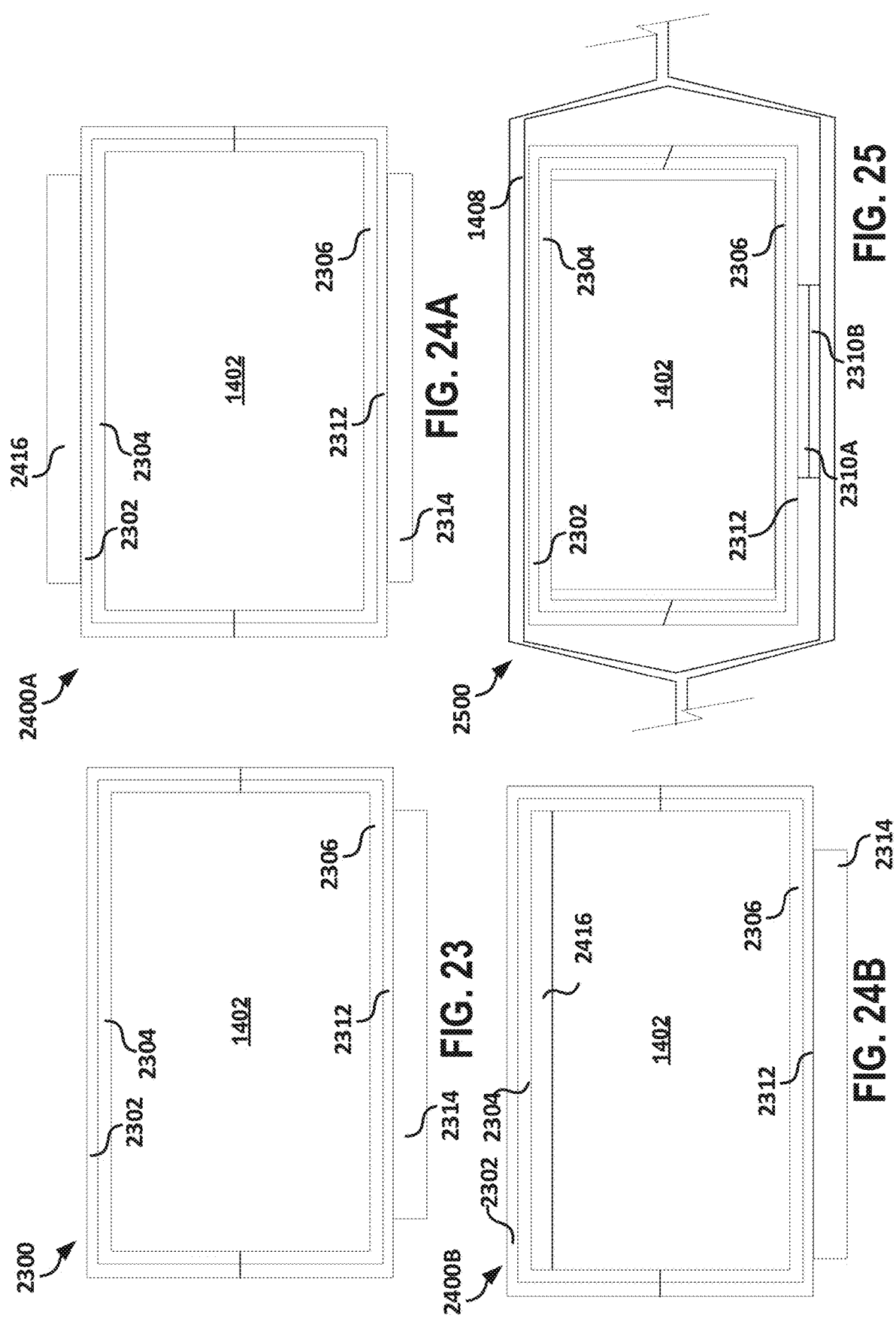

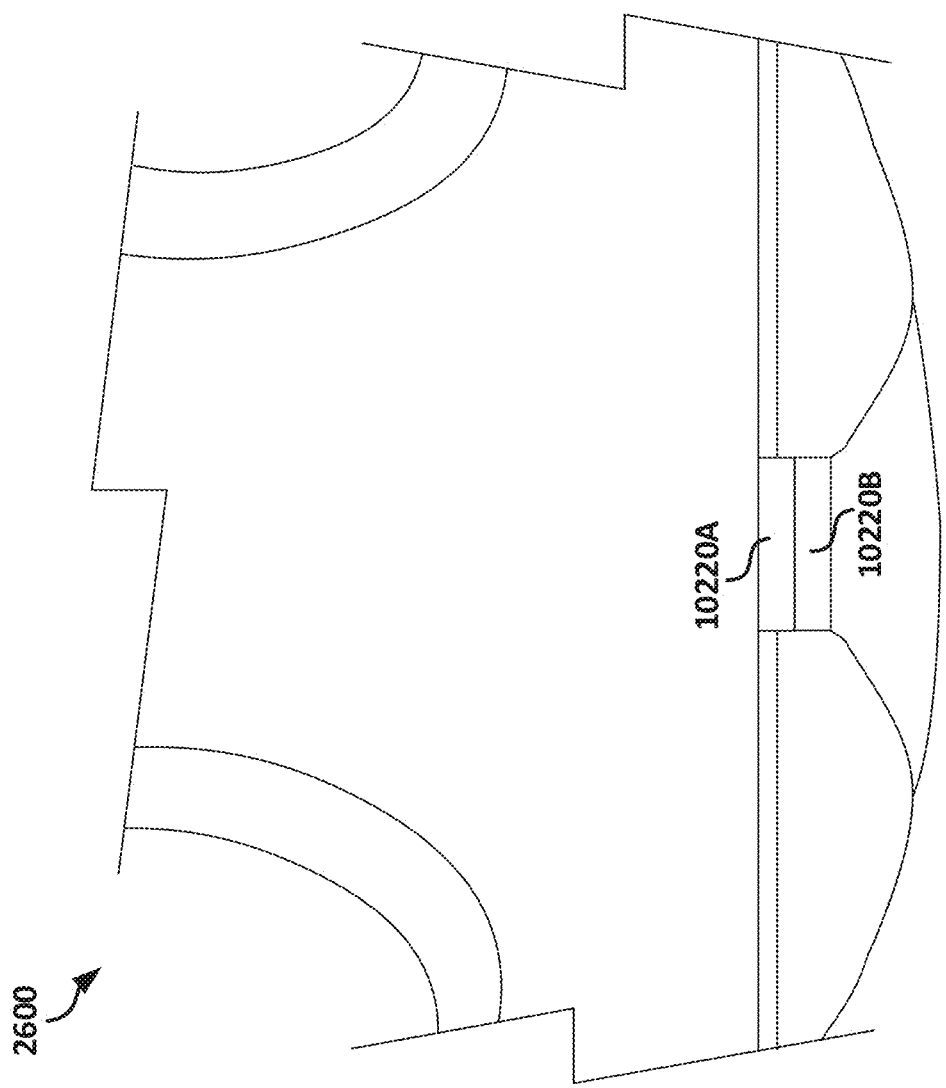

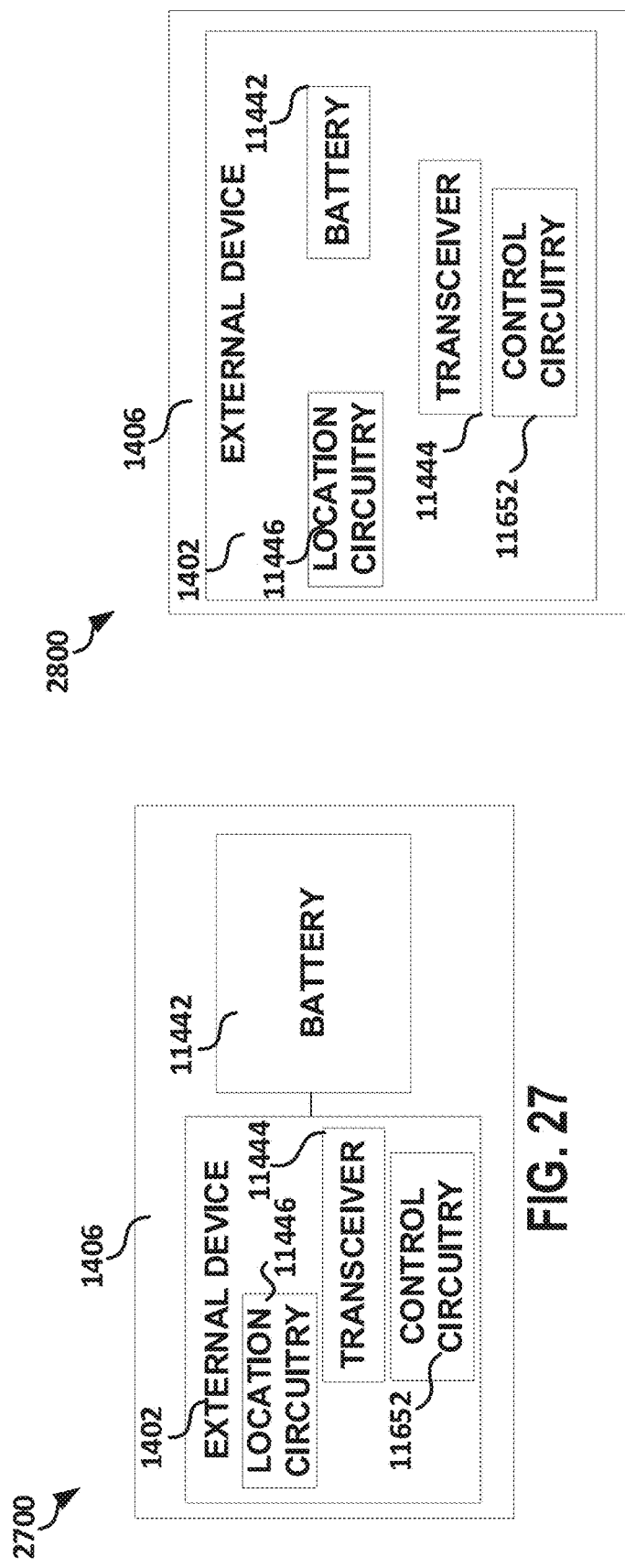
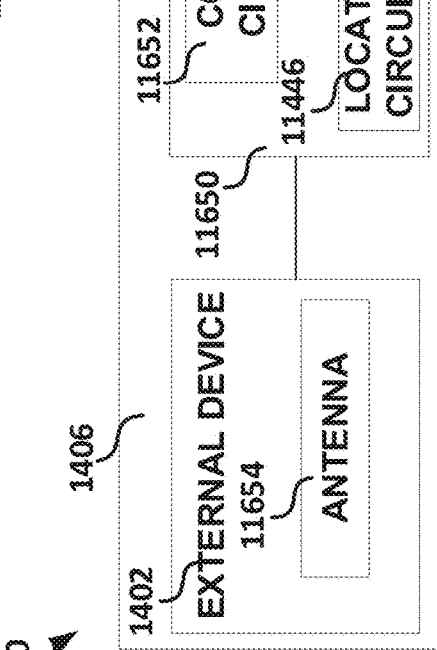
FIG. 27
FIG. 28
FIG. 29

GARMENT FOR POSITIONING MIDFIELD TRANSMITTER RELATIVE TO IMPLANTED RECEIVER

BACKGROUND

Various wireless powering methods for implantable electronics are based on nearfield coupling. These and other suggested methods suffer from a number of disadvantages. For example, a power harvesting structure in the implanted device is typically large, such as on the order of a centimeter or more. Transmission coils provided external to the body in nearfield arrangements are also often bulky and inflexible. Among other factors, these can present challenges or difficulties with regard to incorporation of the external device into daily life. Furthermore, the intrinsic exponential decay of nearfield transmission limits miniaturization of the implanted device and limits implantation to superficial depths (e.g., around 1 cm or less below a tissue interface). Some wireless powering methods are based on farfield coupling. However, the radiative nature of farfield coupling limits energy transfer efficiency.

SUMMARY

Although considerable progress has been made in the realm of medical device therapy, a need exists for therapy devices that provide stimulation or other therapy to targeted locations within a body. A need further exists for efficient, wireless power and data communication with an implanted therapy delivery device and/or an implanted diagnostic (e.g., sensor) device. A need further exists for user-friendly, repeatable, and accurate placement of an external transmitter device relative to an implanted device.

In accordance with several embodiments, a garment can be provided for receiving and positioning an external transmitter device proximal to an implanted device, the external transmitter device including a midfield device configured to provide one or more signals to manipulate evanescent fields outside of tissue to generate a propagating and focused field in the tissue. In accordance with an embodiment, the garment includes a first receptacle (pocket, coupling, receiving member, etc.) configured to receive and retain the external transmitter device near a tissue interface, wherein the external transmitter device is configured to provide an electromagnetic midfield signal to the implanted device. The garment can further include or use a dielectric portion provided between the first receptacle and the tissue interface, wherein the dielectric portion has a relative permittivity that is approximately the same as the relative permittivity of air.

In accordance with several embodiments, a system can be provided for use with an implanted midfield receiver device, the system comprising an external midfield transmitter device with one or more structures excitable by a voltage or current source to manipulate evanescent fields outside of tissue to generate a propagating and focused field in the tissue and thereby communicate power and/or data signals from the external midfield transmitter device to the implanted midfield receiver device. In accordance with an embodiment, the garment can include a receptacle configured to receive the external midfield transmitter device and position it near a tissue interface, and the garment can include a dielectric portion provided between the receptacle and the tissue interface.

In accordance with several embodiments, a method can be provided for controlling delivery of neural stimulation therapy using a system that includes an implanted midfield device and external midfield transmitter device, wherein the external midfield transmitter device includes one or more structures excitable to manipulate evanescent fields outside of tissue to generate a propagating and focused field in the tissue and thereby communicate power and/or data signals to the implanted midfield device. In an example, the implanted midfield device includes one or more electrodes for delivering an electrostimulation therapy to a neural target, or for sensing physiologic information from a patient (or user), and the delivered therapy can use energy received from the external midfield transmitter device. In an example, the method can include positioning the external midfield transmitter device at or near a tissue interface and the implanted midfield device using a garment. In an example, the method includes using energy received from the external midfield transmitter device to provide a stimulation therapy at or near a neural target in a pelvic region of a patient using the implanted midfield device. In an example, the method further includes determining, using a control circuit, whether a voiding event is, or is likely to be, imminent or occurring for the patient, and enhancing voiding efficiency for the patient, including inhibiting or ceasing the stimulation therapy provided to the neural target when the voiding event is determined to be, or is determined to be likely to be, imminent or occurring for the patient. In an example, the stimulation therapy can be inhibited or ceased when the garment, and therefore the external transmitter, is removed from its regular or intended position when it is worn by the patient.

In accordance with several embodiments, a system for covering or holding an external device comprises a portion of a garment or wearable accessory that includes a receptacle, such as one of a pocket and a sleeve comprising one or more top or outer layers of compliant material and one or more bottom or inner layers of compliant material. The bottom layers of material are closer to a body surface or tissue interface of a user (or patient) than the top layers when the garment is worn by the user. In an example, the bottom layers comprise one or more features or through-holes configured to provide electrical contact between electrodes on the external device and a tissue surface of a user.

The bottom layers can include a first layer of fabric that is a soft, compliant material and a second layer of fabric that is one of a heat insulating material and/or a water resistant material. The second layer of fabric is located further from the body of the user when the garment is worn. The top layer can include a third layer of fabric that comprises a heat conducting material. In an example, the system comprises an external transmitter device (e.g., any of the external devices or midfield couplers described herein) that is located at least partially in the receptacle between the layers. The external device is configured to provide electromagnetic energy to an implanted device.

In an example, one or more top layers can include a fourth layer of fabric further from the body of the user than the third layer when the garment is won, the fourth layer comprising an elastic band. The elastic band can include a plurality of holes in at least a portion of the band. In some embodiments, the holes are advantageously taller than they are wide. However, the holes may have substantially the same height and width in other embodiments or the holes may be wider than they are tall.

In some embodiments, the system comprises a garment or article of clothing that includes the receptacle, wherein the receptacle is situated at a location above or near a target tissue location (e.g., an S3 foramen) of the body when the garment is worn by the user. The external stimulator device may comprise location circuitry configured to communicate with an implanted device and provide an indication of whether the external transmitter device is properly located relative to the implanted device.

In some embodiments, the external transmitter device comprises a first attachment mechanism and the pocket or sleeve comprises a corresponding second attachment mechanism. The attachment mechanisms may be located such that when the attachment mechanisms are mated the external stimulator device is properly located relative to (e.g., proximate or near) a target implanted device.

This Summary is intended to provide an overview of subject matter of the present application. It is not intended to provide an exclusive or exhaustive explanation of the invention or inventions discussed herein. The detailed description is included to provide further information about the present patent application

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 11 illustrates, by way of example, a perspective view diagram of an embodiment of a top layer of the board of FIG. 8.

FIG. 12 illustrates, by way of example, a perspective view diagram of an embodiment of the top layer of the board of FIG. 8 with a faraday cage situated thereon.

FIG. 14A illustrates, by way of example, a block diagram of an embodiment of a system for locating an external source device relative to an implanted device.

FIG. 15 illustrates, by way of example, a diagram of a portion of a human body with a view of a lower rear portion of a skeletal system.

FIG. 16 illustrates, by way of example, a perspective view diagram similar to that of FIG. 15 with a garment receptacle positioned over potential implant sites of a neurostimulator.

FIG. 23 illustrates, by way of example, a cross-section view diagram of an embodiment of a system 2300 that includes the external device 1402 situated in a sleeve FIG. 24A illustrates, by way of example, a perspective view diagram of an embodiment of a system including a cushion material.

FIG. 24B illustrates, by way of example, a perspective view diagram of an embodiment of a system including a cushion material.

FIG. 25 illustrates, by way of example, a cross-section view diagram of an embodiment of a system including a sleeve with an external device situated therein.

FIG. 26 illustrates, by way of example, a perspective view diagram of an embodiment of an undergarment that includes a fastener.

FIG. 27 illustrates, by way of example, a block diagram of an embodiment of a system that includes multiple discrete external components.

FIG. 28 illustrates, by way of example, a block diagram of an embodiment of a system that includes a single external device in a wearable receptacle.

FIG. 29 illustrates, by way of example, a block diagram of an embodiment of a system that includes multiple discrete external devices in a wearable receptacle.

DESCRIPTION OF EMBODIMENTS

Figure 1:
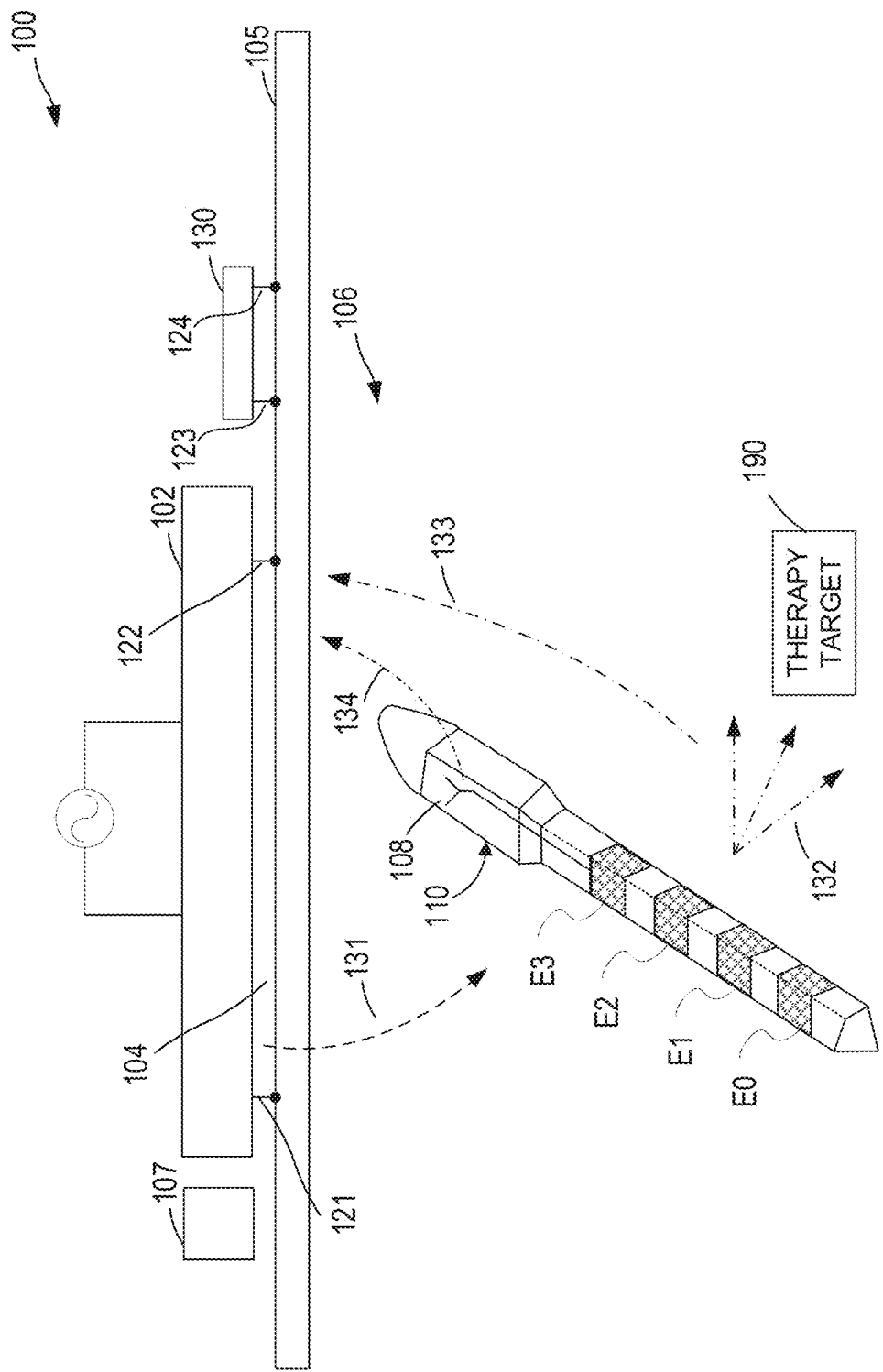
FIG. 1 illustrates, by way of example, a schematic of an embodiment of a system using wireless communication paths.

Midfield powering technology can provide power to a deeply implanted electrostimulation device from an external transmitter device or power source located on or near a tissue surface, such as at an external surface of a user's skin. The user can be a clinical patient or other user. The midfield powering technology can have one or more advantages over implantable pulse generators. For example, a pulse generator can have one or more relatively large, implanted batteries and/or one or more lead systems. Implantable midfield receiver devices, in contrast, can include relatively small battery cells that can be configured to receive and store relatively small amounts of power. A midfield device can include one or more electrodes integrated in a unitary implantable package. Thus, in some examples, a midfield-powered device can provide a simpler implant procedure over other conventional devices, which can lead to a lower cost and a lower risk of infection or other implant complications. One or more of the advantages can include an amount of power transferred to the implanted device. The ability to focus the energy from the external transmitter device can allow for an increase in an amount of power transferred to an implanted device.

An advantage of using midfield powering technology can include a main battery or power source being provided externally to the patient, and thus low power consumption and high efficiency circuitry requirements of conventional battery-powered implantable devices can be relaxed. Another advantage of using midfield powering technology can include an implanted device that can be physically smaller than a battery-powered device. Midfield powering technology can thus help enable better patient tolerance and comfort along with potentially lower costs to manufacture and/or to implant in patient tissue.

There is a current unmet need that includes accurately, repeatably, and chronically positioning an external midfield transmitter device relative to the body in a manner that is comfortable and feasible for patients or device users. The unmet need can include accessories, devices, garments, and the like, that are configured to receive and retain a midfield transmitter in a location sufficiently near an implanted midfield receiver to wirelessly and efficiently transmit power or data to the receiver. There is a further unmet need that includes providing various therapies and automatically inhibiting delivery of such therapies during various specified bodily activities such as voiding (urinating or defecating).

In one or more embodiments, multiple midfield receiver devices can be implanted in patient tissue and can be configured to deliver a therapy and/or sense physiologic information about a patient and/or about the therapy. The multiple implanted devices can be configured to communicate with one or more external devices. In one or more embodiments, the one or more external devices are configured to provide power and/or data signals to the multiple implanted devices, such as concurrently or in a time-multiplexed (e.g., "round-robin") fashion. The provided power and/or data signals can be steered or directed by an external device to transfer the signals to an implant most efficiently. Although the present disclosure may refer to a power signal or data signal specifically, such references are to be generally understood as optionally including one or both of power and data signals.

Several embodiments described herein can be advantageous because they include one, several, or all of the following benefits: (i) a system configured to (a) communicate power and/or data signals from a midfield coupler or transmitter device to an implantable receiver device via midfield radiofrequency (RF) signals, (b) generate and provide a therapy signal via one or more electrodes coupled to the implantable device, the therapy signal optionally including an information component, and producing a signal incident to providing the therapy signal, (c) receive a signal, based on the therapy signal, using electrodes coupled to the midfield coupler or transmitter device, and (d) at the midfield coupler or transmitter device or another device, decode and react to the information component from the received signal; (ii) a dynamically configurable, active midfield transceiver that is configured to provide RF signals to modulate an evanescent field at a tissue surface and thereby generate a propagating field within tissue, such as to transmit power and/or data signals to an implanted target device; (iii) an implantable device including an antenna configured to receive a midfield power signal from the midfield transceiver and including a therapy delivery circuitry configured to provide signal pulses to electrostimulation electrodes using a portion of the received midfield power signal, wherein the signal pulses include therapy pulses and data pulses, and the data pulses can be interleaved with or embedded in the therapy pulses; (iv) an implantable device configured to encode information, in a therapy signal, about the device itself, such as including information about the device's operating status, or about a previously-provided, concurrent, or planned future therapy provided by the device; (v) a midfield transceiver including electrodes that are configured to sense electrical signals at a tissue surface; and/or (vi) adjustable wireless signal sources and receivers that are configured together to enable a communication loop or feedback loop.

In one or more embodiments, one or more of these benefits and others can be realized using a system for manipulating an evanescent field at or near an external tissue surface to transmit power and/or data wirelessly to one or more target devices implanted in the tissue. In one or more embodiments, one or more of these benefits can be realized using a device or devices implanted in a body or capable of being implanted in a body and as described herein. In one or more embodiments, one or more of these benefits can be realized using a midfield powering and/or communication device (e.g., a transmitter device and/or a receiver device or a transceiver device).

A system can include a signal generator system adapted to provide multiple different sets of signals (e.g., RF signals). Each set can include two or more separate signals in some embodiments. The system can also include a midfield transmitter including multiple excitation ports, the midfield transmitter coupled to the RF signal generator system, and the midfield transmitter being adapted to transmit the multiple different sets of RF signals at respective different times via the excitation ports. The excitation ports can be adapted to receive respective ones of the separate signals from each set of RF signals. Each of the transmitted sets of RF signals can include a non-negligible magnetic field (H-field) component that is substantially parallel to the external tissue surface. In one or more embodiments, each set of transmitted. RF signals is adapted or selected to differently manipulate an evanescent field at or near the tissue surface to transmit a power and/or data signal to one or more target devices implanted in the tissue via a midfield signal instead of via inductive near-field coupling or radiative far-field transmission.

In one or more embodiments, one or more of the above-mentioned benefits, among others, can he realized, at least in part, using an implantable therapy delivery device e.g., that is adapted to provide neural stimulation) that includes receiver circuitry including an antenna (e.g., an electric-field or magnetic field based antenna) configured to receive a midfield power signal from an external source device, such as when the receiver circuitry is implanted within tissue. The implantable therapy delivery device can include therapy delivery circuitry. The therapy delivery circuitry can be coupled to the receiver circuitry. The therapy delivery circuitry can be configured to provide signal pulses to one or more energy delivery members (e.g., electrostimulation electrodes), which may be integrally coupled to a body of the therapy delivery device or positioned separately from (e.g., not located on) the body of the therapy delivery device), such as by using a portion of the received midfield power signal from the external source device (e.g., sometimes referred to herein as an external device, an external source, an external midfield device, a midfield transmitter device, a midfield coupler, a midfield powering device, a powering device, or the like, depending on the configuration and/or usage context of the device). The signal pulses can include one or more electrostimulation therapy pulses and/or data pulses. In one or more embodiments, one or more of the above-mentioned benefits, among others, can be realized, at least in part, using an external transmitter and/or receiver (e.g., transceiver) device that includes an electrode pair configured to be disposed at an external tissue surface, and the electrode pair is configured to receive an electrical signal via the tissue. The electrical signal can correspond to an electrostimulation therapy delivered to the tissue by the therapy delivery device. A demodulator circuitry can be coupled to the electrode pair and can be configured to demodulate a portion of the received electrical signal, such as to recover a data signal originated by the therapy delivery device.

In one or more embodiments that include using a midfield wireless transmitter device, tissue can act as a dielectric to tunnel energy. Coherent interference of propagating modes can confine a field at a focal plane to less than a corresponding vacuum wavelength, for example, with a spot size subject to a diffraction limit in a high-index material. In one or more embodiments, a receiver (e.g., implanted in tissue) positioned at such high energy density region, can be one or more orders of magnitude smaller than a conventional near-field implantable receiver, or can be implanted more deeply in tissue (e.g., greater than 1 cm in depth). In one or more embodiments, a transmitter source described herein can be configured to provide electromagnetic energy to various target locations, including for example to one or more deeply implanted devices. In an example, the energy can be provided to a location with greater than about a few millimeters of positioning accuracy. That is, a transmitted power or energy signal can be directed or focused to a target location that is within about one wavelength of the signal in tissue. Such energy focusing is substantially more accurate than the focusing available via traditional inductive means and is sufficient to provide adequate power to a receiver on a millimeter scale. In other wireless powering approaches using near-field coupling (inductive coupling and its resonant enhanced derivatives), evanescent components outside tissue (e.g., near the source) remain evanescent inside tissue, which does not allow for effective depth penetration. Unlike near-field coupling, energy from a midfield source is primarily carried in propagating modes and, as a result, an energy transport depth is limited by environmental losses rather than by intrinsic decay of the near-field. Energy transfer implemented with these characteristics can be at least two to three orders of magnitude more efficient than near-field systems.

One or more of the systems, apparatuses, and methods discussed herein can be used to help treat voiding dysfunctions such as fecal or urinary incontinence (e.g., overactive bladder), pudendal neuralgia, or other disorders such as by stimulating the tibial nerve or any branch of the tibial nerve, such as but not limited to the posterior tibial nerve, one or more nerves or nerve branches originating from the sacral plexus, including but not limited to S1-S4, the tibial nerve, and/or the pudendal nerve. Urinary incontinence may be treated by stimulating one or more of muscles of the pelvic floor, nerves innervating the muscles of the pelvic floor, internal urethral sphincter, external urethral sphincter, and the pudendal nerve or branches of the pudendal nerve. In an example, an external midfield transmitter device is configured to coordinate a chronic stimulation therapy provided by the implanted midfield receiver device to a target region at or near the pudendal nerve, the genitofemoral nerve, or the sciatic nerve. In an example, overactive bladder can be treated using the systems and methods discussed herein, such as by providing chronic pudendal nerve stimulation, such as additionally or alternatively to sacral neuromodulation. Chronic pudendal nerve stimulation was previously not possible, particularly over long periods of time. However, with the midfield techniques and devices discussed herein, long-term chronic stimulation is possible with minimal discomfort and minimal inconvenience to the patient or user.

Other pelvic areas can similarly be targeted for neural therapy to treat various disorders. For example, a midfield receiver and electrostimulation device can be installed at the lumbrosacral plexus to provide stimulation to neural targets at one or more of the sacral plexus, the genitofemoral nerve, or the sciatic nerve, or at branches thereof.

One or more of the systems, apparatuses, and methods discussed herein can be used to help treat sleep apnea and/or snoring by stimulating one or more of a nerve or nerve branches of the hypoglossal nerve, the base of the tongue (muscle), phrenic nerve(s), intercostal nerve(s), accessory nerve(s), and cervical nerves C3-C6. Treating sleep apnea and/or snoring can include providing energy to an implant to sense a decrease, impairment, or cessation of breathing (such as by measuring oxygen saturation).

One or more of the systems, apparatuses, and methods discussed herein can be used to help treat vaginal dryness, such as by stimulating one or more of Bartholin gland(s), Skene's gland(s), and inner wall of vagina. One or more of the systems, apparatuses, and methods discussed herein can be used to help treat migraines or other headaches, such as by stimulating one or more of the occipital nerve, supraorbital nerve, C2 cervical nerve, or branches thereof, and the frontal nerve, or branches thereof. One or more of the systems, apparatuses, and methods discussed herein can be used to help treat post-traumatic stress disorder, hot flashes, and/or complex regional pain syndrome such as by stimulating one or more of the stellate ganglion and the C4-C7 of the sympathetic chain.

One or more of the systems, apparatuses, and methods discussed herein can be used to help treat neuralgia (e.g., trigeminal neuralgia), such as by stimulating one or more of the sphenopalatine ganglion nerve block, the trigeminal nerve, or branches of the trigeminal nerve. One or more of the systems, apparatuses, and methods discussed herein can be used to help treat dry mouth (e.g., caused by side effects from medications, chemotherapy or radiation therapy cancer treatments, Sjogren's disease, or by other cause of dry mouth), such as by stimulating one or more of Parotid glands, submandibular glands, sublingual glands, submucosa of the oral mucosa in the oral cavity within the tissue of the buccal, labial, and/or lingual mucosa, the soft palate, the lateral parts of the hard palate, and/or the floor of the mouth and/or between muscle fibers of the tongue, Von Ebner glands, glossopharyngeal nerve (CN IX), including branches of CN IX, including otic ganglion, a facial nerve (CN VII), including branches of CN VII, such as the submandibular ganglion, and branches of T1-T3, such as the superior cervical ganglion.

One or more of the systems, apparatuses, and methods discussed herein can be used to help treat a transected nerve, such as by sensing electrical output from the proximal portion of a transected nerve and delivering electrical input into the distal portion of a transected nerve, and/or sensing electrical output from the distal portion of a transected nerve and delivering electrical input into the proximal portion of a transected nerve. One or more of the systems, apparatuses, and methods discussed herein can be used to help treat cerebral palsy, such as by stimulating one or more muscles or one or more nerves innervation one or more muscles affected in a patient with cerebral palsy. One or more of the systems, apparatuses, and methods discussed herein can be used to help treat erectile dysfunction, such as by stimulating one or more of pelvic splanchnic nerves (S2-S4) or any branches thereof, the pudendal nerve, cavernous nerve(s), and inferior hypogastric plexus.

One or more of the systems, apparatuses, and methods discussed herein can be used to help treat menstrual pain, such as by stimulating one or more of the uterus and the vagina. One or more of the systems, apparatuses, and methods discussed herein can be used as an intrauterine device, such as by sensing one or more PH and blood flow or delivering current or drugs to aid in contraception, fertility, bleeding, or pain. One or more of the systems, apparatuses, and methods discussed herein can be used to incite human arousal, such as by stimulating female genitalia, including external and internal stimulation, including stimulating a clitoris or other sensory active female parts, or by stimulating male genitalia.

One or more of the systems, apparatuses, and methods discussed herein can be used to help treat hypertension, such as by stimulating one or more of a carotid sinus, left or right cervical vagus nerve, or a branch of the vagus nerve. One or more of the systems, apparatuses, and methods discussed herein can be used to help treat paroxysmal supraventricular tachycardia, such as by stimulating one or more of trigeminal nerve or branches thereof, anterior ethmoidal nerve, and the vagus nerve. One or more of the systems, apparatuses, and methods discussed herein can be used to help treat vocal cord dysfunction, such as by sensing the activity of a vocal cord and the opposite vocal cord or just stimulating one or more of the vocal cords by stimulating nerves innervating the vocal cord, the left and/or Right recurrent laryngeal nerve, and the vagus nerve.

One or more of the systems, apparatuses, and methods discussed herein can be used to help repair tissue, such as by stimulating tissue to do one or more of enhancing microcirculation and protein synthesis to heal wounds and restoring integrity of connective and/or dermal tissues. One or more of the systems, apparatuses, and methods discussed herein can be used to help asthma or chronic obstructive pulmonary disease, such as by one or more of stimulating the vagus nerve or a branch thereof, blocking the release of norepinephrine and/or acetylcholine and/or interfering with receptors for norepinephrine and/or acetylcholine.

One or more of the systems, apparatuses, and methods discussed herein can be used to help treat cancer, such as by stimulating, to modulate one or more nerves near or in a tumor, such as to decrease the sympathetic innervation, such as epinephrine/NE release, and/or parasympathetic innervation, such as Ach. One or more of the systems, apparatuses, and methods discussed herein can be used to help treat diabetes, such as by powering a sensor inside the human body that detects parameters of diabetes, such as a glucose level or ketone level and using such sensor data to adjust delivery of exogenous insulin from an insulin pump. One or more of the systems, apparatuses, and methods discussed herein can be used to help treat diabetes, such as by powering a sensor inside the human body that detects parameters of diabetes, such as a glucose level or ketone level, and using a midfield coupler to stimulate the release of insulin from islet beta cells.

One or more of the systems, apparatuses, and methods discussed herein can be used to help treat neurological conditions, disorders or diseases (such as Parkinson's disease (e.g., by stimulating an internus or nucleus of the brain), Alzheimer's disease, Huntington's disease, dementia, Creutzfeldt-Jakob disease, epilepsy (e.g., by stimulating a left cervical vagus nerve or a trigeminal nerve), post-traumatic stress disorder (PTSD) (e.g., by stimulating a left cervical vagus nerve), or essential tremor, such as by stimulating a thalamus), neuralgia, depression, dystonia (e.g., by stimulating an internus or nucleus of the brain), phantom limb (e.g., by stimulating an amputated nerve, such an ending of an amputated nerve), dry eyes (e.g., by stimulating a lacrimal gland), arrhythmia (e.g., by stimulating the heart), a gastrointestinal disorder, such as obesity, gastroesophageal reflux, and/or gastroparesis, such as by stimulating a C1-C2 occipital nerve or deep brain stimulation (DBS) of the hypothalamus, an esophagus, a muscle near sphincter leading to the stomach, and/or a lower stomach, and/or stroke (e.g., by subdural stimulation of a motor cortex). Using one or more embodiments discussed herein, stimulation can be provided continuously, intermittently, on demand (e.g., as demanded by a physician, patient, or other user), or periodically.

Electrostimulation provided to or at neural targets in accordance with the teachings herein can be timed in various ways. For example, electrostimulation can be delivered continuously (e.g., chronically) or intermittently. In some examples, electrostimulation is delivered by an implanted device only when an external or source midfield device is in wireless communication with the implanted device. In other words, the implanted device stops or halts therapy when the external or source device is out of range. In an example, an electrostimulation therapy can be halted during user voiding (e.g., urination or defecation) to increase voiding efficiency and improve user comfort. In some examples, an electrostimulation therapy can be timed to be delivered only within about a half hour of user voiding. Such therapy timing can help to preserve device battery life and can help to avoid or delay an onset of physiologic resistance to a particular therapy. Such timing can be determined by a device learning algorithm, a user input, information from invasive and/or non-invasive sensors, or other means.

In providing the stimulation, an implantable receiver device can be situated up to about five centimeters or more below the surface of the skin. A midfield powering device is capable of delivering power to those depths in tissue. In one or more embodiments, an implantable device can be situated between about 2 centimeters and 4 centimeters, about 3 centimeters, between about 1 centimeter and five centimeters, less than 1 centimeter, about two centimeters, or other distance below the surface of the skin. The depth of implantation can depend on the use of the implanted device. For example, to treat depression, hypertension, epilepsy, and/or PTSD the implantable device can situated between about 2 centimeters and about four centimeters below the surface of the skin. In another example, to treat sleep apnea, arrhythmia (e.g., bradycardia), obesity, gastroesophageal reflux, and/or gastroparesis the implantable device can be situated at greater than about 3 centimeters below the surface of the skin. In yet another example, to treat Parkinson's, essential tremors, and/or dystonia the implantable device can be situated between about 1 centimeter and about 5 centimeters below the surface of the skin. Yet other examples include situating the implantable device between about 1 centimeter and about 2 centimeters below the surface of the skin, such as to treat fibromyalgia, stroke, and/or migraine, at about 2 centimeters to treat asthma, and at about one centimeter or less to treat dry eyes.

Although many embodiments included herein describe devices or methods for providing stimulation (e.g., electrostimulation), the embodiments may be adapted to provide other forms of modulation e.g., denervation) in addition to or instead of stimulation. In addition, although many embodiments included herein refer to the use of electrodes to deliver therapy, other energy delivery members (e.g., ultrasound transducers or other ultrasound energy delivery members) or other therapeutic members or substances (e.g., fluid delivery devices or members to deliver chemicals, drugs, cryogenic fluid, hot fluid or steam, or other fluids) may be used or delivered in other embodiments.

FIG. 1 illustrates, by way of example, a schematic of an embodiment of a system 100 using wireless communication paths. The system 100 includes an example of an external source 102, such as a midfield transmitter source, sometimes referred to as a midfield coupler or external transmitter device, located at or above an interface 105 between air 104 and a higher-index material 106, such as body tissue. In an example, a dielectric portion can be provided to occupy all or a portion of the region indicated to be air 104 in the example of FIG. 1. The external source 102 can produce a source current (e.g., an in-plane source current). The source current (e.g., in-plane source current) can generate an electric field and a magnetic field. The magnetic field can include a non-negligible component that is parallel to the surface of the source 102 and/or to a surface of the higher-index material 106 (e.g., a surface of the higher-index material 106 that faces the external source 102). In accordance with several embodiments, the external source 102 may comprise structural features and functions described in connection with the midfield couplers and external sources or transmitters included in WIPO Publication No. WO/2015/179225 published on Nov. 26, 2015 and titled "MIDFIELD COUPLER", which is incorporated herein by reference in its entirety, or the external source 102 may comprise structural features and functions described in connection with the midfield couplers and external sources or transmitters included in PCT Application No. PCT/US2018/016051, filed on Jan. 30, 2018, and titled "MIDFIELD TRANSMITTER AND RECEIVER SYSTEMS", which is incorporated herein by reference in its entirety.

The external source 102 can include at least a pair of outwardly facing electrodes 121 and 122. The electrodes 121 and 122 can be configured to contact a tissue surface, for example, at the interface 105. In one or more embodiments, the external source 102 is configured for use with a sleeve, pocket, or other garment or accessory that maintains the external source 102 adjacent to the higher-index material 106, and that optionally maintains the electrodes 121 and 122 in physical contact with a tissue surface. In one or more embodiments, the sleeve, pocket, or other garment or accessory can include or use a conductive fiber or fabric, and the electrodes 121 and 122 can be in physical contact with the tissue surface via the conductive fiber or fabric. Sleeves, pockets, or other garments or accessories suitable for use with the external source 102 are described further herein.

In one or more embodiments, more than two outwardly facing electrodes can be used and processor circuitry on-board or auxiliary to the source 102 can be configured to select an optimal pair or group of electrodes to use to sense farfield signal information (e.g., signal information corresponding to a delivered therapy signal or to a nearfield signal). In such embodiments, the electrodes can operate as antennas. In one or more embodiments, the source 102 includes three outwardly facing electrodes arranged as a triangle, or four outwardly facing electrodes arranged as a rectangle, and any two or more of the electrodes can be selected for sensing and/or can be electrically grouped or coupled together for sensing or diagnostics. In one or more embodiments, the processor circuitry can be configured to test multiple different electrode combination selections to identify an optimal configuration for sensing a farfield signal (an example of the processor circuitry is presented in FIG. 2A, among others).

FIG. 1 illustrates an embodiment of an implantable device 110, such as can include a multi-polar therapy delivery device configured to be implanted in the higher-index material 106. In one or more embodiments, the implantable device 110 includes all or a portion of the circuitry 500 from FIG. 5, discussed below. In one or more embodiments, the implantable device 110 is implanted in tissue below the tissue-air interface 105. In FIG. 1, the implantable device 110 includes an elongate body and multiple electrodes E0, E1, E2, and E3 that are axially spaced apart along a portion of the elongate body. The implantable device 110 includes receiver and/or transmitter circuitry (not shown in FIG. 1, see e.g., FIGS. 2A, 2B, and 4, among others) that can enable communication between the implantable device 110 and the external source 102.

The various electrodes E0-E3 can be configured to deliver electrostimulation therapy to patient tissue, such as at or near a neural or muscle target. In one or more embodiments, at least one electrode can be selected for use as an anode and at least one other electrode can be selected for use as a cathode to define an electrostimulation vector. In one or more embodiments, electrode E1 is selected for use as an anode and electrode E2 is selected for use as a cathode. Together, the E1-E2 combination defines an electrostimulation vector V12. Various vectors can be configured independently to provide a neural electrostimulation therapy to the same or different tissue target, such as concurrently or at different times.

In one or more embodiments, the source 102 includes an antenna (see, e.g., FIG. 3) and the implantable device 110 includes an antenna 108 (e.g., an electric field-based or magnetic field-based antenna). The antennas can be configured (e.g., in length, width, shape, material, etc.) to transmit and receive signals at substantially the same frequency. The implantable device 110 can be configured to transmit power and/or data signals through the antenna 108 to the external source 102 and can receive power and/or data signals transmitted by the external source 102. The external source 102 and implantable device 110 can be used for transmission and/or reception of RF signals. A transmit/receive (T/R) switch can be used to switch each RF port of the external source 102 from a transmit (transmit data or power) mode to a receive (receive data) mode. A T/R switch can similarly be used to switch the implantable device 110 between transmit and receive modes.

Figure 3:
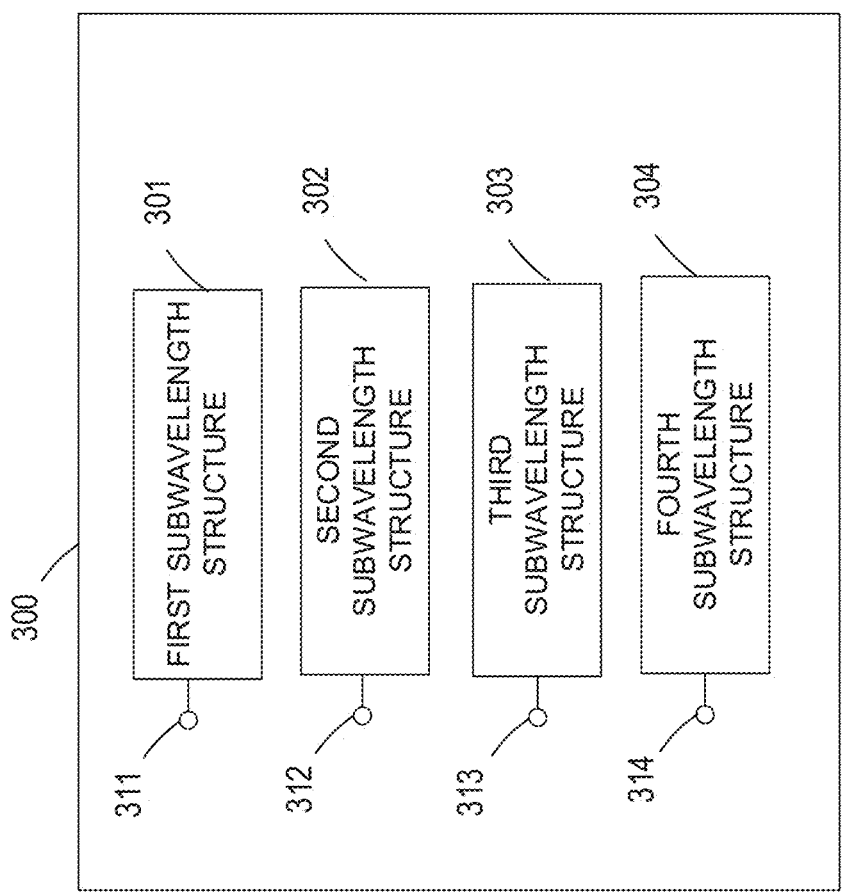
FIG. 3 illustrates, by way of example, a schematic view of an embodiment of a midfield antenna with multiple subwavelength structures.
Figure 4:
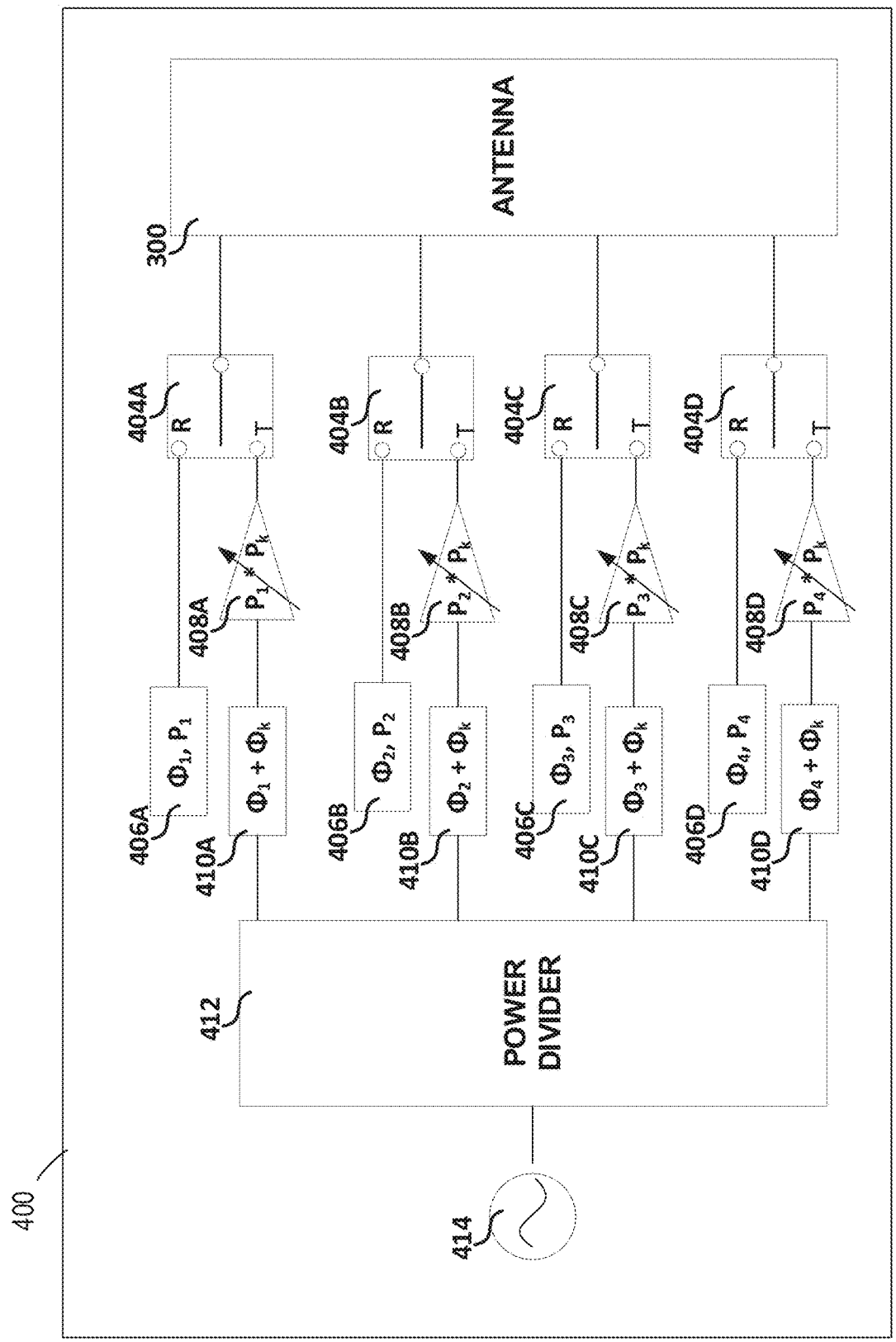
FIG. 4 illustrates, by way of example, a diagram of an embodiment of a phase-matching and/or amplitude-matching network for a midfield source device.

In one or more embodiments, a receive terminal on the external source 102 can be connected to one or more components that detect a phase and/or amplitude of a received signal from the implantable device 110. The phase and amplitude information can be used to program a phase of the transmit signal, such as to be substantially the same relative phase as a signal received from the implantable device 110. To help achieve this, the external source 102 can include or use a phase-matching and/or amplitude-matching network, such as shown in the embodiment of FIG. 4. The phase-matching and/or amplitude matching network can be configured for use with a midfield antenna that includes multiple ports, such as shown in the embodiment of FIG. 3.

Referring again to FIG. 1, in one or more embodiments, the implantable device 110 can be configured to receive a midfield signal 131 from the external source 102. The midfield signal 131 can include power and/or data signal components. In some embodiments, a power signal component can include one or more data components embedded therein. In one or more embodiments, the midfield signal 131 includes configuration data for use by the implantable device 110. The configuration data can define, among other things, therapy signal parameters, such as a therapy signal frequency, pulse width, amplitude, or other signal waveform parameters. In one or more embodiments, the implantable device 110 can be configured to deliver an electrostimulation therapy to a therapy target 190, such as can include a neural target (e.g., a nerve), a muscle target, or other tissue target. An electrostimulation therapy delivered to the therapy target 190 can be provided using a portion of a power signal received from the external source 102. Examples of the therapy target 190 can include nerve tissue or neural targets, for example including nerve tissue or neural targets at or near cervical, thoracic, lumbar, or sacral regions of the spine, brain tissue, muscle tissue, abnormal tissue (e.g., tumor or cancerous tissue), targets corresponding to sympathetic or parasympathetic nerve systems, targets at or near peripheral nerve bundles or fibers, at or near other targets selected to treat incontinence, urinary urge, overactive bladder, fecal incontinence, constipation, pain, neuralgia, pelvic pain, movement disorders or other diseases or disorders, deep brain stimulation (DBS) therapy targets or any other condition, disease or disorder (such as those other conditions, diseases, or disorders identified herein).

Delivering the electrostimulation therapy can include using a portion of a power signal received via the midfield signal 131, and providing a current signal to an electrode or an electrode pair (e.g., two or more of E0-E3), coupled to the implantable device 110, to stimulate the therapy target 190. As a result of the current signal provided to the electrode(s), a nearfield signal 132 can be generated. An electric potential difference resulting from the nearfield signal 132 can be detected remotely from the therapy delivery location. Various factors can influence where and whether the potential difference can be detected, including, among other things, characteristics of the therapy signal, a type or arrangement of the therapy delivery electrodes, and characteristics of any surrounding biologic tissue. Such a remotely detected electric potential difference can be considered a farfield signal 133. The farfield signal 133 can represent an attenuated portion of the nearfield signal 132. That is, the nearfield signal 132 and the farfield signal 133 can originate from the same signal or field, such as with the nearfield signal 132 considered to be associated with a region at or near the implantable device 110 and the therapy target 190, and with the farfield signal 133 considered to be associated with other regions more distal from the implantable device 110 and the therapy target 190. In one or more embodiments, information about the implantable device 110, or about a previously-provided or future planned therapy provided by the implantable device 110, can be encoded in a therapy signal and detected and decoded by the external source 102 by way of the farfield signal 133.

In one or more embodiments, the device 110 can be configured to provide a series of electrostimulation pulses to a tissue target (e.g., neural target). For example, the device 110 can provide multiple electrostimulation pulses separated in time, such as using the same or different electrostimulation vectors, to provide a therapy. In one or more embodiments, a therapy comprising multiple signals can be provided to multiple different vectors in parallel, or can be provided in sequence such as to provide a series or sequence of electrostimulation pulses to the same neural target. Thus, even if one vector is more optimal than the others for eliciting a patient response, the therapy as a whole can be more effective than stimulating only the known-optimal vector because (1) the target may experience a rest period during periods of non-stimulation, and/or (2) stimulating the areas nearby and/or adjacent to the optimal target can elicit some patient benefit.

In an example, the source is held in place near a treatment target with an underwear garment, discussed herein, such as to treat hypertonicity of the bladder, or overactive bladder. When the patient removes the underwear garment, such as during voiding, power or data communication from the source 102 to the device 110 can be interrupted or inhibited and, as a result, the device 110 can be signaled to halt therapy delivery, which in turn can help the patient excrete more efficiently. In other words, when therapy is stopped, a patient can urinate or defecate more efficiently, and therefore more comfortably, than when therapy is delivered concurrently with patient voiding. In an example, therapy delivery can resume, such as automatically, when the source 102 is replaced (e.g., with the underwear garment) near the device 110 and source-device communication is reestablished.

The system 100 can include a sensor 107 at or near the interface 105 between air 104 and the higher-index material 106. The sensor 107 can include, among other things, one or more electrodes, an optical sensor, an accelerometer, a temperature sensor, a force sensor, a pressure sensor, or a surface electromyography (EMG) device. The sensor 107 may comprise multiple sensors (e.g., two, three, four or more than four sensors). Depending on the type of sensor(s) used, the sensor 107 can be configured to monitor electrical, muscle, or other activity near the device 110 and/or near the source 102. For example, the sensor 107 can be configured to monitor muscle activity at a tissue surface. If muscle activity greater than a specified threshold activity level is detected, then a power level of the source 102 and/or of the device 110 can be adjusted. In one or more embodiments, the sensor 107 can be coupled to or integrated with the source 102, and in other examples, the sensor 107 can be separate from, and in data communication with (e.g., using a wired or wireless electrical coupling or connection), the source 102 and/or the device 110.

The system 100 can include a farfield sensor device 130 that can be separate from, or communicatively coupled with, one or more of the source 102 and the sensor 107. The farfield sensor device 130 can include two or more electrodes and can be configured to sense a farfield signal, such as the farfield signal 133 corresponding to a therapy delivered by the device 110. The farfield sensor device 130 can include at least one pair of outwardly facing electrodes 123 and 124 configured to contact a tissue surface, for example, at the interface 105. In one or more embodiments, three or more electrodes can be used, and processor circuitry on-board or auxiliary to the farfield sensor device 130 can select various combinations of two or more of the electrodes for use in sensing the farfield signal 133. In one or more embodiments, the farfield sensor device 130 can be configured for use with a sleeve, pocket, or other garment or accessory that maintains the farfield sensor device 130 adjacent to the higher-index material 106, and that optionally maintains the electrodes 123 and 124 in physical contact with a tissue surface. In one or more embodiments, the sleeve, pocket, or other garment or accessory can include or use a conductive fiber or fabric, and the electrodes 123 and 124 can be in physical contact with the tissue surface via the conductive fiber or fabric. Sleeves, pockets, or other garments or accessories suitable for use with the farfield sensor device 130 are described elsewhere herein. An example of at least a portion of a farfield sensor device 130 is further described herein in connection with FIG. 2B.

In one or more embodiments, the external source 102 provides a midfield signal 131 including power and/or data signals to the implantable device 110. The midfield signal 131 includes a signal (e.g., an RF signal) having various or adjustable amplitude, frequency, phase, and/or other signal characteristics. The implantable device 110 can include an antenna, such as described below, that can receive the midfield signal 131 and, based on characteristics of receiver circuitry in the implantable device 110, can modulate the received signal at the antenna to thereby generate a backscatter signal. In one or more embodiments, the implantable device 110 can encode information in the backscatter signal 112, such as information about a characteristic of the implantable device 110 itself, about a received portion of the midfield signal 131, about a therapy provided by the implantable device 110, and/or other information. The backscatter signal 112 can be received by an antenna at the external source 102 and/or the farfield sensor device 130, or can be received by another device. In one or more embodiments, a biological signal can be sensed by a sensor of the implantable device 110, such as a glucose sensor, an electropotential (e.g., an electromyography sensor, electrocardiograph (ECG) sensor, resistance, or other electrical sensor), a light sensor, a temperature, a pressure sensor, an oxygen sensor, a motion sensor, or the like. A signal representative of the detected biological signal can be modulated onto the backscatter 112. In an example, an external sensor 107 can include a monitor device, such as a glucose, temperature, ECG, EMG, oxygen, or other monitor, such as to receive, demodulate, interpret, and/or store data modulated onto the backscatter signal.

In one or more embodiments, the external source 102 and/or the implantable device 110 can include an optical transceiver configured to facilitate communication between the external source 102 and the implantable device 110. The external source 102 can include a light source, such as a photo laser diode or LED, or can include a photo detector, or can include both of a light source and a photo detector. The implantable device 110 can include a light source, such as a photo laser diode or LED, or can include a photo detector, or can include both of a light source and a photo detector. In an embodiment, the external source 102 and/or implantable device 110 can include a window, such as made of quartz, glass, or other translucent material, adjacent to its light source or photo detector. Garments or other accessories for positioning the source 102 adjacent to a tissue interface can include a window, such as made of a translucent material, a lower-density fabric, or including a through-hole. When the source 102 is placed in the garment, the garment window can be positioned at the location of the optical transceiver to facilitate light-based communication between the source 102 and implantable device 110. In an example, the garment includes or holds a dielectric insert between at least a portion of the source 102 and the tissue interface. An optical transceiver in the source 102 can be provided in a garment window that is adjacent to the dielectric, or a portion of the dielectric can be made from a translucent or sufficiently low-density material to enable light transmission therethrough.

In an embodiment, optical communications can be separate from or supplemental to an electromagnetic coupling between the external source 102 and the implantable device 110. Optical communication can be provided using light pulses modulated according to various protocols, such as using pulse position modulation (PPM). In an embodiment, a light source and/or photo detector on-board the implantable device 110 can be powered by a power signal received at least in part via midfield coupling with the external source 102.

In an embodiment, a light source at the external source 102 can send a communication signal through skin, into subcutaneous tissue, and through an optical window (e.g., quartz window) in the implantable device 110. The communication signal can be received at a photo detector on-board the implantable device 110. Various measurement information, therapy information, or other information from or about the implantable device can be encoded and transmitted from the implantable device 110 using a light source provided at the implantable device 110. The light signal emitted from the implantable device 110 can travel through the same optical window, subcutaneous tissue, and skin tissue, and can be received at photo detector on-board the external source 102. In an example, the light sources and/or photo detectors can be configured to emit and/or receive, respectively, electromagnetic waves in the visible or infrared ranges, such as in a range of about 670-910 nm wavelength (e.g., 670 nm-800 nm, 700 nm-760 nm, 670 nm-870 nm, 740 nm-850 nm, 800 nm 910 nm, overlapping ranges thereof, or any value within the recited ranges).

In one or more embodiments, multiple devices can be implanted in patient tissue and can be configured to deliver a therapy and/or sense physiologic information about a patient. The multiple implanted devices can be configured to communicate with one or more external devices. In one or more embodiments, the one or more external devices are configured to provide power and/or data signals to the multiple implanted devices, such as concurrently or in a time-multiplexed (e.g., "round-robin") fashion. The provided power and/or data signals can be steered or directed by an external device to efficiently transfer the signals to an implantable device. Although the present disclosure may refer to a power signal or data signal specifically, such references are to be generally understood as optionally including one or both of power and data signals. Such embodiments including multiple different implanted receiver devices and/or multiple different external devices in power and/or data communication are further discussed in U.S. patent application Ser. No. 15/770,032, filed on Apr. 20, 2018, and titled "DEVICES. SYSTEMS, AND METHODS FOR STIMULATION THERAPY", which is incorporated herein by reference in its entirety.

Several embodiments described herein are particularly advantageous because they include one, several, or all of the following benefits: (i) a dynamically configurable, active midfield transceiver that is configured to provide RF signals to modulate an evanescent field at a tissue surface and thereby generate a propagating field within tissue, such as to transmit power and/or a data signal to an implanted target device; (ii) a dynamically configurable, substantially passive midfield transceiver or lens that is configured to receive remote RF signals and in response provide RF signals to modulate an evanescent field at a tissue surface and thereby generate a propagating field within tissue, such as to transmit power and/or a data signal to an implanted target device; (iii) a tunable device for changing one or more RF signal receipt or transmission characteristics; (iv) feedback circuitry for updating or adjusting one or more signal receipt or transmission characteristics based on previous or current signal transmission activity; (v) adjustable midfield and far-field RF signal sources that can change a power transmit level based on information from one or more other midfield devices or implanted devices; (vi) providing power and/or data signals to multiple target devices using a common source device, such as concurrently or at different time intervals; (vii) sensing backscatter signal information to determine a quality of a signal transmission to a target device implanted in tissue; (viii) providing power and/or data signals to one target device using multiple different source devices; (ix) a wearable garment or accessory that can facilitate chronic placement of an external midfield transceiver adjacent to a tissue interface and near an implanted midfield device; (x) a dielectric insert, having a same or similar relative permittivity as air, configured to augment a wireless coupling between an external midfield transceiver and an implanted midfield device; (xi) a garment or accessory with a verification device or key that can enable use of a particular one or type of approved external midfield transceiver that is configured for use with a corresponding implanted midfield device; and/or circuitry, in one or both of an external midfield transceiver and implanted midfield device, configured to enhance patient voiding efficiency by inhibiting delivery of patient therapy when a patient voiding event is imminent or occurring.

In one or more embodiments, the implantable device 110 can include a digital controller 548, an amplifier 555, and/or stimulation driver circuitry 556, among other components of circuitry 500, such as comprise portions of a state machine device. See FIG. 5 for the digital controller 548, amplifier 555, and/or the stimulation driver circuitry 556.

The state machine device can be configured to wirelessly receive power and data signals via one or more pad(s) 536 and, in response, release or provide an electrostimulation signal via one or more outputs 534. In one or more embodiments, such a state machine device needs not retain information about available electrostimulation settings or vectors, and instead the state machine device carries out or provides electrostimulation events substantially immediately after, and in response to, receipt of instructions from the wireless transmitter or source 102.

For example, the state machine device can be configured to receive an instruction to deliver a neural electrostimulation therapy signal, such as at a specified time or having some specified signal characteristic (e.g., amplitude, duration, etc.), and the state machine device can respond by initiating or delivering the therapy signal. At a subsequent time, the device can receive a subsequent instruction to terminate the therapy, to change a signal characteristic, or to perform some other task. Thus, the device can optionally be configured to be substantially passive, or responsive to contemporaneously-received instructions. In an example, removing an external transmitter device from an optimized transmission location can compromise signal transmission efficiency to an implanted device. A weakly-received signal, or a lack of signal received at the implantable device 110, can cause the device or state machine to inhibit or terminate a therapy.

Distances or spacing between electrodes of an implantable device 110 can be changed to affect how widely a stimulation signal field is dispersed relative to a target. For example, an electrostimulation system comprising the implantable device 110 can be configured to use narrowly spaced electrodes when a target is nearby and to use more widely spaced electrodes when the target is further away or diffused over a larger area.

In accordance with several embodiments, a method of providing a wide area stimulation therapy using one or more instances of the implantable device 110 is provided. The method may comprise wirelessly receiving a power signal at a radio circuitry of an at least partially implantable stimulation device, the power signal generated by a midfield powering device, and, using a therapy delivery circuitry that is coupled to the radio circuitry and to multiple electrodes of the stimulation device, providing the wide area stimulation therapy signal to a patient using at least a portion of the wirelessly received power signal. The implantable stimulation device may include at least two first electrodes including at least one anode and at least one cathode on, or at least partially in, a distal portion of the stimulation device and at least one second electrode on, or at least partially in, a proximal portion of the stimulation device. In such an embodiment, providing the far field stimulation therapy signal may comprise switching, using the therapy delivery circuitry, one of the first electrodes off such that a far field electric field is generated between at least one of the first electrodes and the at least one second electrode. The method may further include switching on, using the therapy delivery circuitry, the first electrode that was switched off and switching off the at least one second electrode, and providing a localized stimulation therapy to the patient using at least a portion of the wirelessly received power, the localized stimulation therapy being generated between at least two of the first electrodes.

In accordance with several embodiments, a system comprises a midfield powering device and two implantable stimulation devices (e.g., two discrete instances of the implantable device 110) wirelessly coupled to the midfield powering device. For example, a first and second stimulation device each comprise or consist essentially of an antenna housing including an antenna situated therein to receive electric signals from the midfield powering device, a circuitry housing including therapy generation circuitry, and a plurality of electrodes electrically coupled to the therapy generation circuitry. The first and second stimulation devices may be arranged and configured to produce a wide area stimulation therapy between at least one electrode of the electrodes of the first stimulation device and at least one electrode of the electrodes of the second stimulation device. In some implementations, a distance between directly adjacent electrodes of the electrodes is less than ten millimeters (e.g., between eight and ten millimeters, between six and ten millimeters, between six and eight millimeters, between five and nine millimeters, between five and seven millimeters, between four and eight millimeters, between two and six millimeters, between one and five millimeters, overlapping ranges thereof, or any value within the recited ranges). A conductive wire may be electrically connected between an electrode of the electrodes of the first stimulation device and an electrode of the electrodes of the second stimulation device. In some embodiments, respective electrodes of the first stimulation device are configured as an anode and a cathode and respective electrodes of the second stimulation device are configured as a cathode and an anode and the therapy generation circuitry provides a localized stimulation therapy simultaneously with the wide area stimulation therapy. The electrodes in each of the stimulation devices may include a first electrode in a proximal portion of the stimulation device and a second electrode in a distal portion of the stimulation device, the proximal portion opposite the distal portion. The circuitry housing and the antenna housing may be situated between the first and second electrode or the circuitry housing and the antenna housing may be situated in a proximal portion of the stimulation device and the first and second electrode may be situated in an opposite distal portion of the stimulation device.

Figure 2A:
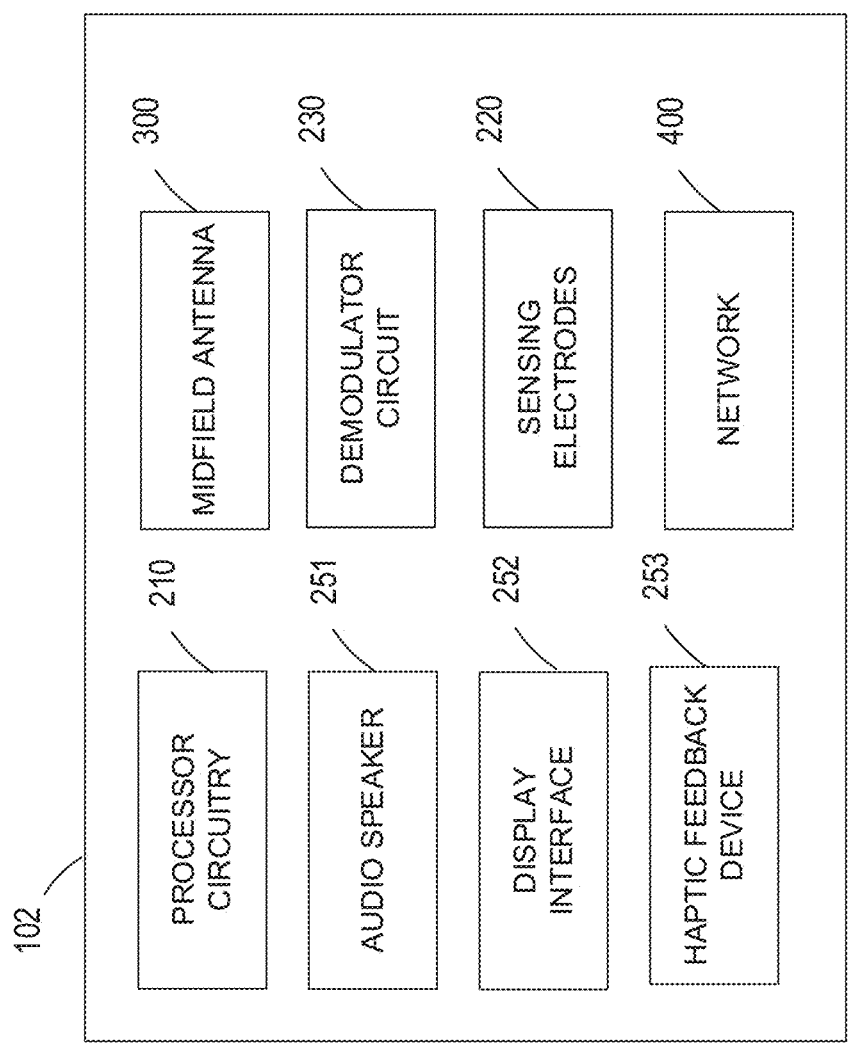
FIG. 2A illustrates, by way of example, a block diagram of an embodiment of a midfield source device.

FIG. 2A illustrates, by way of example, a block diagram of and embodiment of a midfield source device, such as the external source 102. The external source 102 can include various components, circuitry, or functional elements that are in data communication with one another. In the example of FIG. 2A, the external source 102 includes components, such as processor circuitry 210, one or more sensing electrodes 220 (e.g., including the electrodes 121 and 122), a demodulator circuitry 230, a phase-matching or amplitude-matching network 400, a midfield antenna 300, and/or one or more feedback devices, such as can include or use an audio speaker 251, a display interface 252, and/or a haptic feedback device 253. The midfield antenna 300 is further described below in the embodiment of FIG. 3, and the network 400 is further described below in the embodiment of FIG. 4. The processor circuitry 210 can be configured to coordinate the various functions and activities of the components, circuitry, and/or functional elements of the external source 102.

The midfield antenna 300 can be configured to provide a midfield excitation signal, such as can include RF signals having a non-negligible H-field component that is substantially parallel to an external tissue surface. In one or more embodiments, the RF signals can be adapted or selected to manipulate an evanescent field at or near a tissue surface, such as to transmit a power and/or data signal to respective different target devices (e.g., the implantable device 110) implanted in tissue. The midfield antenna 300 can be further configured to receive backscatter or other wireless signal information that can be demodulated by the demodulator circuitry 230. The demodulated signals can be interpreted by the processor circuitry 210. The midfield antenna 300 can include a dipole antenna, a loop antenna, a coil antenna, a slot or strip antenna, or other antenna. The antenna 300 can be shaped and sized to receive signals in a range of between about 400 MHz and about 4 GHz (e.g., between 400 MHz and 1 GHz, between 400 MHz and 3 GHz, between 500 MHz and 2 GHz, between 1 GHz and 3 GHz, between 500 MHz and 1.5 GHz, between 1 GHz and 2 GHz, between 2 GHz and 3 GHz, overlapping ranges thereof, or any value within the recited ranges). For embodiments incorporating a dipole antenna, the midfield antenna 300 may comprise a straight dipole with two substantially straight conductors, a folded dipole, a short dipole, a cage dipole, a bow-tie dipole or batwing dipole.

The demodulator circuitry 230 can be coupled to the sensing electrodes 220. In one or more embodiments, the sensing electrodes 220 can be configured to receive the farfield signal 133, such as based on a therapy provided by the implantable device 110, such as can be delivered to the therapy target 190. The therapy can include an embedded or intermittent data signal component that can be extracted from the farfield signal 133 by the demodulator circuitry 230. For example, the data signal component can include an amplitude-modulated or phase-modulated signal component that can be discerned from background noise or other signals and processed by the demodulator circuitry 230 to yield an information signal that can be interpreted by the processor circuitry 210. Based on the content of the information signal, the processor circuitry 210 can instruct one of the feedback devices to alert a patient, caregiver, or other system or individual. For example, in response to the information signal indicating successful delivery of a specified therapy, the processor circuitry 210 can instruct the audio speaker 251 to provide audible feedback to a patient, can instruct the display interface 252 to provide visual or graphical information to a patient, and/or can instruct the haptic feedback device 253 to provide a haptic stimulus to a patient. In one or more embodiments, the haptic feedback device 253 includes a transducer configured to vibrate or to provide another mechanical signal.

Figure 2B:
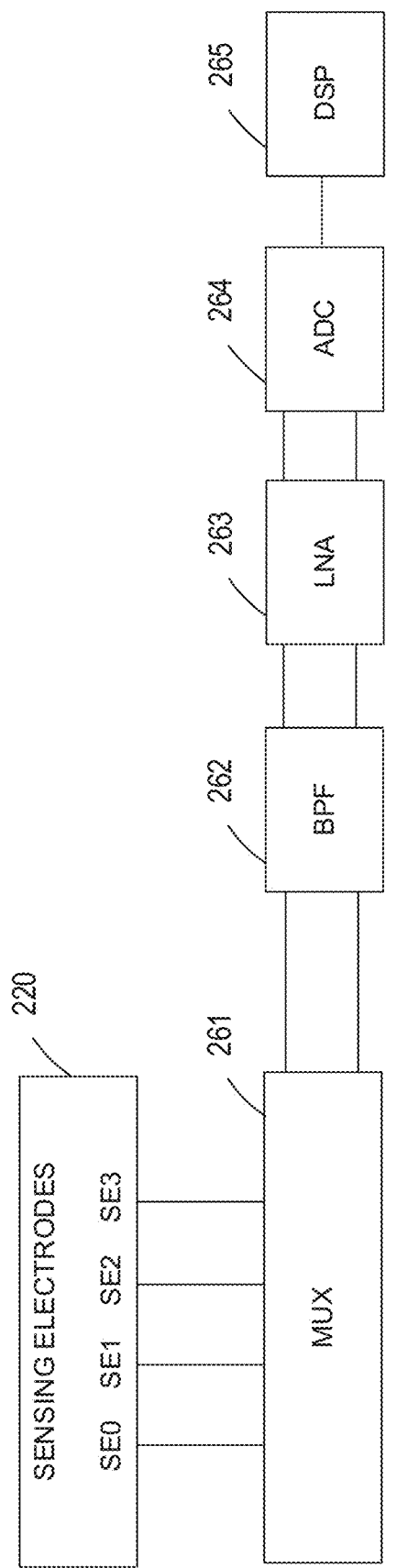
FIG. 2B illustrates, by way of example, a block diagram of an embodiment of a portion of a system configured to receive a signal.

FIG. 29 illustrates generally a block diagram of a portion of a system configured to receive a farfield signal. The system can include the sensing electrodes 220, such as can include the electrodes 121 and 122 of the source 102, or the electrodes 123 and 124 of the farfield sensor device 130. In the example of FIG. 2B, there are at least four sensing electrodes represented collectively as the sensing electrodes 220, and individually as SE0, SE1, SE2, and SE3; however, other numbers of sensing electrodes 220 may also be used. The sensing electrodes can be communicatively coupled to a multiplexer circuitry 261. The multiplexer circuitry 261 can select pairs of the electrodes, or electrode groups, for use in sensing farfield signal information. In one or more embodiments, the multiplexer circuitry 261 selects an electrode pair or grouping based on a detected highest signal to noise ratio of a received signal, or based on another relative indicator of signal quality, such as amplitude, frequency content, and/or other signal characteristic.

Sensed electrical signals from the multiplexer circuitry 261 can undergo various processing to extract information from the signals. For example, analog signals from the multiplexer circuitry 261 can be filtered by a band pass filter 262. The band pass filter 262 can be centered on a known or expected modulation frequency of a sensed signal of interest. A band pass filtered signal can then be amplified by a low-noise amplifier 263. The amplified signal can be converted to a digital signal by an analog-to-digital converter circuitry (ADC) 264. The digital signal can be further processed by various digital signal processors 265, as further described herein, such as to retrieve or extract an information signal communicated by the implantable device 110.

FIG. 3 illustrates, by way of example, a schematic view of an embodiment of a midfield antenna 300 with multiple subwavelength structures 301, 302, 303, and 304. The midfield antenna 300 can include a midfield plate structure with a planar surface. The one or more subwavelength structures 301-304 can be formed in the plate structure. In the example of FIG. 3, the antenna 300 includes a first subwavelength structure 301, a second subwavelength structure 302, a third subwavelength structure 303, and a fourth subwavelength structure 304. Fewer or additional subwavelength structures can be used. The subwavelength structures can be excited individually or selectively by one or more RF ports (e.g., first through fourth RF ports 311, 312, 313, and 314) respectively coupled thereto. A "subwavelength structure" can include a hardware structure with dimensions defined relative to a wavelength of a field that is rendered and/or received by the external source 102. For example, for a given $\lambda_0$ corresponding to a signal wavelength in air, a source structure that includes one or more dimensions less than can be considered to be a subwavelength structure. Various designs or configurations of subwavelength structures can be used. Some examples of a subwavelength structure can include a slot in a planar structure, or a strip or patch of a conductive sheet of substantially planar material (e.g., a microstrip or similar conductive feature on a PCB).

FIG. 4 illustrates generally an example of the phase-matching or amplitude-matching network 400, such as can comprise a portion of the source 102. In an embodiment, the network 400 can include the antenna 300, and the antenna 300 can be electrically coupled to a plurality of switches 404A, 404B, 404C, and 404D, for example, via the first through fourth RF ports 311, 312, 313, and 314 illustrated in FIG. 3. The switches 404A-D are each electrically coupled to a respective phase and/or amplitude detector 406A, 406B, 406C, and 406D, and a respective variable gain amplifier 408A, 408B, 408C, and 408D. Each amplifier 408A-D is electrically coupled to a respective phase shifter 410A, 410B, 410C, and 410D, and each phase shifter 410A-D is electrically coupled to a common power divider 412 that receives an RF input signal 414 to be transmitted using the external source 102.

In one or more embodiments, the switches 404A-D can be configured to select either a receive line ("R") or a transmit line ("T"). A number of switches 404A-D of the network 400 can be equal to a number of ports of the midfield source 402. In the example of the network 400, the midfield source 402 includes four ports (e.g., corresponding to the four subwavelength structures in the antenna 300 of the example of FIG. 3), however any number of ports (and switches), such as one, two, three, four, five, six, seven, eight or more, can be used.

The phase and/or amplitude detectors 406A-D are configured to detect a phase ($\Phi1$, $\Phi2$, $\Phi3$, $\Phi4$) and/or power (P1, P2, P3, P4) of a signal received at each respective port of the midfield source 402. In one or more embodiments, the phase and/or amplitude detectors 406A-D can be implemented in one or more modules (hardware modules that can include electric or electronic components arranged to perform an operation, such as determining a phase or amplitude of a signal), such as including a phase detector module and/or an amplitude detector module. The detectors 406A-D can include analog and/or digital components arranged to produce one or more signals representative of a phase and/or amplitude of a signal received at the external source 102.

The amplifiers 408A-D can receive respective inputs from the phase shifters 410A-D (e.g., Pk phase shifted by $\Phi$k, $\Phi1+\Phi$k, $\Phi2+\Phi$k, $\Phi3+\Phi$k, or $\Phi4+\Phi$k). The output of the amplifier, O, is generally the output of the power divider, M when the RF signal 414 has an amplitude of 4*M (in the embodiment of FIG. 4), multiplied by the gain of the amplifier Pi*Pk. Pk can be set dynamically as the values for P1, P2, P3, and/or P4 change, $\Phi$k can be a constant. In one or more embodiments, the phase shifters 410A-D can dynamically or responsively configure the relative phases of the ports based on phase information received from the detectors 406A-D.

In one or more embodiments, a transmit power requirement from the midfield source 402 is Ptt. The RF signal provided to the power divider 412 has a power of 4*M. The output of the amplifier 408A is about M*P1*Pk. Thus, the power transmitted from the midfield coupler is M*(P1*Pk+ *Pk+F+P3*Pk+P4*Pk)=Ptt. Solving for Pk yields Pk=Ptt/(M*(P1+P2+P3+P4)).

The amplitude of a signal at each RF port can be transmitted with the same relative (scaled) amplitude as the signal received at the respective port of the midfield coupler coupled thereto. The gain of the amplifiers 408A-D can be further refined to account for any losses between the transmission and reception of the signal from the midfield coupler. Consider a reception efficiency of $\eta$=Pir/Ptt, where Pir is the power received at the implanted receiver. An efficiency (e.g., a maximum efficiency), given a specified phase and amplitude tuning, can be estimated from an amplitude received at the external midfield source from the implantable source. This estimation can be given as $\eta\approx$(P1+P2+P3+P4)/Pit, where Pit is an original power of a signal from the implanted source. Information about a magnitude of the power transmitted from the implantable device 110 can be communicated as a data, signal to the external source 102. In one or more embodiments, an amplitude of a signal received at an amplifier 408A-D can be scaled according to the determined efficiency, such as to ensure that the implantable device receives power to perform one or more programmed operation(s). Given the estimated link efficiency, $\eta$, and an implant power (e.g., amplitude) requirement of Pir', Pk can be scaled as Pk=Pir'/[$\eta$(P1+P2+P3+P4)], such as to help ensure that the implant receives adequate power to perform the programmed functions.

Control signals for the phase shifters 410A-D and the amplifiers 408A-D, such as the phase input and gain input, respectively, can be provided by processing circuitry that is not shown in FIG. 4. The circuitry is omitted to not overly complicate or obscure the view provided in FIG. 4. The same or different processing circuitry can be used to update a status of one or more of the switches 404A-D between receive and transmit configurations. See the processor circuitry 210 of FIG. 2A and its associated description for an example of processing circuitry.

Figure 5:
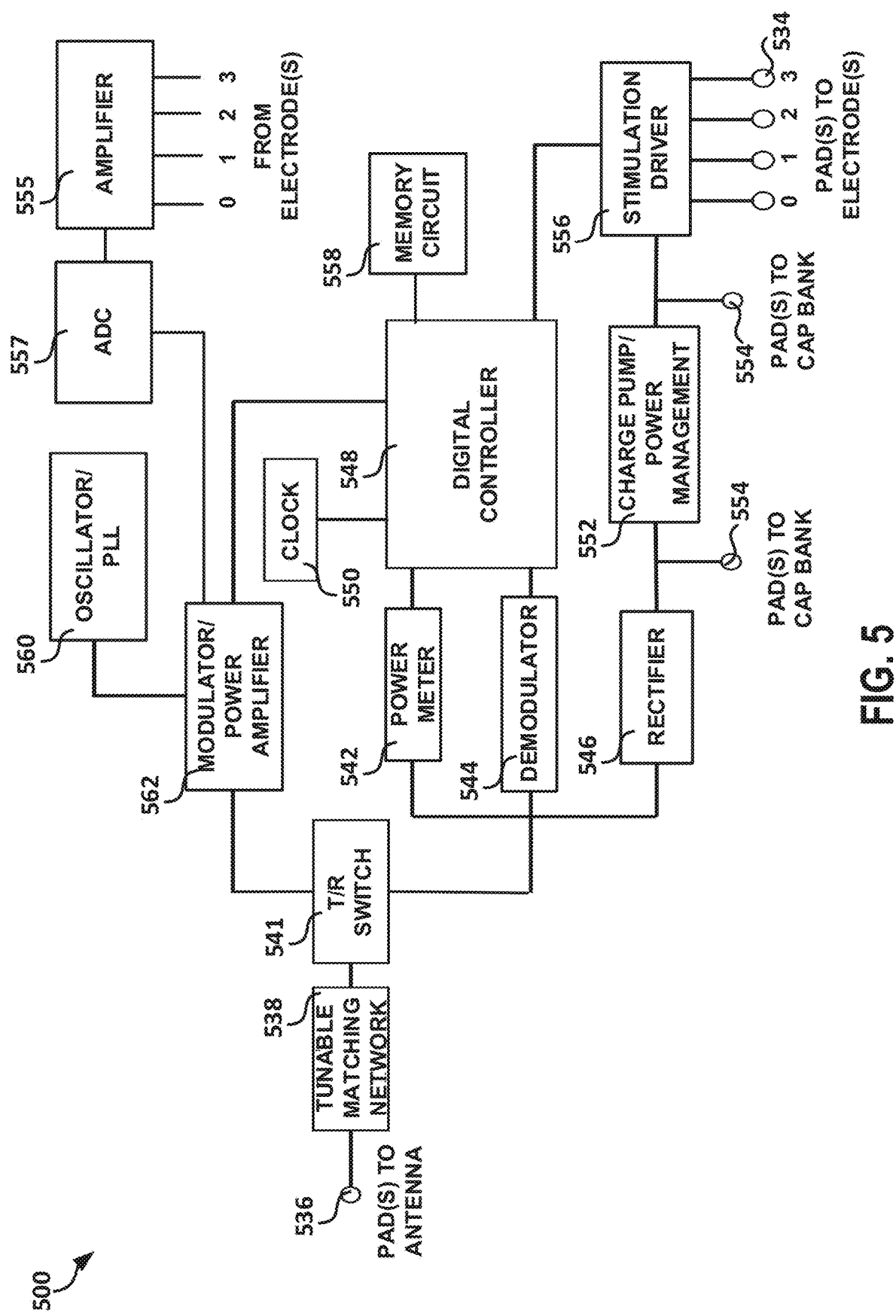
FIG. 5 illustrates, by way of example, a diagram of an embodiment of circuitry of an implantable device.

FIG. 5 illustrates, by way of example, a diagram of an embodiment of circuitry 500 of the implantable device 110, or target device. The circuitry 500 includes one or more pad(s) 536, such as can be electrically connected to the antenna 108. The circuitry 500 can include a tunable matching network 538 to set an impedance of the antenna 108 based on an input impedance of the circuitry 500. The impedance of the antenna 108 can change, for example, due to environmental changes. The tunable matching network 538 can adjust the input impedance of the circuitry 500 based on the varying impedance of the antenna 108. In one or more embodiments, the impedance of the tunable matching network 538 can be matched to the impedance of the antenna 108. In one or more embodiments, the impedance of the tunable matching network 538 can be set to cause a portion of a signal incident on the antenna 108 to reflect back from the antenna 108, thus creating a backscatter signal.

A transmit-receive (T/R) switch 541 can be used to switch the circuitry 500 from a receive mode (e.g., in which power and/or data signals can be received) to a transmit mode (e.g., in which signals can be transmitted to another device, implanted or external). An active transmitter can operate at an Industrial, Scientific, and Medical (ISM) band of 2.45 GHZ or 915 MHz, or the 402 MHz Medical Implant Communication Service (MICS) band for transferring data from the implant. Alternatively, data can be transmitted using a Surface Acoustic Wave (SAW) device that backscatters incident radio frequency (RF) energy to the external device.

The circuitry 500 can include a power meter 542 for detecting an amount of received power at the implanted device. A signal that indicates power from the power meter 542 can be used by a digital controller 548 to determine whether received power is adequate (e.g., above a specified threshold) for the circuitry to perform some specified function. A relative value of a signal produced by the power meter 542 can be used to indicate to a user or machine whether an external device (e.g., the source 102) used to power the circuitry 500 is in a suitable location for transferring power and/or data to the target device. In an example, if the source 102 is determined to be outside of a suitable location, an indication can be provided to a user to adjust or reconfigure the source 102 and/or a garment that retains the source 102.

In one or more embodiments, the circuitry 500 can include a demodulator 544 for demodulating received data signals. Demodulation can include extracting an original information-bearing signal from a modulated carrier signal. In one or more embodiments, the circuitry 500 can include a rectifier 546 for rectifying a received AC power signal.

Circuitry (e.g., state logic, Boolean logic, or the like) can be integrated into the digital controller 548. The digital controller 548 can be configured to control various functions of the receiver device, such as based on the input(s) from one or more of the power meter 542, demodulator 544, and/or the clock 550. In one or more embodiments, the digital controller 548 can control which electrode(s) (e.g., E0-E3) are configured as a current sink (anode) and which electrode(s) are configured as a current source (cathode). In one or more embodiments, the digital controller 548 can control a magnitude of a stimulation pulse produced through the electrode(s).

A charge pump 552 can be used to increase the rectified voltage to a higher voltage level, such as can be suitable for stimulation of the nervous system. The charge pump 552 can use one or more discrete components to store charge for increasing the rectified voltage. In one or more embodiments, the discrete components include one or more capacitors, such as can be coupled to pad(s) 554. In one or more embodiments, these capacitors can be used for charge balancing during stimulation, such as to help avoid tissue damage.

A stimulation driver circuitry 556 can provide programmable stimulation through various outputs 534, such as to an electrode array. The stimulation driver circuitry 556 can include impedance measurement circuitry, such as can be used to test for correct positioning of the electrode(s) of the array. The stimulation driver circuitry 556 can be programmed by the digital controller to make an electrode a current source, a current sink, or a shorted signal path. The stimulation driver circuitry 556 can be a voltage or a current driver. The stimulation driver circuitry 556 can include or use a therapy delivery circuitry that is configured to provide electrostimulation signal pulses to one or more electrodes, such as using at least a portion of a received midfield power signal from the external source 102. In one or more embodiments, the stimulation driver circuitry 556 can provide pulses at frequencies up to about 100 kHz. Pulses at frequencies around 100 kHz can be useful for nerve blocking.

The circuitry 500 can further include a memory circuitry 558, such as can include a non-volatile memory circuitry. The memory circuitry 558 can include storage of a device identification, neural recordings, and/or programming parameters, among other implant related data.

The circuitry 500 can include an amplifier 555 and analog digital converter (ADC) 557 to receive signals from the electrode(s). The electrode(s) can sense electricity from nerve signals within the body. The nerve signals can be amplified by the amplifier 555. These amplified signals can be converted to digital signals by the ADC 557. These digital signals can be communicated to an external device. The amplifier 555, in one or more embodiments, can be a trans-impedance amplifier.

The digital controller 548 can provide data to a modulator/power amplifier 562. The modulator/power amplifier 562 modulates the data onto a carrier wave. The power amplifier 562 increases the magnitude of the modulated waveform to be transmitted.

The modulator/power amplifier 562 can be driven by an oscillator/phase locked loop (PLL) 560. The PILL disciplines the oscillator so that it remains more precise. The oscillator can optionally use a different clock from the clock 550. The oscillator can be configured to generate an RF signal used to transmit data to an external device. A typical frequency range for the oscillator is about 10 kHz to about 2600 MHz (e.g., from 10 kHz to 1000 MHz, from 500 kHz to 1500 kHz, from 10 kHz to 100 kHz, from 50 kHz to 200 kHz, from 100 kHz to 500 kHz, from 100 kHz to 1000 kHz, from 500 kHz to 2 MHz, from 1 MHz to 2 MHz, from 1 MHz to 10 MHz, from 100 MHz to 1000 MHz, from 500 MHz, to 2500 MHz, overlapping ranges thereof, or any value within the recited ranges). Other frequencies can be used, such as can be dependent on the application. The clock 550 is used for timing of the digital controller 548. A typical frequency of the clock 550 is between about one kilohertz and about one megahertz (e.g., between 1 kHz and 100 kHz, between 10 kHz and 150 kHz, between 100 kHz and 500 kHz, between 400 kHz and 800 kHz, between 500 kHz and 1 MHz, between 750 kHz and 1 MHz, overlapping ranges thereof, or any value within the recited ranges). Other frequencies can be used depending on the application. A faster clock generally uses more power than a slower clock.

A return path for a signal sensed from a nerve is optional. Such a path can include the amplifier 555, the ADC 557, the oscillator PLL 560, and the modulator/power amplifier 562. Each of these items and connections thereto can optionally be removed.

In some embodiments of the midfield source devices described herein, a target or focal region can be adjusted, such as without mechanical reconfiguration of the source, using degrees of freedom provided by the amplitudes and phases of the input port signals. Such field directing or focusing can be useful in applications in which a source may be used to power implantable devices configured to interact with organs in rhythmic motion (e.g., due to breathing or heartbeat), to power one or more implantable devices, to power an implantable device that is movable inside the body, or to provide power from a source that is movable relative to the implantable device 110. For example, a source retained by a garment adjacent to a tissue surface can update a focal region as the garment, and therefore the source, moves due to normal ambulation or movement of the user.

To shift a focal region, excitation signal characteristics for different subwavelength structures (e.g., subwavelength structures that are part of the same or different source device) can be configured and reconfigured, such as in real-time, such as to enable various field patterns to be provided.

Figure 6:
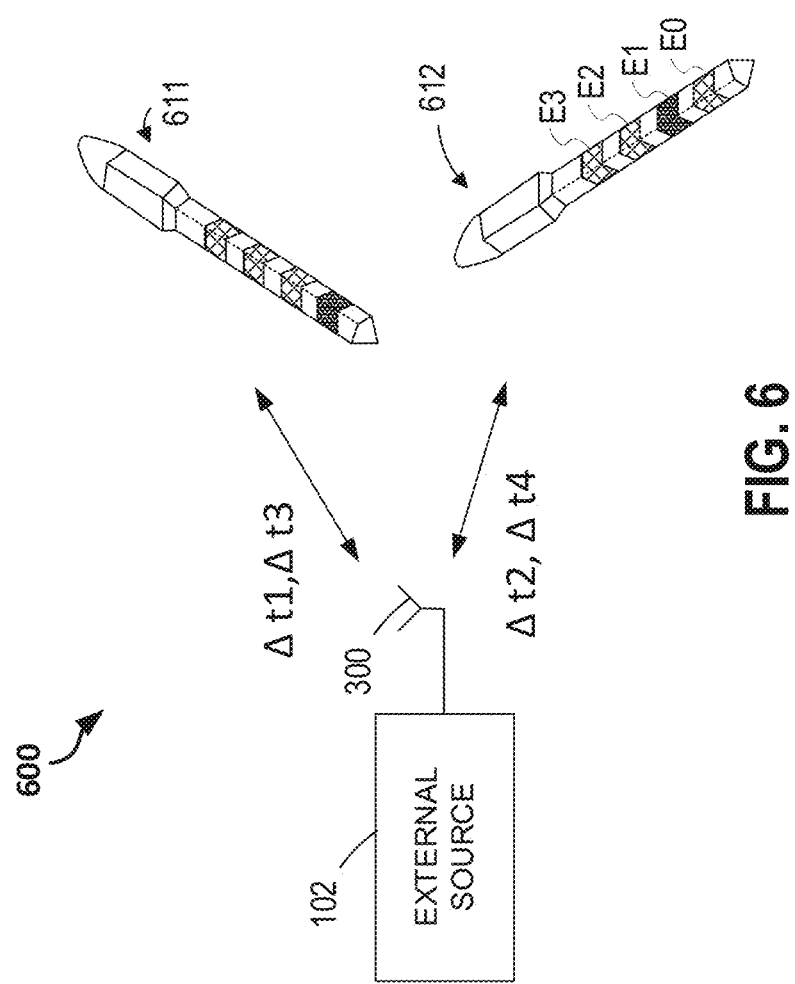
FIG. 6 illustrates, by way of example, a diagram of an embodiment of a system for selectively providing power and/or data communication to multiple target devices.

FIG. 6 illustrates, by way of example, a diagram of an embodiment of a system 600 for selectively providing power and/or a data communication signals to (respective) multiple target devices. The system 600 includes the antenna 300 (see FIG. 3), such as can be included or used in the source 102 (see FIG. 1). The antenna 300 can be configured to communicate power and/or data signals to one or both of a first target device 611 and a second target device 612. That is, the external midfield device (e.g., the antenna 300 or circuitry that can be electrically coupled thereto, such as illustrated in FIG. 4 among other FIGS.) can be configured to manipulate an evanescent field at or near an external tissue surface to direct transmission of wireless power and/or data signals within the tissue, such as to the first and/or second target device 611 and 612.

In FIG. 6, the first and second target devices 611 and 612 are therapy delivery or sensor devices, and each includes multiple electrodes E0, E1, E2, and E3. Other target devices can similarly be used and may have different numbers and/or configurations of electrodes. The first target device 611 and the second target device 612 can be similar to or the same as the implantable device 110, or other implantable device discussed herein.

In one or more embodiments, the external midfield device communicates signals to the first and second target devices 611 and 612 at different, non-overlapping time intervals. For example, the external midfield device can send signals to and/or receive signals from the first target device 611 during a first interval Δt1 and a third interval Δt3, and the external midfield device can send signals to and/or receive signals from the second target device 612 during a second interval Δt2 and a fourth interval Δt4. The external midfield device can communicate power and/or data in a round-robin manner, with the antenna 300 providing different signals to different targets at different times. Optionally, the external midfield device provides a blanking period or delay between the different communication intervals.

Referring again to the examples of FIGS. 1, 2A, 3, and/or 4, the source 102 includes an assembly with electronic control hardware, such as including the network 400, and an electromagnetic transmitting element or elements, such as including the antenna 300. The assembly can be packaged in various ways. For example, in one or more embodiments, devices, systems, and methods include an electromagnetic transmission element mounted to a common substrate or PCB as its associated control hardware.

Control hardware can include electronics components (passive components (e.g., diodes, transistors, resistors, capacitors, inductors, or the like), discrete integrated circuits, logic components (e.g., logic gates, multiplexers, or the like), application specific integrated circuits (ASICs)) as well as metallic traces which connect signal and power pads for each of the components. During a design process, the coupling between the electronic control hardware and an electromagnetic transmission element (e.g., an antenna) is carefully managed, and almost inevitably results in a loss of efficiency for the electromagnetic transmission element and/or a loss of signal integrity for the electronic components. This loss of efficiency and/or signal integrity becomes more impactful in packages with compact designs. Embodiments discussed in this subsection can help overcome the loss of efficiency in the transmission element and/or the loss of signal integrity in the electronic components.

In an example, devices, systems, and methods include integrating control hardware into a planar electromagnetic transmission element in an electronic device package (e.g., on a printed circuitry board (PCB), a flexible substrate, or other medium on which an electronic device can reside). There are many types of planar electromagnetic transmission elements including a microstrip or patch antenna, a slot antenna, or a combination thereof. These antennas can be made in a variety of shapes and sizes and configured to interact (efficiently) with a wide variety of electromagnetic signal frequencies. Another type of planar electromagnetic transmission element includes a mid-field antenna, such as a midfield antenna described in WIPO Publication No. WO/2015/179225, which is incorporated herein by reference.

Decreasing a form factor of a package that includes such a planar electromagnetic transmission element is difficult due at least in part to efficiency and signal losses from electromagnetic radiation communicating between components near the electromagnetic transmission element. Thus, integrating control hardware into a planar antenna or electromagnetic element on a printed computer board (PCB) can cause undesirable losses in the signal integrity and performance of the electromagnetic control element. These effects can be more of a concern when package size is reduced and an electromagnetic transmission element covers a larger proportion or majority of a footprint of the package.

In the case of a mid-field powering coupler (electromagnetic transmission element), the planar metal pattern which provides efficient energy transfer to an implanted device an implanted medical device) may be several centimeters in length in length and width dimensions. Control hardware (e.g., electronic hardware components) can be used to provide Radio Frequency (RF) power to ports of the mid-field coupler, modulate the RF signal for communication with the implanted device, receive communications from the implanted device, and/or provide a user interface for the patent/clinician to set one or more parameters of the circuitry or receive data from the implanted device. The control hardware can be provided on a separate PCB from the mid-field powering coupler, but at the cost of size (form factor).

For attaching the circuitry (the electromagnetic transmission device and the control hardware) to the body, it can be beneficial to have dimensions of the integrated device (electromagnetic transmission element and control hardware) near the same dimensions as the electromagnetic transmission element, which can occupy the largest surface area of the transmission element, so as to reduce the form factor of the integrated circuitry. To reduce the form factor further, the electronic components can be integrated on the same substrate as the mid-field powering coupler. For example, in a two-board integrated circuit where the RF signal is sourced from a board separate from the midfield coupler e.g., the control hardware is on a board separate from the electromagnetic transmission element) the circuitry may have an overall thickness of 15 mm or more. In contrast, a single board solution (e.g., a device that includes the control hardware on the same board as the electromagnetic transmission element) can have an overall thickness of about 3 mm (e.g., 1 mm to 5 mm, 2 mm to 4 mm). The volume saved from the integration can be used for additional battery capacity or can allow for the device to be housed in a thinner package that is less obtrusive or visible, such as when the device is worn on the body (e.g., using a garment or other accessor to hold the device near or adjacent to the body).

Due to the limited area of outer layers of a circuitry substrate (e.g., a PCB or flexible substrate), it can be difficult to integrate the components and traces with the electromagnetic transmission element. In one or more embodiments, the hardware control components can be placed on the same layers as the patterned electromagnetic transmission element and microstrip feed lines for excitation of the electromagnetic transmission element. The placement of these components and traces along these layers can cause undesired coupling that can cause communication between the control hardware and the electromagnetic transmission element, resulting is loss of signal integrity and/or power transfer efficiency.

An advantage of one or more embodiments can include one or more of: (i) circuitry operating with reduced noise from the environment; and (ii) a mid-field powering device with a reduced form factor, such as compared to one with control circuitry and a transmission element on separate boards; among others.

Figure 7:
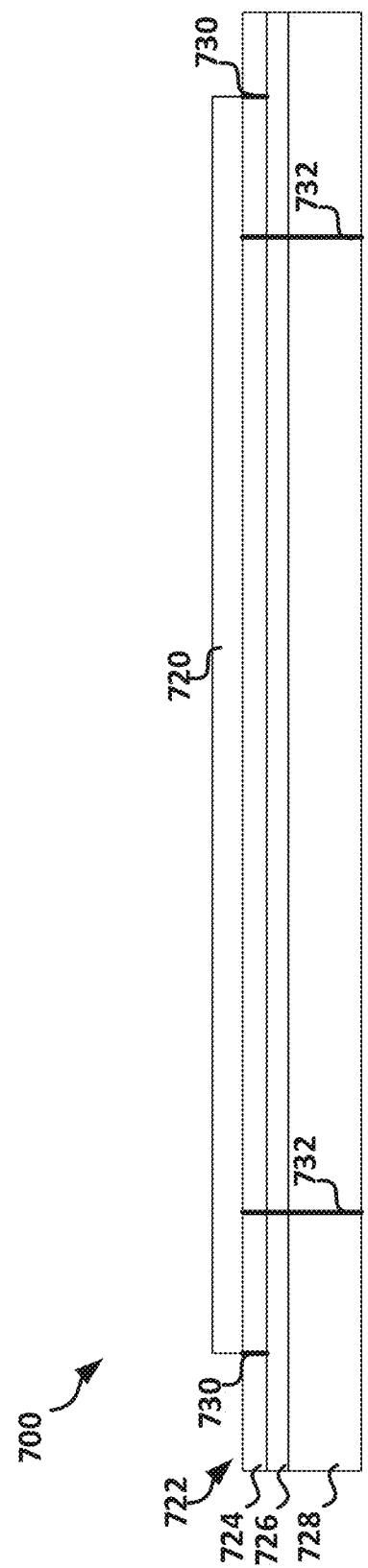
FIG. 7 illustrates, by way of example, a perspective view diagram of an embodiment of a system that includes control hardware and an electromagnetic transmission element on an integrated board structure.

FIG. 7 illustrates, by way of example, a perspective view diagram of an embodiment of a system 700 that includes components of the source 102, such as the control hardware and the electromagnetic transmission element, on a single board 722 or substrate. The system 700 as illustrated includes the control hardware and the transmission element on a top layer of the substrate (not illustrated). The transmission element is separated from the control hardware by a faraday cage 720 or other element that excludes or inhibits ingress of electrostatic or electromagnetic energy, such as to shield the control hardware from electromagnetic radiation of the transmission element and vice versa.

The faraday cage 720 can be a part of the electromagnetic transmission element that radiates. The control components are fully integrated within a conductive surface of the transmission element using the faraday cage 720. In such embodiments, the faraday cage 720 is acting both as a shield (for the control components) and as a radiating element of the transmission element. Due to the skin depth of the material used for the faraday cage 720, the electromagnetic currents at the outer surface of the faraday cage that induce radiation do not penetrate more than several microns at gigahertz frequencies. Thus, the internal components can advantageously be shielded from the electromagnetic fields induced by the faraday cage 720 radiating as part of the transmission element, in accordance with one or more embodiments.

In one or more embodiments, the board 722 can include multiple layers, such as a first layer 724, a second layer 726, and a third layer 728. The third layer 728 can be thicker than the first layer 724 and the second layer 726. In one or more embodiments, the board 722 can be made of an FR4 substrate (e.g., a glass-reinforced epoxy laminate comprising a composite material composed of woven fiberglass cloth with an epoxy resin binder that is flame resistant), a silicon substrate, ajinomoto build-up film (AU), a dielectric, or other material. The control hardware can be situated on a top surface of the first layer 724 along with routing (e.g., traces) between components of the control hardware. The components of the control hardware (e.g., high power components) may have thermally conductive material applied to conduct heat to the faraday cage 720.

A ground plane can be situated on the second layer 726. The faraday cage 720 can be shorted to the ground plane by one or more vias 730. One or more vias 732 can provide a signal to a port of a slot 734 (e.g., a resonating element) on the third layer 728. The signal to the port can be from one of the power amplifiers. The faraday cage 720 and the ground plane can be configured with corresponding slots (a slot pattern).

In one or more embodiments, the control hardware components are placed on a surface layer of the board 722 with a majority of the routing provided on the same surface layer. In the embodiment of FIG. 7, the control hardware and most of the routing are on a top surface of the first layer 724 (e.g., the surface on which the faraday cage 720 is mounted).

In one or more embodiments, the slot mid-field pattern (e.g., ground plane) can be printed on, or at least partially in, the second layer 726 (e.g., the layer immediately below the first layer 724). In one or more embodiments, the second layer 726 can also serve as a ground plane. One or more vias 730 can be included that connect the first layer 724 with the second layer 726, such as to short the faraday cage 720 at the top layer to ground. In one or more embodiments, the vias 730 can be at or near the edges of the mid-field pattern and/or the edges of the slots which form the midfield element. Layers between the ground plane and excitation ports along a bottom surface of the third layer 728 may be used for limited traces. In some embodiments, microstrip excitation slots or feeds are positioned along or adjacent a bottom surface of the third layer 728.

Figure 8:
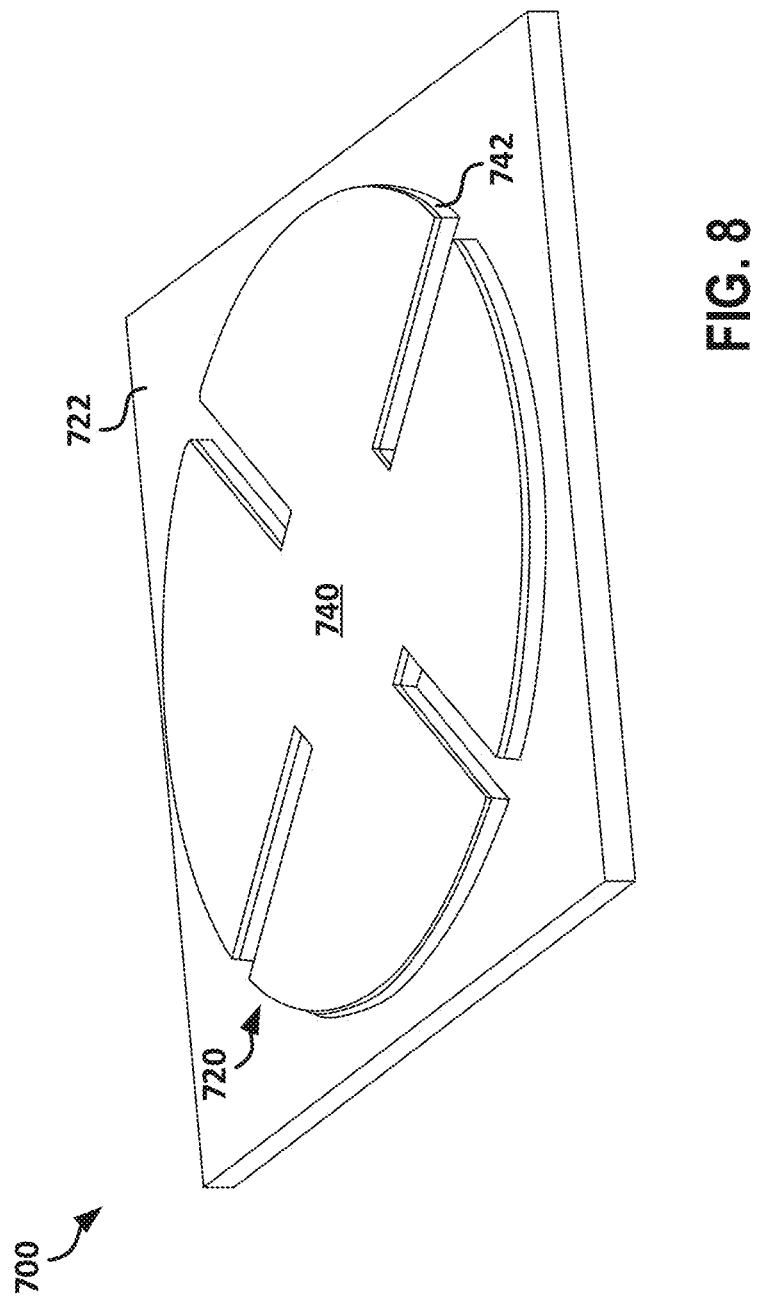
FIG. 8 illustrates, by way of example, a perspective view diagram of an embodiment of a system that includes a faraday cage cover over components of control circuitry.
Figure 9A:
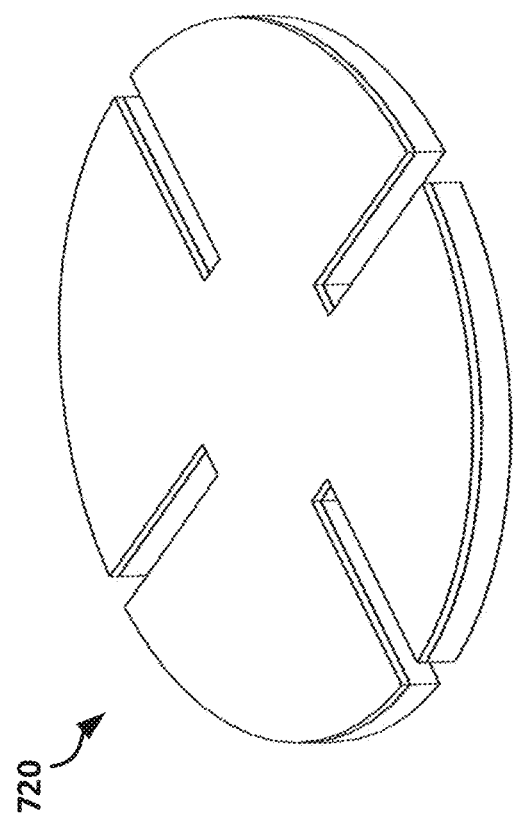
FIG. 9A illustrates, by way of example, a perspective view diagram of an embodiment a faraday cage.
Figure 9B:
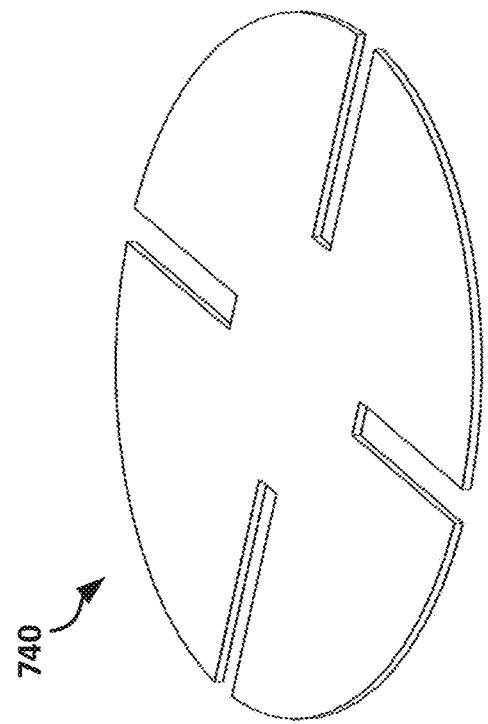
FIG. 9B illustrates, by way of example, a perspective view diagram of an embodiment of a cover of the faraday cage of FIG. 9A.
Figure 9C:
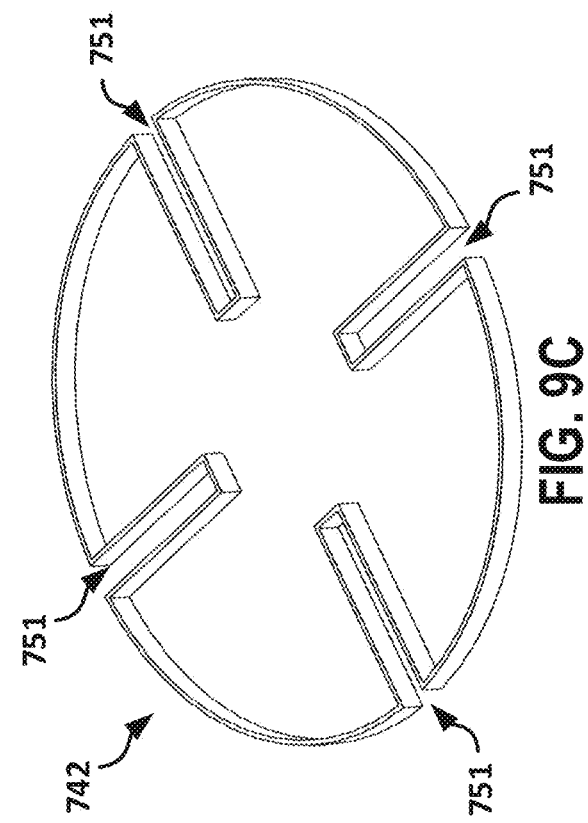
FIG. 9C illustrates, by way of example, a perspective view diagram of an embodiment of a base of the faraday cage of FIG. 9A.

FIG. 8 illustrates, by way of example, a perspective view diagram of an embodiment of the system 700 of FIG. 7. The perspective view shows a cover 740 and a base 742 of the faraday cage 720. FIG. 9A illustrates, by way of example, a perspective view diagram of an embodiment of the faraday cage 720. FIG. 9B illustrates, by way of example, a perspective view diagram of an embodiment of the faraday cage cover 740. FIG. 9C illustrates, by way of example, a perspective view diagram of an embodiment of the faraday cage base 742.

The geometry of the faraday cage cover 740, in one or more embodiments, can accommodate and not interfere with (e.g., can be complementary to, such as to be configured for) a slot pattern of the electromagnetic transmission element. The faraday cage cover 740 can be implemented with a stamped or machined metal plate. Possible materials include copper, steel, or aluminum. The faraday cage cover 740 can be implemented with a solid material, a wire mesh, or a combination thereof.

The faraday cage 720 can be formed by the faraday cage cover 740 which forms a conductive shield above the components while a ground plane 750 (see, e.g., FIG. 11) forms the base of the faraday cage 720, below the components. Vias 730 at the edges of the slots in the faraday cage 720 and on edges of the cage base 742 can help form sides of the faraday cage 720. A fully enclosed cage can effectively be formed between the cover above the components and the layer below the components, such as in the shape of the midfield transmitter pattern.

In the various illustrated embodiments, the faraday cage 720 is provided over or covers various components of control circuitry. In the embodiments shown, the faraday cage 720 is attached to the board 722 using a conductive adhesive, such as solder, conductive paste, electrically conductive tape, or other conductive adhesion mechanism. The board 722 is illustrated as a four-layer board manufactured using a four-layer process, but other board designs can be used, such as can include fewer or more layers. The faraday cage cover 740 is illustrated as being a solid material, but in other embodiments can be mesh or otherwise include one or more holes, perforations, slots or slits therethrough.

Figure 10:
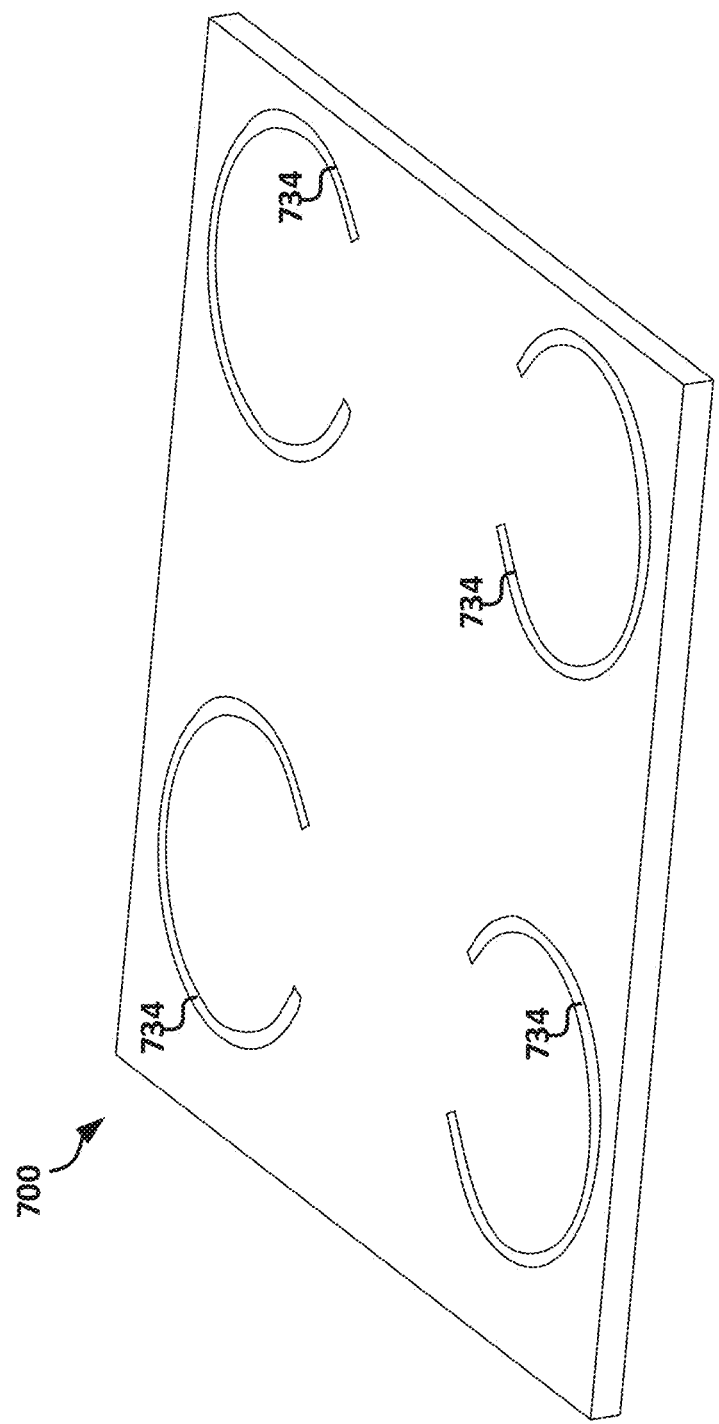
FIG. 10 illustrates, by way of example, a perspective view diagram of an embodiment of the system of FIG. 8 from a back side of the board.

FIG. 10 illustrates, by way of example, a perspective view diagram of the system 700 from an opposite side as that shown in FIG. 8. One or more microstrips or RF slots 734 can excite the transmission element (e.g., the combination of the slots 752 in the ground plane 750 and the faraday cage 720), such as can be used if the pattern were formed with a thicker metal layer. From the RF circuitry perspective, the effective thick slot element allows for wideband enhancement of the electromagnetic transmission element. Electromagnetic energy is transferred to the transmission element, which the faraday cage 720 is a part of, from components (e.g., oscillator, power amplifier, phase compensation circuitry, and so forth) inside the faraday cage 720. One or more vias 732 connects the output of power amplifier from within the faraday cage 720 to the slots 734 of the electromagnetic element outside of the cage, thus transferring electromagnetic energy internal to the faraday cage 720 to the external environment through a via 732. The slots 734 can be open circles or open ellipse shapes, such as shown in FIG. 10. Other shapes can similarly be used, including linear slot features.

In addition, from the perspective of thermal management, the patterned metal plate (faraday cage cover, patterned ground plane, and/or vias) can be used for dissipation of heat. Thermally conductive material such as thermal grease, thermal tape, or thermal epoxy can be used as a thermal conductor between the components inside the faraday cage 720 and the faraday cage base 742 and/or the faraday cage cover 740. The thermal conductor can help radiate heat away from the components inside the cage 720 to the external environment, such as away from a user's body.

FIG. 11 illustrates, by way of example, a perspective view diagram of an embodiment of the second layer 726. The second layer 726 as illustrated includes the ground plane 750 and slots 752 in the ground plane 750. The faraday cage base 742 can include slots 751 therein so as to not interfere with the slots 752.

FIG. 12 illustrates, by way of example, a perspective view diagram of an embodiment of the system 700 with the top layer 724 of the board 722 removed so as to show the alignment of the slots 752 and the slots 751. As can be seen, the slots 751 in the faraday cage base 742 correspond to locations where the slots 752 are present in the second layer 726 (e.g., slot pattern of the electromagnetic transmission element). Thus, the footprint of the faraday cage base 742 does not overlap or is not coincident with any portion of the slots 752 in the embodiments shown. The patterned midfield plate pattern is at the second layer 726 (first internal layer) and is shorted to the faraday cage 720 with one or more vias between the pattern of the electromagnetic transmission element (e.g., midfield coupler) and the faraday cage 720.

Figure 13:
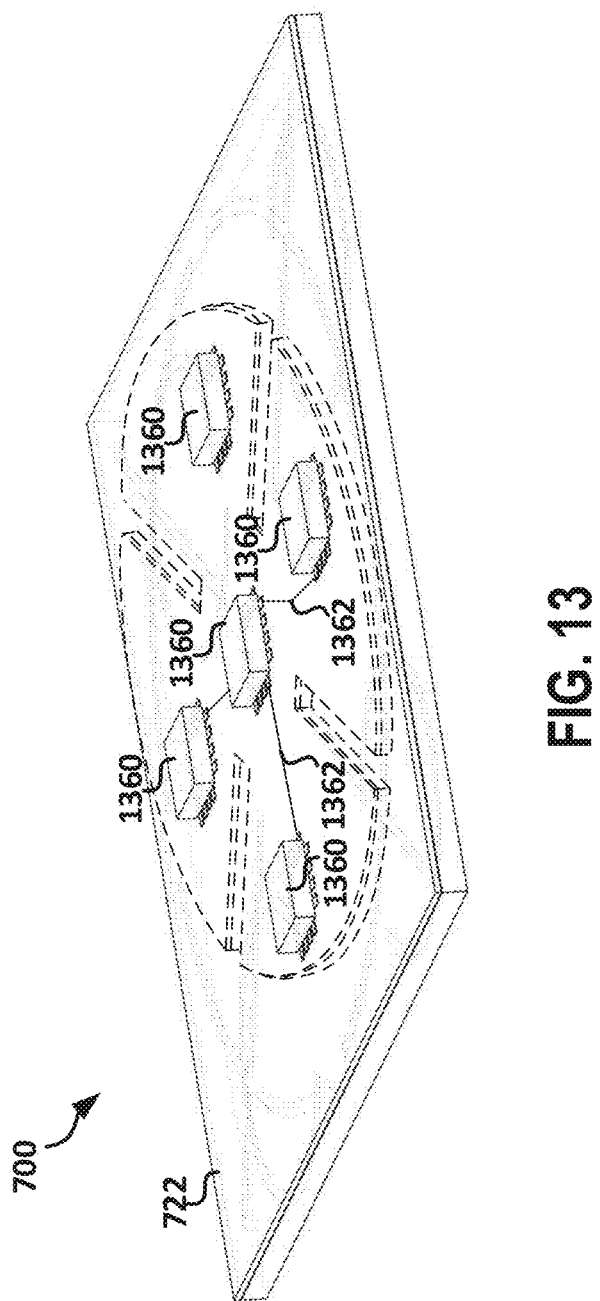
FIG. 13 illustrates, by way of example, a perspective view diagram of an embodiment of a system without a faraday cage cover.

FIG. 13 illustrates, by way of example, a perspective view diagram of an embodiment of the system 700 that includes the faraday cage 720 removed so as to illustrate the discrete components 1360 under the faraday cage cover, in the faraday cage 720, and on the first layer 724. While the components are illustrated as chips, the components can include one or more resistors, capacitors, inductors, integrated circuits, transistors, logic gates, oscillators, state logic components, multiplexers, switches, connectors, or other electrical or electronic components, such as one or more of those in the circuitry of the external device (e.g., the circuitry of the system 400, or other external device circuitry discussed herein). The discrete components 1360 can be electrically connected by one or more traces 1362 on the first layer 724. A thermal paste, grease, or other substance, material, or coating can be situated on and/or around one or more of the discrete components 1360 and/or between the discrete components 1360 and the faraday cage 720, such as to conduct heat away from the components 1360 to the faraday cage cover 740 or faraday cage base 742. The thermal paste or grease can transfer heat from the electrical or electronic components and other elements in contact with or sufficiently near the thermal paste or grease to the faraday cage 720 and subsequently the surrounding environment.

Systems, devices, garments, or other wearable or body-attachable accessories can be configured for positioning and/or retention of an external device near a therapy site. More specifically, described in this subsection are devices, systems, and methods for discrete positioning and/or verification of the positioning of the external device external to the therapy site.

Although considerable progress has been made in the realm of medical device therapy, there still exists a need for comfortable, wearable medical devices that interact with an implanted medical therapy device. A device, or garment or accessory that holds a device at or near the body should be comfortable and relatively unnoticeable to the eye for a better user experience. Various existing form factors for such devices include some that are prohibitively large, such that an individual wearing some types of therapy devices may be uncomfortable and/or embarrassed because the device is noticeable, obtrusive, or interferes with their daily activities.

In an example, a wearable element or garment is configured for a comfortable and/or efficient way of carrying or positioning an external device, such as a source 102, at or near a body or tissue interface, such as near an implantable device 110 that is in wireless power and/or data communication with the source 102. In one or more embodiments, a system includes an implantable sacral neuromodulation device, such as can be implanted in a patient, and can include an implantable communicating element configured to send and/or receive a wireless signal to/from an external device (a wearable device). The external device can include, for example, an antenna, battery, and/or electronics (e.g., control circuitry, such as circuitry of the source 102, antenna 300, or other external device discussed herein). The system can further include a wearable element (e.g., a garment, accessory, clothing, a band, elastic wrap, or other wearable garb) configured to be worn by a user (e.g., a patient) and the external device is coupled to or provided in or retained by the wearable element. The external device can be configured to send and/or receive a wireless signal to communicate with the implantable device. In one or more embodiments, the external device can be placed in multiple locations relative to the wearable element.

The external device can have a variety of configurations. In one or more embodiments, the external device can include an antenna (e.g., a power and/or data transmitter, such as a midfield transmitter) positioned above an S3 foramen and configured to power an implantable device e.g., an implantable neurostimulator). In one or more embodiments, the implantable device can include an internal inductive coil and the external device can include an external inductive coil. The coils can be configured to resonate at substantially the same frequency, such as to maximize power coupling. In an example, the external device can include a location mechanism configured to indicate proper alignment between the external device and the implantable device. The location mechanism may be coupled with or included in the circuitry of the external device.

In one or more embodiments, the system can include a first external device and a second external device that are coupled to one another and are positionable above the S3 foramen. The second external device can be electrically coupled to the first external device. In one or more embodiments, the first external device can be configured to receive data from the implantable device and the second external device can be configured to provide power to the first external device.

The external device can have a variety of configurations. In one or more embodiments, the external device can include a flexible housing or battery adapted to flex in response to motion of a user wearing the flexible battery. In one or more embodiments, the wearable element can be formed from one or a plurality of elastic straps. The wearable element can be adjustable to a variety of patient body sizes and shapes. In still other embodiments, the wearable element can be a belt, pants, shorts, a vest, a sash, an undergarment, or an adhesive patch. In some embodiments, the wearable element can include at least one pocket formed therein. The pocket can be movable or fixed relative to the wearable element. In one or more embodiments, the pocket includes at least one battery disposed therein which is configured to provide power to the external device. Although referred to generally herein as a "pocket", any feature of a wearable element that can position, hold, retain, cover, or enclose all or a portion of an external device can be considered to be a pocket. In some examples, the term "receptacle" is used to refer to a feature that can position, hold, retain, cover, or enclose all or a portion of an external device. The terms pocket and receptacle are not intended to be construed as including or requiring any particular number of sides or walls. For example, a receptacle can include an adhesive, fastener, or other means of attaching a sidewall of an external device to a sidewall of a garment. A receptacle can include a material shelf or lip that facilitates device placement. In other examples, an external device can include or use a clip or other means to fasten the external device to various clothing, garments, or other accessories that can facilitate external device placement or can enhance signal transmission from an external device to an implanted device (e.g., a dielectric member or insert, discussed further herein).

In some examples, the wearable element includes a cloth or fabric assembly that is washable and is configured for repeated use. That is, the wearable element can include a garment similar to traditional clothing or underwear but including a receptacle or other feature to facilitating interfacing the wearable element with an external device. In some examples, the wearable element includes a disposable assembly, such as can be manufactured from various cloth, composite, or other materials. In an example, the wearable element includes a diaper with one or more absorbent materials configured to receive and retain bodily fluids. In an example, the diaper can include one or more features or absorbent structures configured to direct wetness or excrement away from an external device. The wearable element can be made from woven or non-woven fabric, mesh, nylon, or other materials suitable for use in garments, clothes, or other wearable accessories.

Methods are provided for communicating with and powering an implantable/implanted device. The external device can be activated to wirelessly transfer a signal through tissue to the implantable device. For example, the external device can deliver energy to the implantable device and/or receive data from the implantable device. The external device can include an external inductive coil or midfield device. The implantable device can include an internal inductive coil or other electromagnetic signal receiving element. One or more of these elements may be used to transfer a communication signal or to generate power at the implantable device.

Wireless communication can be used to position an external device on or in the wearable element, such as can be worn by a patient at one of a plurality of locations, such as to align the external device with a communicating element on an implanted device. While the external device can be positioned at a variety of locations, in one or more embodiments the external device may be ideally positioned on or over a skin surface in proximity to the implanted device. In an example, a dielectric insert can be provided between the external device and the skin surface to augment or facilitate communication between the external device and the implanted device. The implanted device may send a wireless signal to the external device, such as can include signals indicating information regarding an amount of energy being transferred, acknowledgement of programming signals for or from the external device, and/or malfunction or error warnings. The external device can be configured to communicate to the patient through audio tones, visual displays, or vibration. This can be used to help guide the patient to place and/or secure the external device at a location that is sufficient or even ideal for wireless power transfer. The external device may communicate information about a battery level of the external device in addition to other device status information to the user. This may help a patient understand when to change or charge a battery of the external device.

The external device can be positioned on or in the wearable element or at a distance apart from the wearable element. For example, the wearable element can include a plurality of flexible straps, and the external device can be removably mated to the flexible straps, such as in proximity to the implantable device. Additionally, or alternatively, the external device can be disposed within a pocket affixed to the wearable element. In one or more embodiments, the wearable element can include a flexible battery. The external device can be coupled to the flexible battery and can deliver energy to the implantable device, such as energy that originated at the flexible battery.

FIG. 14A illustrates, by way of example, an embodiment of a system 1400A for communication of one or more signals between an implanted device 1404 and an external device 1402. The implanted device 1404 can be similar to or the same as any of the implantable devices discussed herein, such as the implantable device 110, or other implantable device. The external device 1402 can be similar to or the same as any of the external devices discussed herein, such as the source 102, the antenna 300, or the like. The external device 1402 can be situated in and/or affixed at a position within a pocket 1406. The implanted device 1404 can be implanted under the surface a user's skin, such as to be internal to a user's body 1410. The external device 1402 can transfer power and/or data to the implanted device 1404. In one or more embodiments, the external device 1402 is positioned in a sleeve or other affixation or retention feature of a wearable garment. In an example, the system 1400A includes a dielectric member 1403 provided between the external device 1402 and the user's body 1410 or tissue surface.

The pocket 1406 can be internal to, or coupled to, a wearable element 1408, such as an undergarment, pants, shirt, panty hose, shorts, bodysuit, wearable elastic band, and so forth. In the example of FIG. 14A, the pocket 1406 is drawn using dashed lines to indicate the boundaries of the pocket 1406. In various embodiments, boundaries of the pocket 1406 or other receptacle can be fixed or adjustable, and can be configured to accommodate one or several different types of external devices. The boundaries or walls of the pocket 1406 can be rigid or compliant (e.g., elastic), and can be configured to receive and retain the external device 1402 in a particular location relative to other portions or features of the wearable element 1408. For example, when the wearable element 1408 includes an underwear or underpants garment, the pocket 1406 can be provided in a fixed location relative to an elastic waistband or to leg holes of the garment. A position of the pocket 1406 relative to one or more of the other features of the wearable element 1408 can depend on, or can be related to, an overall size of the wearable element 1408, as further discussed herein.

In an example, the dielectric member 1403 is configured to facilitate or enhance wireless communication between the external device 1402 and the implanted device 1404. The dielectric member 1403 can include a material having a dielectric or relative permittivity characteristic that is the same or similar to that of air (e.g., having a K value of approximately 1). In an example, relative permittivity of the dielectric member 1403 is the same or similar to that of air at one or more particular frequencies or frequency bands of interest. For example, a frequency band of interest can include a band from about 300 MHz to about 5 GHz.

In an example, the dielectric member 1403 includes or comprises one or more of a polychloroprene rubber (e.g., neoprene), a urethane (e.g., PORON MSRS), a foam, or other natural or composite material, generally provided in a sheet, rectangular cuboid, cylindrical, or other shape having non-negligible width, height, and depth or length dimensions. Generally, the dielectric member 1403 has low thermal conductivity and is resistant to mild acids and bases.

The dielectric member 1403 can be elastic or compressible to enhance user comfort when a garment comprising the dielectric member 1403 is worn. A dielectric characteristic (e.g., relative permittivity value) can be substantially unchanged when the member is in compressed and uncompressed (e.g., relaxed) states. In an example, the dielectric member 1403 can receive a first force or pressure over a first area on a first side of the member and distribute the force or pressure over a greater second area on at least a second side of the member, such as to enhance user comfort.

In an example, the dielectric member 1403 is configured to provide an effect similar to an airgap between the external device 1402 and the tissue, or tissue interface, of the user. The dielectric member 1403 can have a relative permittivity characteristic that is less than a relative permittivity of a substrate of the source, is less than a relative permittivity of a housing that encloses the source, and is less than a relative permittivity of tissue at the tissue interface (e.g., tissue in which the implanted device 1404 is implanted). The dielectric member 1403 so configured provides a tunneling effect for energy provided by the external device 1402, and avoids a strong coupling between the tissue itself and the external device 1402. In other words, instead of providing a matching layer that enhances coupling between the external device 1402 and the tissue in which the implanted device 1404 is implanted, the dielectric member 1403 is configured to provide a relative permittivity mismatch at the tissue interface, which in turn facilitates energy tunneling from the midfield external device 1402 to the implanted device 1404.

Figure 14B:
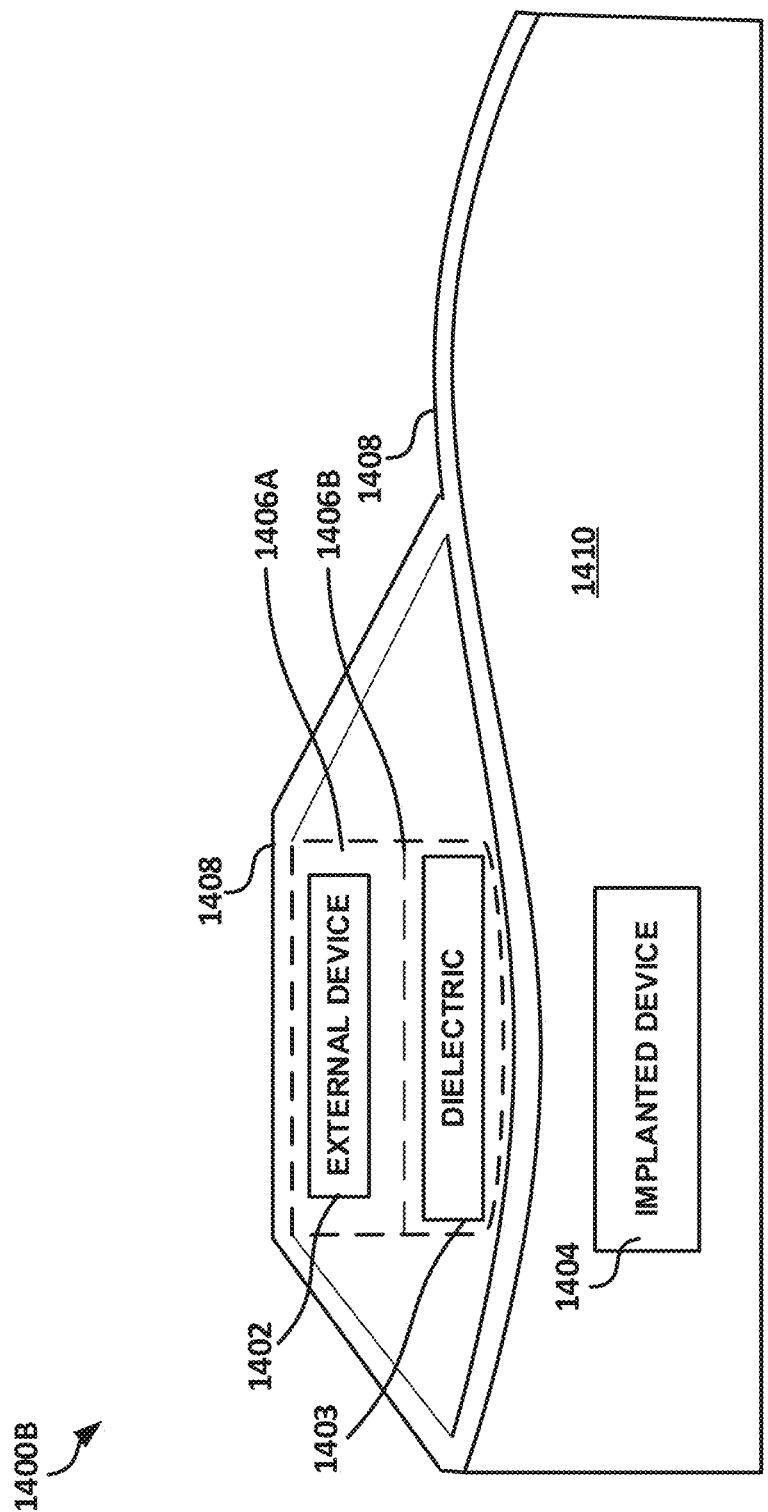
FIG. 14B illustrates, by way of example, a block diagram of an embodiment of a system for locating an external source device relative to an implanted device.

In the example of FIG. 14A, the dielectric member 1403 and the external device 1402 are co-located in a common cavity of the pocket 1406. FIG. 14B illustrates, by way of example, an embodiment of a system 1400B for communication of one or more signals between the implanted device 1404 and the external device 1402. The system 14009 includes first and second receptacles 1406A and 1406B. The first and second receptacles 1406A and 1406B can be affixed or attached to a common wearable element 1408. In the example of FIG. 14B, the first receptacle 1406A is configured to receive the external device 1402 and the second receptacle 1406B is configured to receive the dielectric member 1403. A sidewall (e.g., comprising one or more of the same materials as used in the constructions of the wearable element 1408, or a different material) can be provided between the first and second receptacles 1406A and 1406B, for example, to facilitate better or more accurate placement of each of the external device 1402 and the dielectric member 1403 relative to the wearable element 1408 and therefore to the body 1410. In other words, the first and second receptacles 1406A and 1406B can share a common sidewall. The size, shape, and volume of each of the first and second receptacles 1406A and 1406B can be the same or different; generally, dimensions or elasticity characteristics of the one or more receptacles can be selected or configured according to the device and/or dielectric member that is intended for use therein.

In an example, one or more materials that comprise the wearable element 1408 and the pocket (e.g., the pocket 1406, and/or the first or second receptacles 1406A or 1406B) can have a dielectric characteristic or relative permittivity that is the same or different than a permittivity characteristic of the dielectric member 1403. In an example, different portions of the wearable element 1408 can comprise different materials having respective different permittivity characteristics. For example, a portion of the wearable element 1408 configured for placement between the dielectric member 1403 and the user's body 1410 can include a material having a relative permittivity characteristic that is substantially the same as the permittivity of the dielectric member 1403.

Various other benefits can be realized when the external device 1402 is used together with the dielectric member 1403. For example, the dielectric member 1403 can provide thermal insulation between the user's body 1410 and the external device 1402. Thus heat generated by the external device 1402 can be inhibited from reaching the user's body 1410. In some examples, a garment configured to hold the external device 1402 and/or the dielectric member 1403 can be configured to sink heat away from the external device 1402 to additionally shunt heat away from the user's body 1410.

The dielectric member 1403 can have a height characteristic (e.g., a thickness) that is configured to provide a specified minimum separation distance or standoff between the external device 1402 and a tissue interface of the user's body 1410. In an example, the minimum separation distance is about 2 mm. The specified minimum separation distance can be selected to reduce loading on a transmission antenna of the external device 1402, and thereby enhance or improve the longevity of the external device 1402 per charge. In other words, the separation distance between the external device 1402 and a tissue interface can be tuned or selected to avoid exceeding a defined maximum loading condition of a transmission antenna of the external device 1402. Loading of the transmission antenna can be a function of, among other things, operating frequency, which can be separately or additionally tuned by circuitry on the external device 1402. For example, see discussion of the various tuning circuitry and/or tuning features, such as including capacitive tuning elements, in PCT Application No. PCT/US2018/016051, filed on Jan. 30, 2018, and titled "MIDFIELD TRANSMITTER AND RECEIVER SYSTEMS", which is incorporated herein by reference in its entirety.

In an example, the specified minimum separation distance can be selected to reduce a rate at which electromagnetic energy is absorbed by tissue, that is, by the user's body 1410, such as at or near the tissue interface. In other words, the dielectric member 1403 can help reduce a specific absorption rate at the user's body 1410 from energy originating from the external device 1402. In some embodiments, a specific absorption rate can be sufficiently low that no additional standoff is needed or desired.

FIG. 15 illustrates, by way of example, a back view diagram of a portion of a human body 1500, such as including the user's body 1410, multiple potential placement locations for the external device 1402, and corresponding areas which the pocket 1406 can cover. In an example, the external device 1402 can be placed in the pocket 1406 at or near a position of an S3 foramen, such as can be about 9-10 centimeter from the tip of a coccyx or sciatic notch and/or about two centimeters to the left or the right of a midline of the human body (indicated by a dashed line 1502). One or more of the wearable elements or garments discussed herein can be configured to position an external device 1402 at or near an S3 foramen when the element or garment is worn by a user.

In an example, a location of the pocket 1406 can be determined based on a particular feature or set of features of the wearable element 1408 and/or a user body type. In the example of FIG. 15, the wearable element 1408 includes an underpants-style garment, and a top edge of the pocket 1406 is provided at a distance D1 below a top edge of a waistband of the garment. In an example, a magnitude of the distance D1 can be changed depending on a size of the garment. For example, as a user body size increases and therefore a size of the garment increases, a target location (e.g., at or near the S3 foramen) can be relatively further from a waistband of an underwear garment. That is, as a user body size and garment size increase, a distance from a top edge of the larger garment's waistband to the pocket 1406 can correspondingly increase to thereby provide optimized external device placement for different user body types. Other landmarks than a top edge of a waistband can similarly be used, for example, a distance from a lateral side edge of a garment, a distance from a crotch or leg opening feature of a garment, among other fiducials, can similarly be used. Fiducial-based landmarking or pocket localization relative to other garment or user body features can similarly be used with garments other than underwear-style garments.

In an example, the wearable element 1408 is configured to be elastic or stretchable in one or more directions, and can be configured to restrict or resist stretching in another direction. During use when the wearable element 1408 is an underpants-style garment, for example, an external device 1402 in the pocket 1406 tends to migrate or shift primarily in a vertical direction (the vertical direction corresponding to a height direction of a user). To help counteract the vertical location change, at least one of the constituent materials of the wearable element 1408 can restrict or resist stretching in the vertical direction.

FIG. 16 illustrates, by way of example, a perspective view diagram of a human body 1600. The body 1600 as illustrated includes a form-fitting embodiment of the wearable element 1408 with the pocket 1406 for housing the external device 1402. The pocket 1406 as illustrated spans at least two potential locations for placement of the eternal device 1402. The pocket 1406, in one or more embodiments, may be narrower (in terms of its width relative to the width of the human body), such as to cover only a single potential location of the external device 1402. However, configuring the pocket 1406 to span two or more locations allows for a single pocket to accommodate a wider variety of external device locations.

Figure 17:
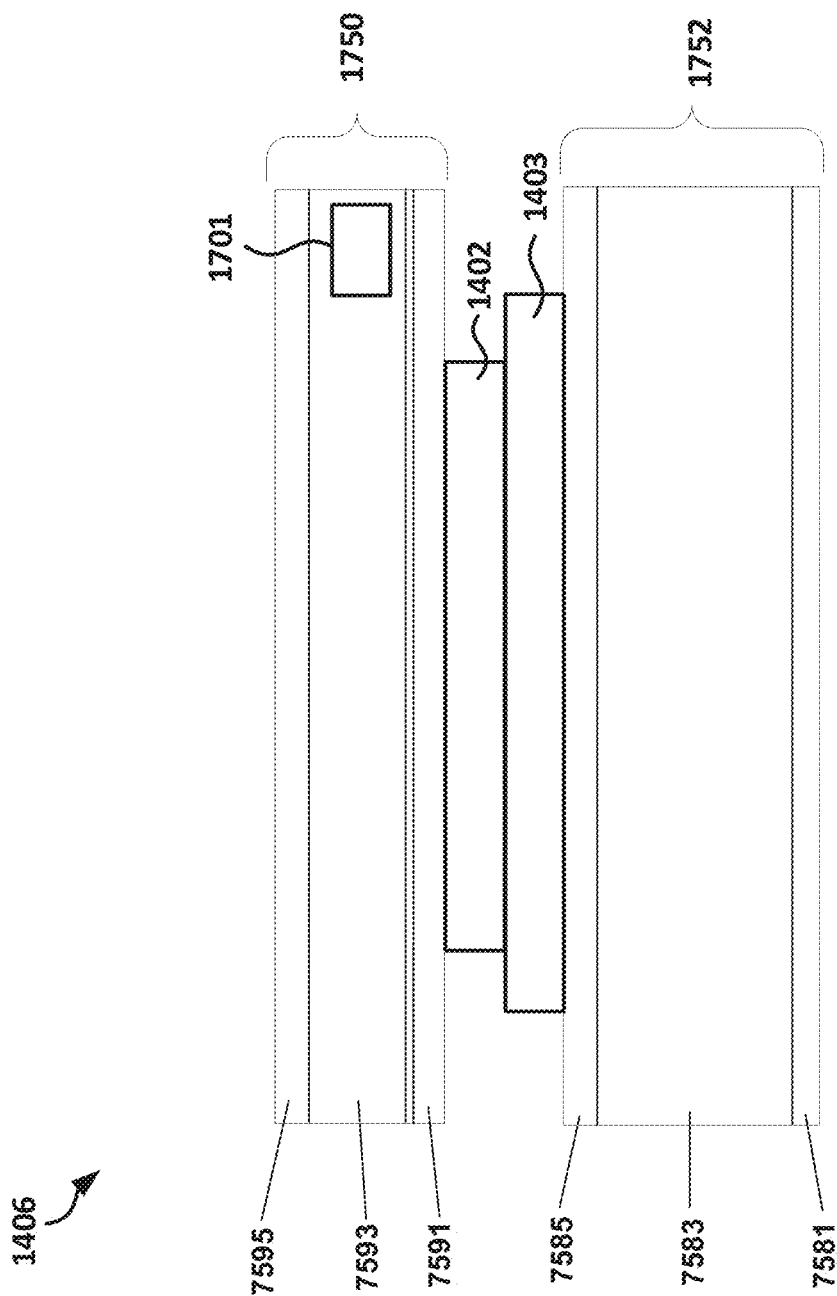
FIG. 17 illustrates, by way of example, a block diagram of an embodiment of layers of a pocket.

FIG. 17 illustrates, by way of example, an exploded view diagram of a portion of FIG. 14A that includes the pocket 1406 and the external device 1402. The pocket 1406 is illustrated as including a top pocket layer 1750 and a bottom pocket layer 1752. The top pocket layer 1750 is sometimes referred to as the "top layers". The bottom pocket layer 1752 is sometimes referred to as the "bottom layers". Note that the illustration of FIG. 17 can correspond to the layers of a sleeve as well. Each of the top and bottom pocket layers 1750 and 1752 are illustrated as including three fabric layers, however, each of the top and bottom pocket layers 1750 and 1752 may include fewer or additional fabric layers. The pocket 1406 is thus illustrated as including six layers and the device 1402 is illustrated as being situated between layer 3 and layer 4 of the pocket. Note that the pocket 1406 may include fewer or more layers, depending on the application to be accommodated. As illustrated, the bottom pocket layer 1752 includes three layers, 7581 ("Layer 1"), 7583 ("Layer 2"), and 7585 ("Layer 3"). As illustrated the top pocket layer 1750 includes three layers, 7591 ("Layer 4"), 7593 ("Layer 5"), and 7595 ("Layer 6").

The Layer 1 of the pocket can include a soft, supple, and/or compliant material. This layer is closest to the user's skin and can provide comfort. The Layer 2 and/or Layer 3 can be insulating material(s) (e.g., materials that resist heat passing therethrough) and/or waterproof or water resistant, respectively. This heat insulating property of the material can help protect a user's skin from heat produced by the external device 1402 and deflect heat towards the top pocket layer 1750. The waterproof/water resistant property can help prevent moisture from travelling to the user's skin and help transport any such moisture towards the top layer(s). In one or more embodiments, one or more of the bottom pocket layer 1752 may be water wicking so as to transport water away from the user's skin towards the top layer(s).

One or more of the top layer(s) Layer 4, Layer 5, and/or Layer 6 may be a heat conductive material, such as to transport heat away from the user's body. In an example, one or more of the layers includes thermally conductive fabric or thermally conductive threads configured to sink heat away from the external device 1402. One or more of the top layer(s) Layer 4, Layer 5, and/or Layer 6 may be compressive, such as to help ensure that the wearable element does not slip or otherwise move on the user's body and to help keep the external device positioned in a location at which it can communicate with the implantable/implanted device.

The wearable element can include a pocket or pockets in undergarments that can include one or more top and one or more bottom layers. As previously discussed, Layer 1 can be a soft breathable material, such as polyester. This layer can be in direct contact with the skin. Layer 2 and/or Layer 3 can be made out of an insulating material. Layer 3 can be neoprene, Gore-Tex, Outlast, or other material that includes a low thermal conductivity, such as a material similar to neoprene. Layer 2 and/or 3 may completely prevent the penetration and/or absorption of liquid water (waterproof). Layers 2 and 3 can be the same material. Layer 2 and/or Layer 3, (the inside layer to the pocket, closest to the body) can include a one-way permeable material, such as GORE- TEX®, GORE WINDSTOPPER® membrane, polytetrafluoroethylene (ePTFE), hemp, sheep's wool, cotton, straw, aerogel, polyurethane, or the like.

In an example, one or more of the Layers 1-6 can be combined or made of the same or similar materials. For example, one or more of the layers in contact with or adjacent to the skin can include or comprise a dielectric member made of a material having a dielectric permittivity or relative permittivity that is the same or similar to that of ambient air (e.g., K approximately equal to 1). In an example, Layer 2 (7583 in FIG. 17) comprises a dielectric portion having a specified relative permittivity characteristic, and Layers 1 and 3 are provided at opposites side of Layer 2 to enhance user comfort, such as by providing a soft or compliant member for Layer 1 adjacent to the user's skin. In an example, the dielectric is made from neoprene, however, other materials having similar relative permittivity characteristics can be used.

The pocket can be ventilated to allow heat to dissipate, sometimes referred to as breathable. Layer 4 and/or layer 6 can include a breathable material that can allow the release of heat through the top (the side away from the user's body). The top of the pocket can include a breathable material. The sides of the pocket can include a breathable and/or waterproof material.

Insulating materials can include, for example, one or more of: polyurethane foam, PYROGEL® XT, GORE-TEX®, GORE WINDSTOPPER® membrane, polytetrafluoroethylene (ePTFE), hemp, sheep's wool, cotton, straw, aerogel, polyurethane, a material with a high R-value, Outlast, or the like.

In an example, a verification device 1701 can be coupled to or embedded in a portion of the wearable element 1408. The verification device 1701 can be a mechanical or electrical device configured to communicate with the external device 1402. When the external device 1402 receives a signal or mechanical unlocking from the verification device 1701, then one or more functions or features of the external device 1402 can be made available to a user. In an example, the verification device 1701 includes one of an RFID tag and RFID reader, and the external device 1402 comprises the other one of the RFID tag and RFID reader. When the reader identifies and verifies an acceptable tag, then the reader can enable one or more functions on the external device 1402. The verification device 1701 can help ensure that the external device 1402 is used together with a genuine or intended wearable element 1408, for example to ensure a proper or more accurate placement of the external device 1402. Although the example of FIG. 17 shows the verification device 1701 in proximity to the pocket 1406, the verification device 1701 can be provided elsewhere in or on the wearable element 1408.

In an example, the verification device 1701 can include a sensor or other device that is configured to sense or determine when or whether the wearable element 1408 is being worn (e.g., correctly worn) by a user. In some examples, the verification device 1701 includes or uses an accelerometer, gyroscope, or other position sensor device, and can optionally include a state machine or other processor circuit configured to monitor information from the verification device 1701 and provide a status determination about the wearable element 1408. The status determination can include, among other things, an indication of whether the wearable element 1408 is being worn by a user and whether the wearable element 1408 is being correctly worn. In an example, the external device 1402 can be enabled only when the verification device 1701 indicates that the wearable element 1408, and therefore its appurtenant external device 1402, is correctly worn by a user. Enabling or inhibiting one or more functions of the external device 1402, and correspondingly enabling or inhibiting one or more functions of an implanted device 1404, can help modulate a therapy in a way that can be beneficial to a user.

For example, when the implanted device 1404 is implanted and configured to treat overactive bladder, it can be beneficial to the user that stimulation from the implanted device 1404 is interrupted or inhibited when the user has a full bladder or wants to urinate. If the external device 1402 is provided in or coupled to an underpants garment, then the external device 1402 can be moved away from its intended position when the user goes to urinate or defecate (e.g., because the user must remove his or her pants), and therefore communication between the external device 1402 and the implanted device 1404 can be interrupted. Such an interruption can cause the implanted device 1404 to halt therapy delivery. With therapy halted, the user can urinate more completely and effectively. In an example, the implanted device 1404 can be configured to provide a stimulation therapy only when (1) the wearable element 1408 is properly worn by a user (such as can be optionally verified using the verification device 1701), (2) a receptacle or pocket of the wearable element 1408 includes the external device 1402 (such as can be optionally verified using the verification device 1701), and (3) the external device 1402 actively communicates power and/or data to the implanted device 1404.

In an example, one or more of the implanted device 1404, the external device 1402, the verification device 1701, or other sensors or circuitry in communication with one or more of the implanted device 1404, external device 1402, and the verification device 1701, can be configured to determine whether a user voiding event is likely or is about to occur. For example, information from an accelerometer can be used to determine whether a user is sitting or if the user recently transitioned from standing to seated posture. In an example, information from an accelerometer coupled to the wearable element 1408 can be used to determine whether a donning or doffing of the wearable element 1408 occurred or is occurring. Such acceleration patterns can be learned or can be configured during a calibration or setup. In an example, information from a timer circuit can be used to determine that a voiding event is likely to occur. In an example, a user can provide information to the external device 1402 via an interface device about when or whether the user intends to urinate, or about a user perception of a bladder fullness or urge to urinate. In an example, one or more invasive sensors (e.g., bladder fullness sensors) can be used to provide information about whether a user voiding event is likely or is about to occur.

FIGS. 18A-18D illustrate generally examples of portions of a method that can include enhancing a voiding efficiency for a user. The examples of FIGS. 18A-18D can include a method for controlling delivery of neural stimulation therapy using a system that includes an implanted midfield device, such as the implanted device 1404, and an external midfield transmitter device, such as the external device 1402. The external midfield transmitter device can include one or more structures excitable to manipulate evanescent fields outside of tissue to generate a propagating and focused field in the tissue and thereby communicate power and/or data signals to the implanted midfield device. The implanted midfield device includes one or more electrodes for delivering an electrostimulation therapy to a neural target, and the delivered therapy can use, at least in part, energy received from the external midfield transmitter device.

Figure 18A:
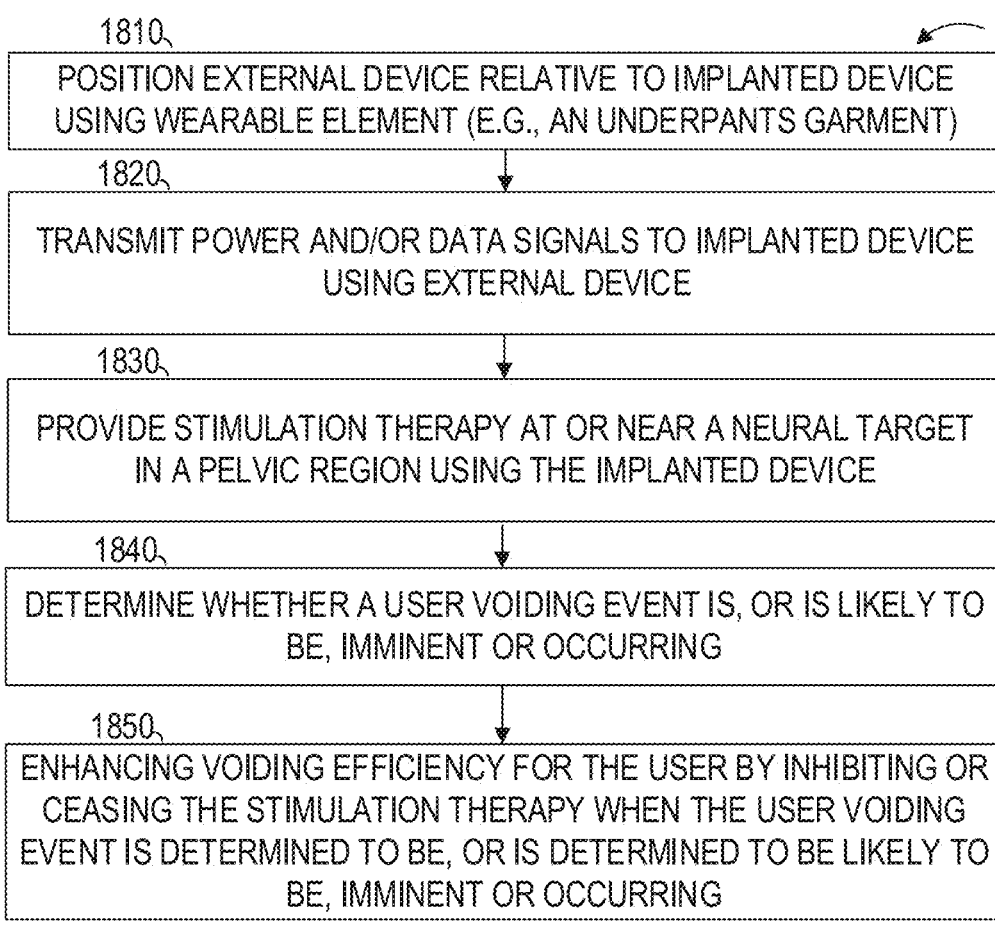
FIG. 18A illustrates, by way of example, a method that includes enhancing a user voiding efficiency.

FIG. 18A illustrates a first method 1800A that includes enhancing a voiding efficiency for a user by adjusting a therapy provided by the implanted device 1404 based on information about a user voiding or bladder characteristic. At operation 1810, the example can include positioning the external device 1402 at or near a tissue interface and the implant midfield device using a wearable element or garment, such as using one of the wearable elements or garments discussed herein. In an example, the wearable element includes an underwear or underpants-style garment that is configured to locate the external device 1402 in or near a pelvic region of a user.

At operation 1820, the example can include transmitting midfield power and/or data signals from the external device 1402 to the implanted device 1404. The operation 1820 can include generating and providing the same or different electrical drive signals to respective features e.g., sub-wavelength features) of the external device 1402 to manipulate evanescent fields outside of the user's body tissue and thereby generate a propagating and focused (e.g., steered) field inside the user's body tissue, such as to target signal transmission toward the implanted device 1404. At operation 1830, the implanted device 1404 can provide a stimulation therapy at or near a neural target using, at least in part, energy received from the external device 1402. In an example, the neural target is in a pelvic region of the user.

At operation 1840, the example can include determining whether a user voiding event is, or is likely to be, imminent or occurring for the user. In an example, a control circuit at the external device 1402, at the implanted device 1404, or located elsewhere e.g., in a remote device in communication with the external device 1402) can use information from a user and/or from one or more sensors, timers, state machines, or other circuit or circuits, to make a determination about whether the user voiding event is, or is likely to be, imminent or occurring.

At operation 1850, the example can include using the determination about the user voiding event from operation 1840 to enhance or improve a voiding efficiency for the user. In an example, operation 1850 includes inhibiting or ceasing a stimulation therapy provided by the implanted device 1404 to the neural target when the voiding event is determined to be, or is determined to be likely to be, imminent or occurring for the patient. The therapy can be resumed automatically, such as following a specified duration without providing the therapy, or the therapy can be resumed in response to receiving an indication that the voiding event is completed. The indication that the voiding event is completed can be provided using the same or different information from the user and/or from the one or more sensors, timers, state machines, or other circuit or circuits.

Figure 18B:
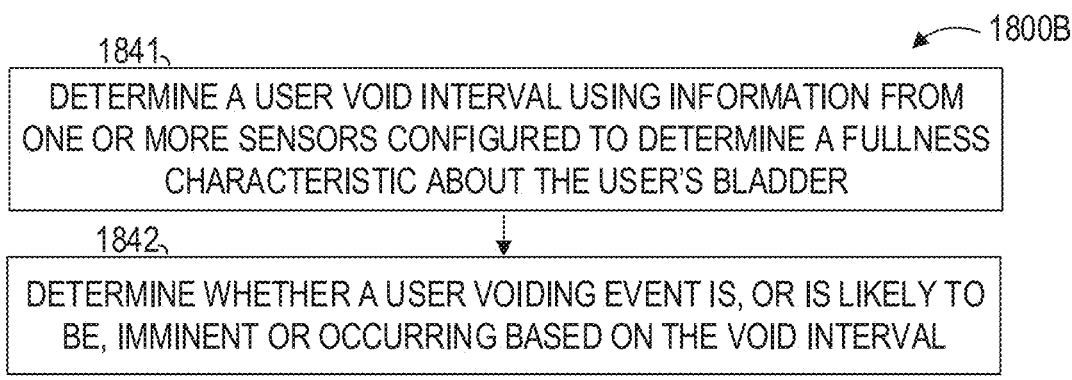
FIG. 18B illustrates, by way of example, a method that includes determining whether a user voiding event is, or is likely to be, imminent or occurring based on a determined user void interval.
Figure 18C:
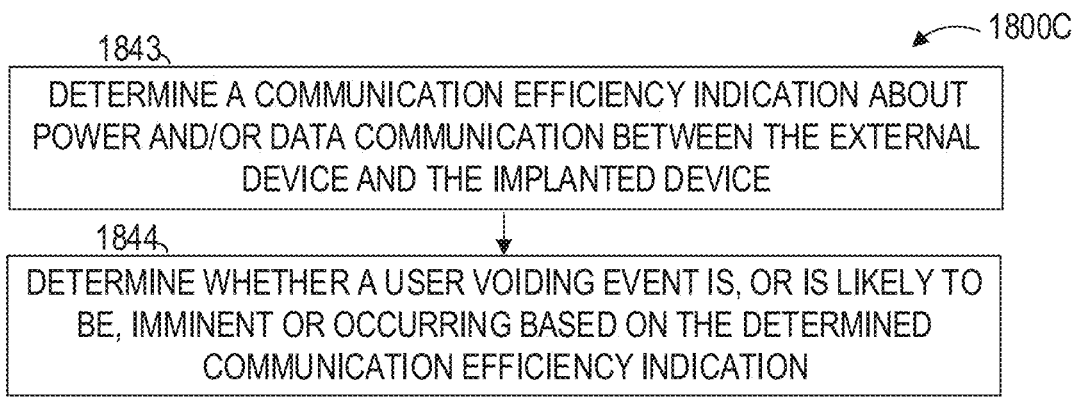
FIG. 18C illustrates, by way of example, a method that includes determining whether a user voiding event is, or is likely to be, imminent or occurring based on a communication efficiency characteristic.
Figure 18D:
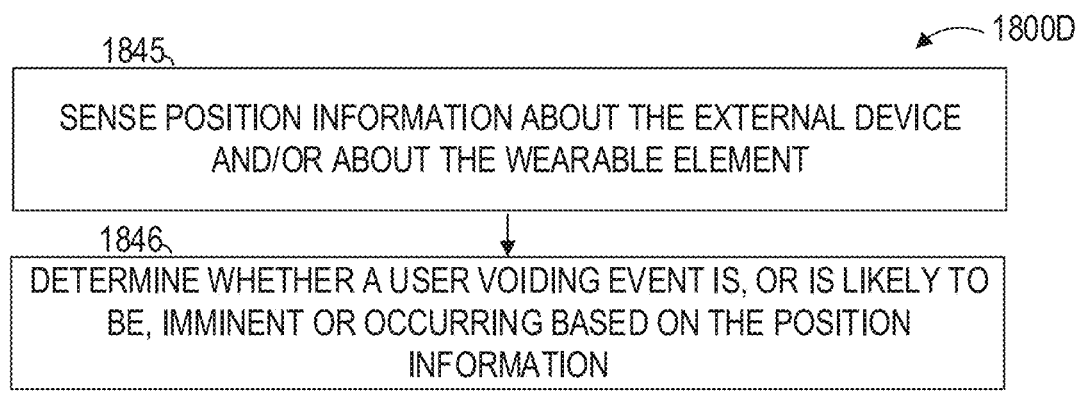
FIG. 18D illustrates, by way of example, a method that includes determining whether a user voiding event is, or is likely to be, imminent or occurring based on position information about an external device.

The operations of FIGS. 18B-18D can optionally be combined, or any one or more of the operations can be used together with the operations of FIG. 18A. FIG. 18B illustrates generally an example of a portion of a method 1800B that includes determining whether the user voiding event is, or is likely to be, imminent or occurring (e.g., corresponding to operation 1840 from the example of FIG. 18A). At operation 1841, the example can include determining a user void interval or void frequency. The void interval or void frequency can represent a duration, or expected duration, between times when the user urinates or defecates. A processor in one or more of the external device 1402, the implanted device 1404, or elsewhere (e.g., in a remote device in communication with the external device 1402) can be used to determine the user void interval. In an example, the operation 1841 includes using information from one or more physiologic sensors (e.g., coupled to a processor) to determine a fullness characteristic about the user's bladder. The physiologic sensors can include one or more internal or external sensors. In an example, the operation 1841 includes using subjective information input by the user about a sensation or feeling of bladder fullness or urge to urinate. At operation 1842, the example can include determining whether the user voiding event is, or is likely to be, imminent or occurring based on the void interval as determined at operation 1841.

FIG. 18C illustrates generally an example of a portion of a method 1800C that includes determining whether the user voiding event is, or is likely to be, imminent or occurring (e.g., corresponding to operation 1840 from the example of FIG. 18A). At operation 1843, the example can include determining a communication efficiency indication about wireless communication between the external device 1402 and the implanted device 1404. In an example, the communication efficiency indication is a measure of a quality of a received signal at the implanted device 1404 relative to a signal emitted by the external device 1402. In an example, when the efficiency indication is at or above a specified threshold efficiency value, then the implanted device 1404 can be configured to carry out therapy delivery. When the efficiency indication falls below the specified threshold efficiency value, then the implanted device 1404 can be configured to interrupt, halt, or change therapy delivery. In an example, information about communication efficiency between the external device 1402 and the implanted device 1404 can be determined at least in part using a backscatter signal (see, e.g., the discussion about the backscatter signal 112, above).

When the external device 1402 is shifted slightly away from an intended use position at a tissue interface near the implanted device 1404, the external device 1402 can update one or more phase or other parameters to help steer or shift a field generated by the external device 1402, such as to attempt to maintain or establish communication that exceeds a minimum efficiency threshold. However, when the external device 1402 is removed from the tissue interface, the implanted device 1404 can identify a loss of communication (e.g., power), and interrupt, halt, or change a therapy. In an example, the external device 1402 is configured for use with one or more of the wearable elements discussed herein. When the wearable element is removed from the user's body, then the external device 1402 is correspondingly removed from a tissue interface and therapy provided by the implanted device 1404 can be interrupted.

At operation 1844, the method 1800C can include determining whether a user voiding event is, or is likely to be, imminent or occurring based on the determined communication efficiency indication. For example, the wearable element 1408 can include an underpants-style garment and the external device 1402 can be coupled with the garment. When a user removes the underpants-style garment, and therefore also removes the external device 1402 that is coupled to the garment, then circuitry of the external device 1402 and/or of the implanted device 1404 can be configured to recognize the communication interruption and, in turn, assume or determine whether the user is, or is likely to be, attempting to urinate or defecate. The circuitry can use information from one or more other sensors, timers, information from the user, or other device to help make the determination. For example, information about a time of day, information particular to the user about void habits or frequency, or information from one or more other sensors can be used together to help inform the determination made at operation 1844. In an example, a state machine or other processor can receive the information about the communication efficiency and/or information from the one or more other sensors or circuitry and in response provide the determination at operation 1844.

FIG. 18D illustrates generally an example of a portion of a method 1800D that includes determining whether the user voiding event is, or is likely to be, imminent or occurring (e.g., corresponding to operation 1840 from the example of FIG. 18A). At operation 1845, the example can include sensing position information about the external device 1402 and/or about the wearable element 1408, such as a wearable element that includes or is coupled to the external device 1402. In an example, sensing the position information about the external device 1402 can include receiving or determining position information from an accelerometer, gyroscope, proximity sensor, or other sensor, such as can be coupled to the external device 1402 or to the wearable element 1408 that is coupled to the external device 1402.

At operation 1846, the method 1800D can include determining whether a user voiding event is, or is likely to be, imminent or occurring based on the sensed position information from operation 1845. For example, the wearable element 1408 can include an underpants-style garment and the external device 1402 can be coupled with the garment. When a user removes the underpants-style garment, and therefore also removes the external device 1402 that is coupled to the garment, then circuitry of the external device 1402 and/or of the implanted device 1404 can be configured to recognize the position change and, in turn, assume or determine whether the user is, or is likely to be, attempting to urinate or defecate. The circuitry can use information from one or more other sensors, timers, information from the user, or other device to help make the determination. For example, information about a time of day, information particular to the user about void habits or frequency, or information from one or more other sensors can be used together to help inform the determination made at operation 1846. In an example, a state machine or other processor can receive the position information about the external device 1402 and/or information from the one or more other sensors or circuitry and in response provide the determination at operation 1846.

Figure 19B:
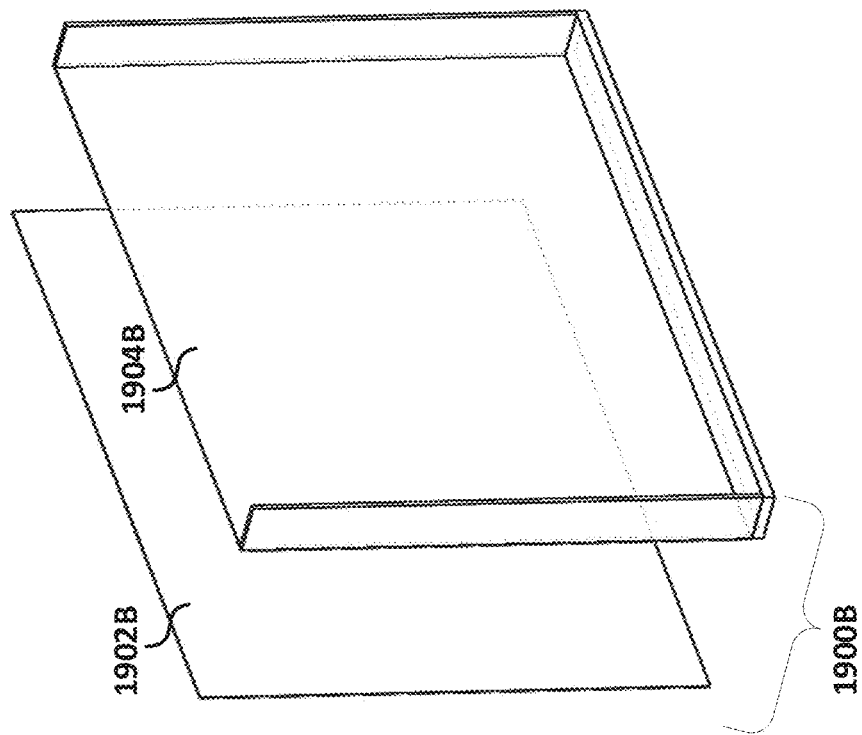
FIG. 19B illustrates, by way of example, a diagram of layers of a pocket assembly.
Figure 19A:
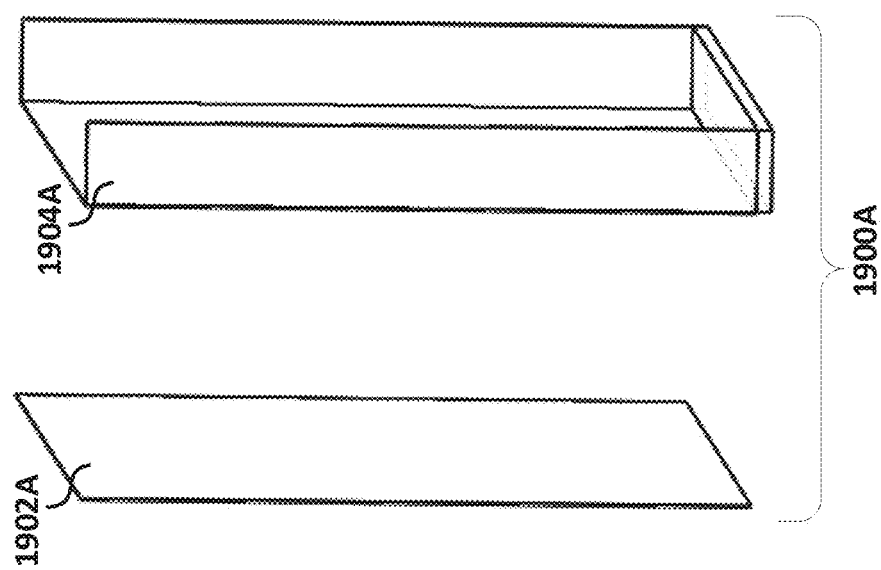
FIG. 19A illustrates, by way of example, a diagram of layers of a pocket assembly.

FIG. 19A illustrates, by way of example, a perspective view diagram of an embodiment of bottom layers 1900A of the pocket 1406. FIG. 19B illustrates, by way of example, a perspective view diagram of another embodiment of bottom layers 1900B of the pocket 1406. The bottom layers 1900B are similar to the bottom layers 1900A with the bottom layers 1900B covering multiple potential implant locations (one on each side of the spinus tubercles, for example) and the bottom layers 1900A covering one such potential location. The bottom layers 1900A as illustrated include a first bottom layer 1902A and a second bottom layer 1904A. The first bottom layer 1902A can be closer to a user's body than the second bottom layer 1904A when the layers 1900A are worn. The layers 1902A and 1904A can be affixed to each other, such as by thread, adhesive, heat-bonding, or other affixing means. The layers 1902B and 1904B are similar to the layers 1902A and 1904A, respectively, with the layers 1902B and 1904B being wider than the layers 1902A and 1904A as previously discussed.

Figure 20:
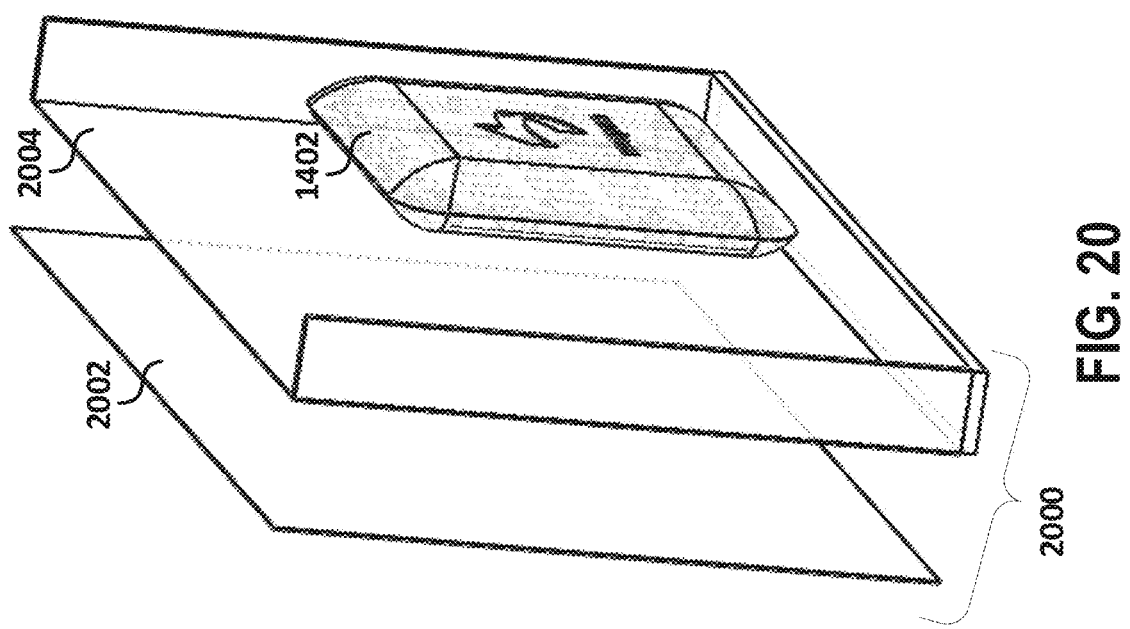
FIG. 20 illustrates, by way of example, a perspective view diagram of the embodiment of the layers of FIG. 19A with an external device situated by the layers.

FIG. 20 illustrates, by way of example, a perspective view diagram of the embodiment of bottom layers 2000, such as is similar to the layers 1900 of FIG. 19, with the external device 1402 attached to the inner most layer (layer 2004 of the bottom layers 2000 of FIG. 19).

Figure 21:
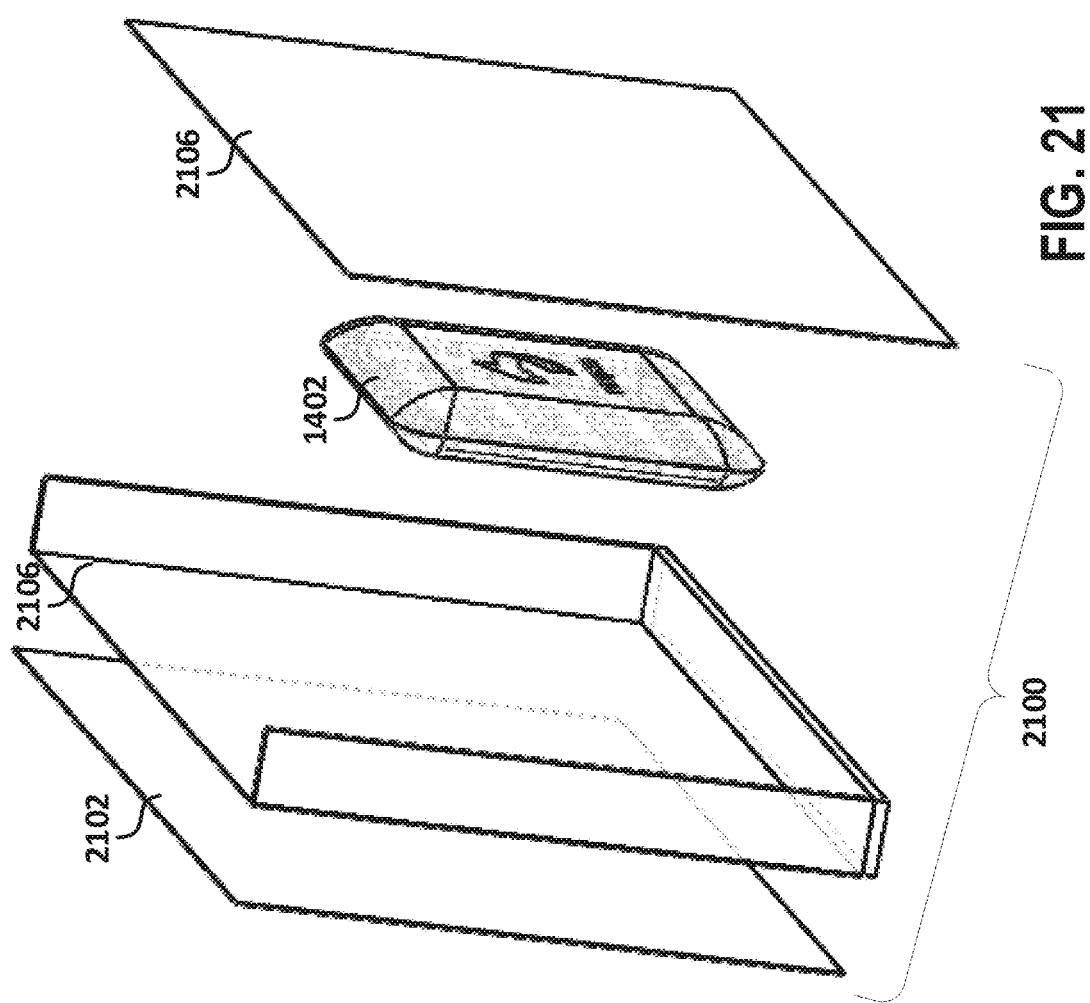
FIG. 21 illustrates, by way of example, a perspective view diagram of an embodiment of the bottom layers of FIG. 19B with an external device and a top layer.

FIG. 21 illustrates, by way of example, a perspective view diagram of an embodiment of layers 2100 that include the bottom layers 2100 of FIG. 19 with an external device 1402 between the bottom layers and a top layer 2106. The top layer 2106 is the inner most top layer and can be in contact with the external device 1402. The top layer 2106 and can be attached, such as by thread, adhesive, or other affixing means to any of the bottom layer(s), such as the layers 2102 and/or 2104.

Figure 22:
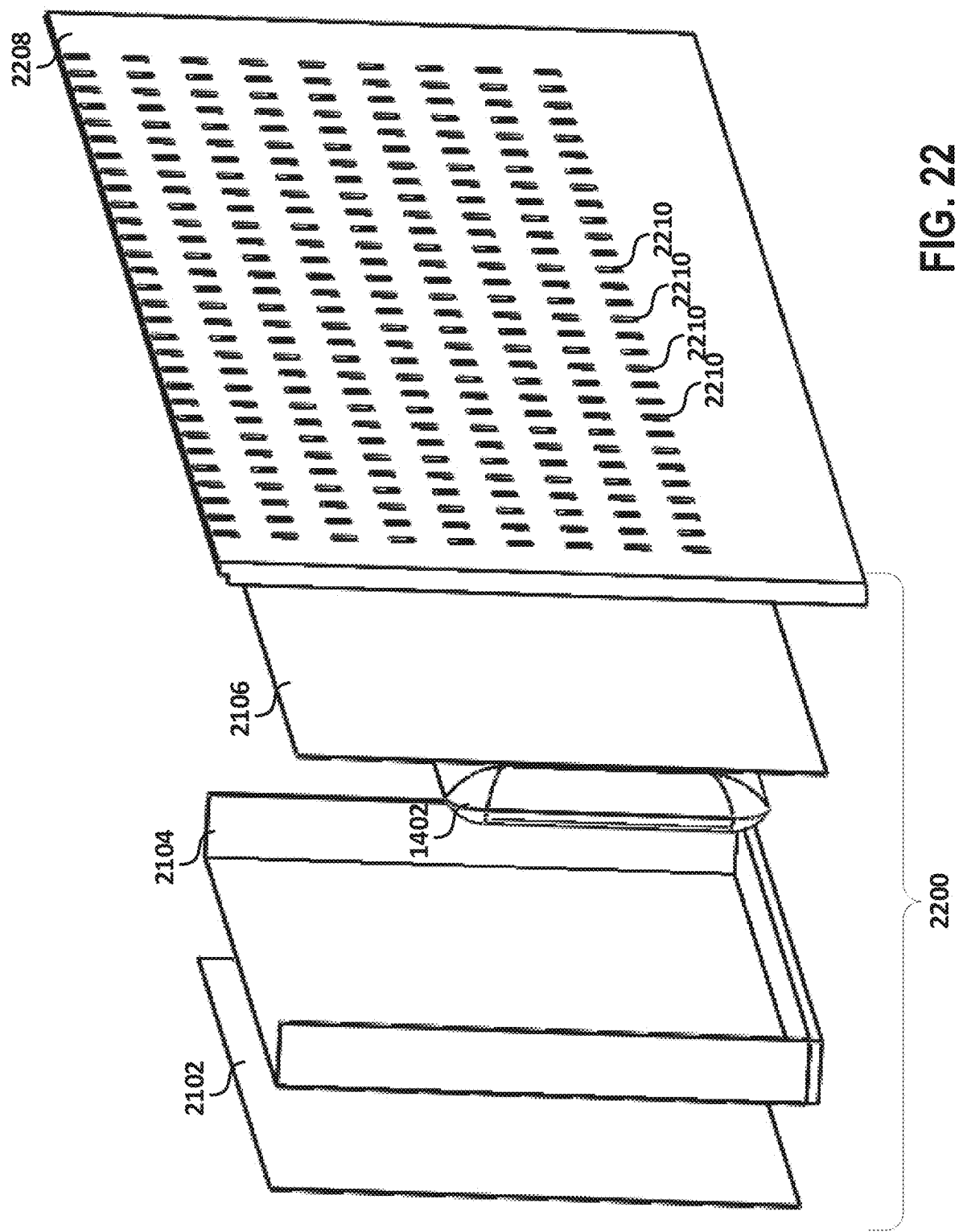
FIG. 22 illustrates, by way of example, a perspective view diagram of an embodiment of bottom layers of a pocket with an external device, a top layer, and an elastic band.

FIG. 22 illustrates, by way of example, a perspective view diagram of an embodiment of layers 2200 similar to the layers 2100 with an elastic band 2208 over the top layer 2106. The elastic band 2208 as illustrated includes optional holes 2210 therethrough, such as to help provide a ventilation area through which heat can escape and/or air can be brought in, such as to keep the pocket 1406 breathable. The holes 2210 can each include a greater height dimension than width dimension, such as shown in the example of FIG. 22. The height direction can be in generally the same direction as a height of a person wearing the wearable element. The width is generally perpendicular to the height. Such a configuration can allow the elastic band 2208 to stretch such as without compromising integrity or longevity of the band 2208. The holes 2210 can be positioned over just a portion of the band 2208, such as a portion over the layer 2106 or a portion thereof. The holes 2210 can alternatively be positioned over an entire width and height of the band 2208. The band 2208 illustrated is just a portion of a band so as to not obscure the view of the layers 2106, 2104, and 2102 and the external device 1402. The band 2208 will generally wrap completely around a human body so as to help apply a compressive force between the external device 1402 and the human body and help retain the external device in place near a tissue surface.

In an example, one or more mating attachment mechanisms can be provided on one or both of the external device 1402 and a layer of the pocket 1406. For example, an attachment mechanism can be provided on innermost surface of the top layers. The attachment mechanism can be mated with a mating attachment mechanism on the external device 1402 or a mating attachment mechanism on a sleeve in which the external device 1402 may be situated. Such attachment mechanisms are optional and the pocket 1406 can be sufficiently elastic or stretchable and can include such dimensions so as to keep the external device 1402 in a proper location with respect to the wearable element without a need for such an attachment mechanism. Attachment mechanisms can include mechanical fastening mechanisms, such as fabric hook and loop fasteners (e.g., VELCRO® fasteners), a magnet, a SCOTCH® fastener, or other attachment mechanism. In an example, an attachment mechanism can be affixed to a layer or to the external device 1402 using an adhesive.

FIG. 23 illustrates, by way of example, a cross-section view diagram of an embodiment of a system 2300 that includes the external device 1402 situated in a sleeve. The sleeve as illustrated includes the top layers 2306 and 2312, the bottom layers 2302 and 2304, and an attachment mechanism 2314 on the top layer 2312. One or more of the layers can include or use a dielectric member having a permittivity that is approximately the same as the relative permittivity of air.

FIG. 24A illustrates, by way of example, a perspective view diagram of an embodiment of a system 2400A similar to the system 2300, with the system 2400A including a cushion material 2416 on the bottom surface 2302. The cushion material 2416 helps provide support and protect the user from forces due to impact on the external device 1402. In an example, the cushion material 2416 includes a dielectric member having a relative permittivity the same or similar to that of ambient air (e.g., K=1). FIG. 24B illustrates, by way of example, a perspective view diagram of an embodiment of a system 2400B similar to the system 2300, with the system 2400B including the cushion material 2416 in the sleeve, such as on the bottom layer 2304 as opposed to on the bottom layer 2302 as in the example of FIG. 24A.

FIG. 25 illustrates, by way of example, a cross-section view diagram of an embodiment of a system 2500 including a sleeve with the external device 1402 situated therein. The sleeve as illustrated is situated between layers of the wearable element 1408, such as in the pocket 1406. In the embodiment of FIG. 25, the sleeve is affixed to the wearable element 1408 through an attachment mechanism 2510B on the wearable element 1408 mated with a fastening mechanism 2510A on the top layer 2312. The attachment mechanisms 2510A-B as illustrated are within the wearable element 1408. Additionally, another pair of fastening mechanisms may help affix the sleeve to the external device 1402. One fastening mechanism can be situated on the top layer 2306 and the mating fastening mechanism can be situated on the external device 1402.

FIG. 26 illustrates, by way of example, a perspective view diagram of an embodiment of an undergarment 2600 that includes mating fastening mechanisms 2620A and 2620B. The fastening mechanisms 2620A-B allow a user to open a bottom portion of the undergarment 2600 while wearing the undergarment 2600. Such an undergarment 2600 can help provide a way for a user to go to the bathroom without moving the external device 1402 relative to the implanted device 1404. Consider that the undergarment 2600 can include the pocket 1406 or other location at which the external device 1402 can be affixed. Using such an undergarment, a user can uncouple the fastening mechanisms 2620A-B, do their business, recouple the fastening mechanisms 2620A-B, and all the while retain the position of the external device 1402 relative to the implanted device 1404. In other embodiments, a user may have to move the undergarment 2600, thus moving the device 1402 relative to the implanted device 1404. The user may then reposition the external device 1402 to a communicable position (a position at which the external device communicates reliably with the implanted device 1404). In other examples, discussed elsewhere herein, it can be desirable or beneficial to the user to remove or relocate the external device 1402 away from a communicable position during user voiding.

FIG. 27 illustrates, by way of example, a block diagram of an embodiment of a system 2700 that includes multiple discrete external components (e.g., the external device 1402 and a battery 11442). The battery 11442 is external to the external device 1402 and situated near the external device 1402 in the pocket 1406 (or in the sleeve). In one or more embodiments, the battery 11442 can be situated outside the pocket 1406 or sleeve. In one or more embodiments, the battery 11442 includes one or more of a lithium polymer battery, a generally flat, flexible battery, a rechargeable battery (e.g., a wired battery charging capability or a wireless battery charging capability, such as through an inductive power link). The battery 11442 can provide electric power to the electric and electronic components (e.g., the internal circuitry, such as can include a transceiver 11444 and other components, such as circuitry of the external device, the source 102, or the like).

The location circuitry 11446 includes electric or electronic components (e.g., resistors, transistors, inductors, capacitors, diodes, sensors, logic gates, oscillators, multiplexers, antennas, radios, ADCs, DACs, speakers, or the like) that aid the user in situating the external device 1402 in a proper or suitable location for data and/or power communication with an implanted device. The location circuitry 11446 can include components to determine a received signal strength (RSS) of a signal from the implanted device 1404. The RSS can be used to create a tone, such as using a loudspeaker or the location circuitry 11446. The tone created can be modulated based on the value of the RSS so as to indicate to a user a relative value of the RSS. The user can then situate the external device 1402 at a location corresponding to a relatively high RSS (a tone that indicates a relatively high RSS). In one or more embodiments, the location circuitry 11446 includes a button that a user can press to initiate a placement operation and detection process. The location circuitry 11446 can provide the user with an indication (e.g., a tone or mechanical feedback, such as a vibration or pulse). The location circuitry 11446 can beep in response to the RSS dropping below a threshold value, such as to indicate to the user that the external device is not properly located. The location circuitry 11446 can refrain from beeping in response to determining the RSS is greater than (or equal to) a threshold value.

FIG. 28 illustrates, by way of example, a block diagram of an embodiment of a system 2800 that includes a single external device (the device 1402) in the pocket 1406. As is illustrated in FIG. 28, the battery 11442 can be included internally to a housing of the external device 1402, such as to be located between a top cover and a bottom cover of the housing.

FIG. 29 illustrates, by way of example, a block diagram of an embodiment of a system 2900 that includes multiple discrete external devices (the device 1402 and other circuitry 11650) in the pocket 1406. The system 11600 is similar to the system 11400, with the system 11600 including an antenna 11654 in the external device 1402, with some or all of the remaining circuitry external to the external device 1402. The antenna 11654 can be a component of a transceiver of the source 102, such as along with other circuitry. The control circuitry 11652 can be configured to provide one or more signals to the transceiver or antenna to cause the antenna to radiate electromagnetic energy, such as to the implanted device 1404. In one or more embodiments, the battery 11442 and/or the circuitry 11650 can be housed between a top cover and a bottom cover, such as to help radiate heat away from a user's body.

The antenna 11654 and/or the circuitry 11650 can provide an indication of the location of the external device 1402 relative to the implanted device 1404. The circuitry 11650 can include a motor that can cause a vibration to modulate as the external device 1402 gets closer to/farther from the implanted device 1404. The circuitry 11650 can provide an alert to the patient if the implanted device 1404 inside the patient shifts relative to the external device 1402, such as can be detected by monitoring the RSS. The frequency at which the antenna 11654 radiates electromagnetic energy can be programmable. The circuitry 11650 can monitor an amount of energy available from the battery 11442 and provide a low battery warning (e.g., a sound or vibration) if the amount of energy available from the battery 11442 drops below a specified threshold. The circuitry 11650 can provide an indication to turn on an implanted device 1404 for treatment. The circuitry 11650 can be connected to a network, such as to provide alerts from a mobile phone or by email.

Devices that include a power transmitter, such as the external device 1402, can "overheat" and cause discomfort or burn human skin unless they are carefully designed, especially when the device needs to be near the human body to operate properly. Data from at least one study indicates a "safe" heat absorption level of approximately 40 mW/cm$^2$. Near the overheating point, skin temperature increases approximately 0.80° C. for each additional 10 mW/cm$^2$ of absorbed power. During normal operation, the external device 1402 heats as a side effect of performing its intended function. Touching a heated device to human skin initiates a thermal transient transfer followed by a steady state. Using a pocket or sleeve around a device, or a device including an external housing, as discussed herein, such as can be used along with a device configured to transfer heat away from the body, can avoid user discomfort and/or skin burns.

Considering steady-state and to verify thermal safety, a designer can place a finished device in ambient air, heat the device to steady state, measure a device's surface temperature, and compare the surface temperature to a "known-safe" temperature, such as 41° C. If the measured temperature is less than the "known-safe" or threshold temperature, the designer can conclude that the device will not cause pain or burning of the skin. Although checking the thermal safety of a device by comparing the surface temperature to the "known safe" temperature may be convenient, the following factors may limit its applicability: 1) when compared to human skin, the ambient air presumably provides a higher thermal resistance to heat moving from the tested device; and 2) the higher thermal resistance forces the device to reach a higher temperature than it reaches when in direct contact to a material or skin. Using ambient air, the thermal load likely produces conservative test results. However, device performance generally improves with increasing power dissipation, so the test may be unjustifiably conservative. Knowing skin-temperature response and the heat output per area of the external device 1402, the resulting skin temperature can be calculated without calculating or measuring an actual device temperature.

A problem solved by one or more embodiments discussed in this subsection can include an external device with a form factor that will conveniently and discreetly situate an external power transmitter over a desired anatomy (at a desired location). Another problem solved by one or more embodiments discussed in this subsection can include an external housing for the power transmitter that will not burn, heat, and/or generally be felt by the patient.

The form factor can include an undergarment with a pocket or other mechanism in which an external device can be situated near the desired anatomy and therefore the implanted device. An external power transmitter device and/or pocket/sleeve can dissipate heat produced by power transmitter away from the body. The external form factor can include the wearable element, a battery to power the external device 1402, an antenna and other related electronics, a housing for the antenna and circuitry, and/or a sleeve or pocket in which to situate the housing.

As previously discussed, human skin can be sensitive to the heat dissipated through a surface of the device. Accordingly, the skin or surface temperature of the external device or other components near the human body can be an important constraint. Temperatures at one or more surfaces of an external device may become too hot to touch, thus leading to an uncomfortable user experience. For example, a high temperature at a housing surface may cause a user to stop using the device altogether. Further, high temperature surfaces can become a safety hazard due to localized skin burning or irritation. Thus, reducing a maximum temperature of an external device can be an important consideration.

An advantage of one or more embodiments can include an increased user comfort, for example when a user wears the external device using a garment or other wearable element or accessory. The systems discussed herein can be actively ventilated with heat and moisture regulation, such as can include air and water vapor permeability, rapid moisture absorption and conveyance capacity, absence of dampness, rapid drying, and/or low water absorption of the layer of material positioned adjacent to the skin. The systems discussed herein can have dimensional stability even when wet, can be made or durable or resilient materials, can be relatively easy to clean, can be lightweight, soft, and generally pleasant to the touch. The systems can include a high heat transfer characteristic away from the human body.

In accordance with several embodiments, the external device 1402 can be positioned (that is, retained in a chronic or static position relative to the body) above the left or right S3 foramen using a garment or wearable element. The S3 foramina are usually located about 11 cm from the anal verge or 9 cm cephalad to the tip of the coccyx. The S3 foramina are usually located 1.5-2 cm lateral to the midline at the level of the sacral notches or about 9 cm above the coccygeal drop-off. The external device 1402 can include the location circuitry 11446 that will help the patient determine when the external device 1402 is placed over a proper location. The S3 foramina are located generally one finger breadth above and below the S4 and S2 foramina, respectively. In an example, a garment configured to hold or position the external device 1402 can be provided in multiple sizes to accommodate different user body types and sizes. In an example, relative dimensions of the garment can be adjusted depending on body type. For example, a distance between a waistband of an underpants garment and an external device pocket can be different between large and small versions of the garment to better position the pocket, and therefore the external device 1402, relative to a target by S3.

The external device 1402, such as can include the battery 11442 and/or other circuitry, can be placed in a garment pocket or in a sleeve that includes layers similar to those discussed herein. A polymer coating can be used to line an inside of a sleeve or pocket, such as to make it waterproof. In one or more embodiments, Layer 5 can include a type of compression/elastic band in order to compress or bias the external device 1402 toward a desired location relative to a body feature when a garment comprising the pocket or sleeve is worn. The compression band can be integrated into the wearable element. The compression band can include conduits (holes) large enough to allow for heat dissipation. The compression band can have multiple channels or channels of different sizes. The compression band can have a variety of elasticity properties. The compression band can be about 0.5 mm-2 mm thick (e.g., 0.5-1 mm, 1 mm-1.5 mm, 1.5 mm-2 mm, 1 mm-2 mm, 0.5 mm-1.5 mm, overlapping ranges thereof, or any value within the recited ranges). The compression band can include conduits (e.g., holes) that are larger in a y direction (e.g., parallel to a height of a user) compared to an x-direction (e.g., perpendicular to the height of the user). Such a configuration can help conserve an elasticity of the band, while allowing for ventilation in the band.

In one or more embodiments there may be more than one pocket 1406, such as to provide a means to place an external device, such as for multiple different implanted device locations in one garment. In one or more embodiments, there can be a single pocket for the external device 1402. The pocket can be configured to be positioned above the sciatic notch. The pocket can span a width starting from about 30 mm lateral from the center of the left S3 foramen to about 30 mm right from the center of S3 foramen. In one or more embodiments, the pocket can have a total width of about 140 mm (about 70 mm to the right of the midline, and about 70 mm to the left of the midline). Other dimensions may be used as desired and/or required (e.g., length of between 60 mm and 200 mm, between 60 mm and 100 mm, between 70 mm and 150 mm, between 90 mm and 180 mm, between 100 mm and 160 mm, between 120 mm and 180 mm, between 130 mm and 150 mm, between 140 mm and 200 mm, overlapping ranges thereof, or any value within the recited ranges). In one or more embodiments, there can be a left pocket and a right pocket, each above and on opposite sides of the sciatic notch, such as can include a back pocket on the back left side above the left S3 foramen and another back pocket that sits directly above the S3 foramen. Each pocket can be about 60 mm in width by 60 mm in height. Other dimensions or shapes may be used as desired and/or required (e.g., 50 mm×50 mm, 70 mm×70 mm, 60 mm×50 mm, 50 mm×60 mm).

As previously discussed, mechanisms can be used to keep the external device 1402 at a proper location within the pocket 1406. Such mechanisms can help intermittent users remove the external device 1402 and replace the external device 1402, such as without compromising functionality of the external device 1402 or the implantable device 1404. The attachment mechanisms discussed herein can include, among other things, a mechanical fastener such as a fabric hook and loop fastener (e.g., a VELCRO® fastener), a SCOTCH® fastener, or magnets on the unit to secure to a corresponding fastener (e.g., another VELCRO® fastener in the pocket, a zipper, gussets, bellows, layers with off-set slits, or extra material that folds over the pocket 1406 can be used to close off the pocket 1406 from the external environment. A bottom layer of a pocket or sleeve can be covered with a sticky or tacky material, such as to help hold the device in place and/or to keep the pocket closed. The Layer 2 and/or Layer 3 can be at least partially covered in a rubber/silicone/sticky type gel or similar to help hold the external device 1402 in place. The wearable element can be placed over the external device 1402 with rubber/gel lining the whole pocket to hold the external device 1402 in place. In an example, a sleeve for the external device 1402 can include spandex or SPANX® material that can cover the external device 1402. The sleeve for the external device 1402 can include a flap, such as to help encapsulate or retain the external device 1402 in a specified location relative to a garment.

In one or more embodiments, a system can include a wearable element configured to be worn by a patient, and having an external device coupled thereto and configured to send and/or receive a wireless signal to communicate with an implanted device. The wearable element can include an attachment mechanism to situate the external device near (e.g., directly above, below, or to the side of) the S3 foramen so the external device will be in proximity to the implantable element. The external device 1402 can be placed at multiple locations on the wearable element. The external device 1402 can include an antenna positionable in proximity to the implanted device and configured to receive data from the implanted device or send power to the implanted device 1404. The external device 1402 can include location circuitry that provides an audible or tactile indication of the proper location of the external device 1402 on the wearable element. The external device 1402 can be a first external device and the system can include a second external device, wherein the first and second external devices are coupled to one another and positionable at multiple locations on the wearable element at a distance apart from one another. The second external device can be configured to provide power to the first external device. The second external device can include a flexible battery adapted to flex in response to motion of a user wearing the flexible battery. The wearable element can include one or more elastic straps. The wearable element can accommodate a variety of patient sizes and shapes. The wearable element can include one or more of an undergarment, a pouch, a belt, and an adhesive patch. The wearable element can include at least one pocket formed therein. In one or more embodiments, the at least one pocket can be movable relative to the wearable element.

Examples of different shapes, sizes, and styles of wearable elements include tight or non-tight shorts, such as mid-thigh shorts, high-thigh shorts, high-waist shorts, and/or mid-thigh shorts, briefs, such as high-waist briefs and/or retro briefs, hipsters, such as hi-hipster panty, panty boy shorts, and/or girl shorts, thongs, such as high-waisted thong, a bodysuit, such as an open bust bodysuit, a closed bust bodysuit, and/or a mid-thigh bodysuit suit, and pantyhose, such as a high waist and/or a no-show panty hose.

Some patients may not need or use constant stimulation from an implanted device, but can use stimulation intermittently from the external device 1402 to the implanted device 1404. This can be due, at least in part, to carryover effects of the electrostimulation. For example, a patient may only need stimulation one hour every 24 hours for continued efficacy of the therapy. What follows is some aspects surrounding an external device with design features specific to intermittent stimulation.

Sleepwear can include a pocket as discussed herein, such as for intermittent or constant treatment. The control circuitry can include a timer. The control circuitry can provide an indication to the user (noise, vibration, pulse, or other indication) in response to the timer beginning or expiring, such that the user can know how long to wear the external device 1402. The control circuitry can track a dosage the patient has received. The control circuitry can calculate a decay of the dosage to inform the patient when a subsequent stimulation dose is to be administered.

The external device 1402 can inform the user how long the device has been stimulating or has been turned on, such as through the control circuitry. The control circuitry can automatically stop providing electrical power to the antenna in response to determining an appropriate stimulation "dosage" has been achieved.

The control circuitry can let a user know when the stimulation will begin and end, such as through noises and/or vibrations. The control circuitry can alert the user to indicate when the user is to remove the external device 1402 and/or when the user is to place the external device 1402 near the implanted device 1404. The control circuitry can remind or provide an alarm to a user to indicate that the user should put the external device 1402 near the implanted device 1404, such as in response to determining the external device 1402 is not sufficiently close to the implanted device 1404. In one or more embodiments, the control circuitry may constantly remind the user until the external device 1402 is correctly placed for stimulation. The reminder can have a "snooze" feature such as to remind the user after a specific amount of time has elapsed. The control circuitry can include a BlueTooth®, Wi-Fi®, Zigbee®, or other short range connection circuitry that can interface with a phone, through which a user can program the control circuitry, such as to customize alarm settings.

There can be a setting for a user who wears the external device 1402 all day regardless of whether the stimulation is on or off. The external device 1402, such as through the control circuitry, can inform the patient when stimulation begins, ends, and/or a duration of stimulation. The external device 1402 can send an alert (e.g., an email, text, or other audible, visual or textual reminder) that a user can access via a mobile device (e.g., smartphone, tablet, computer via a software application program or a web browser). The alert may be sent by sending data over a wireless network. There can be a setting to insert the reminder on the user's calendar, such as through the control circuitry.

The external device 1402 can provide various audible alerts to indicate different alarms. These alarms can be programed through a software application (app) on a mobile device (e.g., smartphone or computing device). The external device can be allowed to store a certain amount of data in its memory before it would have to be connected to the mobile device (e.g., mobile phone), software application on the mobile device, or network, such as to upload the data before it is overwritten. The memory can track how long, for how many days, hours, etc. a user has received stimulation from an implanted device, such as by using the software application. The external source 102 can be pre-programmed with a selection of therapy regimes, such that the user can select using the software application. The user defined regimes may also be customized by the user, such as to allow the user to define their own timing settings, reminders, sounds, vibrations, power on, power off, settings, stimulation schedule, etc.

The control circuitry can include a safety feature which prevents over-heating of the external device 1402, such as can include monitoring a temperature of the external device 1402 itself and removing power to the external device 1402 if a threshold temperature is met or exceeded.

A password or other security mechanism can be required by the control circuitry 11652 or the app in order to adjust stimulation settings, such as power of stimulation, duration, etc. of the stimulation. The control circuitry 11652 can include device can include a Light Emitting Diode (LED) or other light that can be red or green, or whichever color to indicate the device is on, off, or searching for the implanted device, for example.

Figure 30:
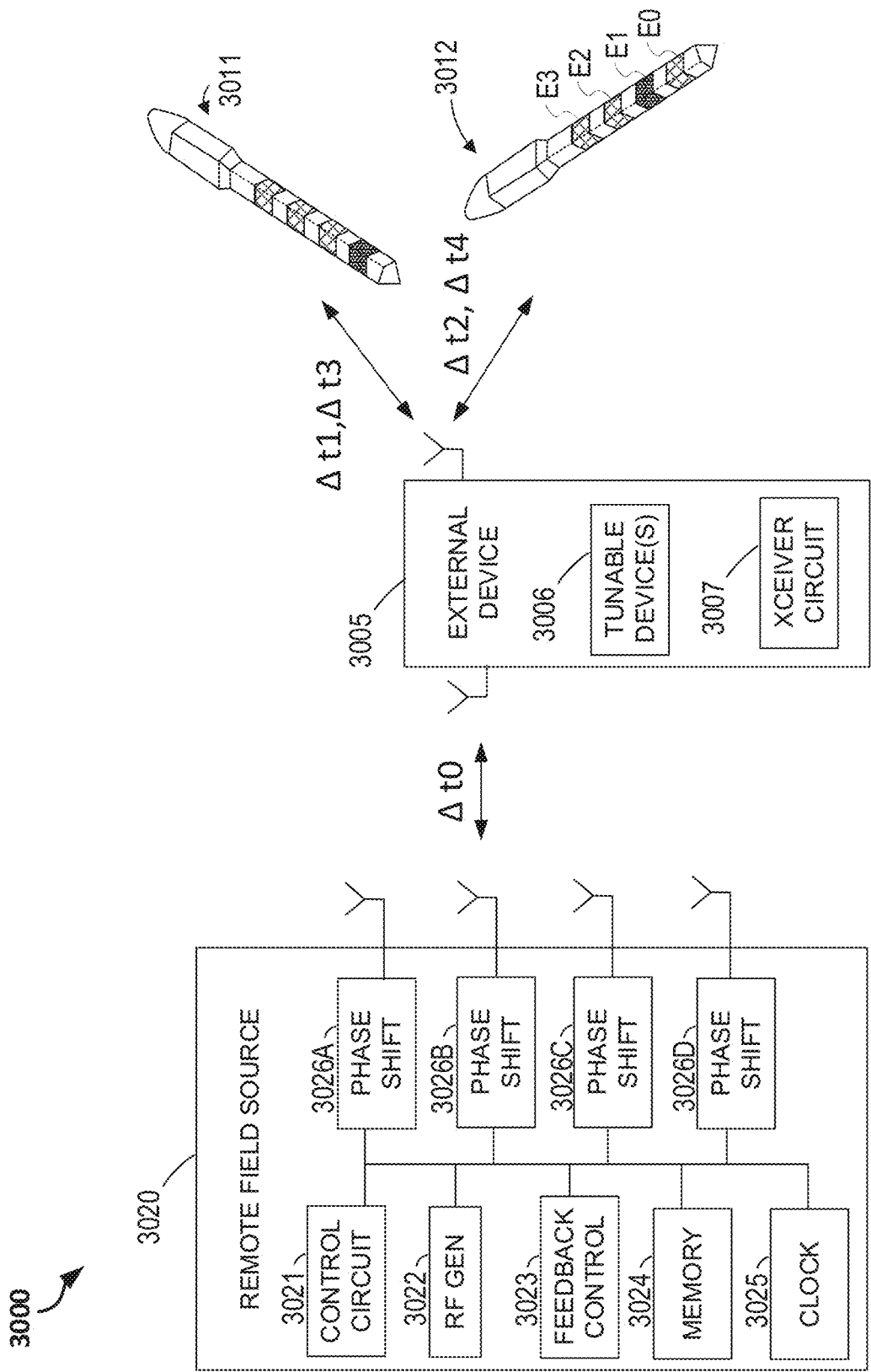
FIG. 30 illustrates, by way of example, a diagram of an embodiment of a system for selectively providing power and/or data communication to multiple target devices using a remote RF source and a midfield device.

FIG. 30 illustrates generally, by way of example, a diagram of an embodiment of a system 3000 for selectively providing power and/or data communication to multiple target devices using a remote RF source and a midfield device. The system 3000 includes a remote field source 3020, an external device 3005, and multiple target devices, such as can include implantable or implanted midfield devices. The external device 3005 can be configured to receive a field or an electromagnetic remote signal from the remote field source 3020, modulate the received signal, and in response communicate power and/or data signals to one or both of a first target device 3011 and the second target device 3012. That is, the external device 3005 can be configured to manipulate an evanescent field at or near an external tissue surface to direct transmission of wireless power and/or data signals within the tissue, such as to the first and/or second target device 3011 and 3012. The external device 3005 can be configured to communicate the power and/or data signals to a target device concurrently or asynchronously with receiving the remote signal from the remote field source 3020.

The remote field source 3020 can be configured to provide an electromagnetic field or remote RF signal (herein, "remote signal") that can be received and/or modulated by the external device 3005. The remote field source 3020 can include an RF generator circuitry 3022 that is configured to generate one or more RF signals based on instructions from a control circuitry 3021. The control circuitry 3021 can provide signal parameter information to the RF generator circuitry 3022, such as can include amplitude, frequency, phase, waveform morphology, or other signal parameter information. The remote field source 3020 can further include a memory circuitry 3024 or clock circuitry 3025 in data communication with one or more of the control circuitry 3021 and RF generator circuitry 3022, such as to store the signal parameter information and/or to trigger signal generation. In one or more embodiments, the remote field source 3020 includes a feedback control circuitry 3023 that can use the control circuitry 3021 to change one or more signal parameters and thereby change a characteristic of the remote signal that is provided. In one or more embodiments, the remote field source 3020 includes multiple RF outputs, and the multiple outputs can be excited independently. The multiple outputs can be excited concurrently or at separate times. In one or more embodiments, each output is coupled to a different phase shifter 3026A-3026D that can be used to change a characteristic of the outputted remote signal. Other signal-modifying elements can be included at or before the outputs, such as amplifier or attenuator circuitry.

The external device 3005 can include various hardware structures that are configured to receive a portion of the remote signal from the remote field source 3020 and, in response, transmit one or more different signals to the target devices. The external device 3005 can receive far field energy, such as from the remote field source 3020, and can use at least a portion of the received energy to manipulate an evanescent field and direct a power and/or data signal to a target device. In one or more embodiments, the external device 3005 includes control circuitry that harvests at least a portion of the energy received from the remote field source 3020 and controls one or more tunable devices 3006. The tunable devices 3006 can be used to change a characteristic of an input or receiver circuitry, such as to facilitate reception of the remote signal from the remote field source 3020. The tunable devices 3006 can be used to change a characteristic of an output or transmitter circuitry, such as to change a characteristic of a power and/or data signal transmitted from the external device 3005 to one of the first and second target devices 3011 and 3012. In one or more embodiments, the external device 3005 includes a transceiver circuitry 3007 configured to relay data communications between the remote field source 3020 and one or more target devices.

The remote field source 3020 can provide or broadcast the remote signal over a field interval $\Delta t0$. In response, the external device 3005 can communicate power and/or data to the first and/or second target devices 3011 and 3012 over first through fourth sequential intervals $\Delta t1$-$\Delta t4$. The field interval $\Delta t0$ can optionally at least partially overlap in time with one or more of the first through fourth intervals $\Delta t1$-$\Delta t4$. Other transmission interval schemes can similarly be used. In U.S. patent application Ser. No. 15/770,032, incorporated herein by reference in its entirety (see above), the discussion of FIG. 84 includes an example of using a remote field source and the external device to communicate multiple signals to different target devices.

In one or more embodiments, the external device 3005 and/or the remote field source 3020 can include or use a sensor, such as the sensor 107 in the example of FIG. 1. Information from the sensor can be used by the external device 3005 and/or by the remote field source 3020 to update a signal characteristic or therapy parameter.

Figure 31:
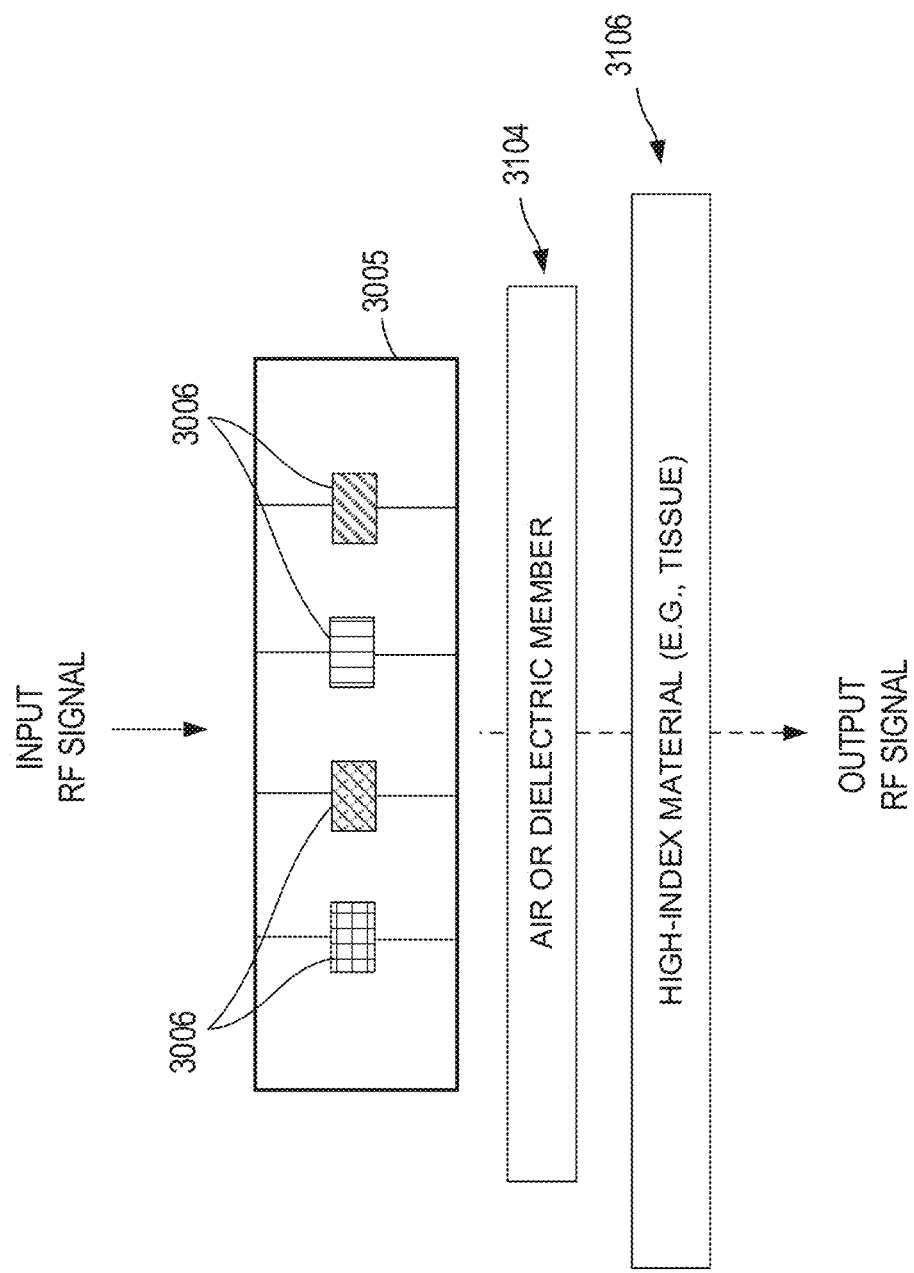
FIG. 31 illustrates, by way of example, a schematic of an embodiment of the external device with multiple tunable devices.

FIG. 31 illustrates, by way of example, a schematic of an embodiment of the external device 3005 (sometimes referred to as a midfield coupler, external source, or external device) with multiple tunable devices 3006. The external device 3005 is provided above an interface between a dielectric 3104, such as air or a dielectric insert or other dielectric member, and a high-index material 3106, such as body tissue. In one or more embodiments, the external device 3005 can be conceptualized as a lens that receives an electromagnetic signal and focuses or directs the received signal in a specified and controlled manner. The external device 3005 and/or the dielectric 3104 can be provided in or on a wearable element or garment near the high-index material 3106. One or more intervening layers of a garment material can be interposed between the external device 3005 and the dielectric 3104, or between the dielectric 3104 and the high-index material 3106. In an example, the dielectric 3104 is configured to have substantially the same relative permittivity as air.

The external device 3005 can include one or more subwavelength structures configured to receive an input RF signal (e.g., a far-field RF signal), and can include the same or other subwavelength structures configured to transmit one or more output RF signals to influence an evanescent wave at a tissue surface and thereby communicate power and/or data to one or more target devices, such as devices located in or beyond the high-index material 3106.

The tunable devices 3006 can include various passive or active devices that can be used to change an electrical signal characteristic. Some examples of a tunable element include a capacitor, resistor, inductor, amplifier circuitry, phase modulation circuitry, or other element, device, or circuitry that can be configured to receive an electrical signal and, in response, provide a different or updated electrical signal.

In one or more embodiments, the external device 3005 includes control circuitry that controls parameters of the tunable devices 3006. For example, the control circuitry can be configured to change a capacitance of a capacitor element in the external device 3005 to change an RF output signal characteristic. In one or more embodiments, the control circuitry is powered using a portion of an RF signal received at the external device 3005 from the remote field source 3020. The control circuitry can include components similar to, or the same as the processor circuitry 210, digital controller 548, or other control circuitry discussed herein.

In one or more embodiments, the external device 3005 includes memory circuitry (not shown in FIG. 31) that can be used to store parameter information for the tunable devices 3006. In one or more embodiments, the memory circuitry (e.g., nonvolatile, read-only, and/or flash memory) stores configuration information for the external device 3005, and the configuration information can include reference parameter information for the tunable devices 3006, historical parameter value information for the tunable devices 3006, or other information regarding a configuration or operating status of the external device 3005, the remote field source 3020, or one or more remote target devices.

In U.S. patent application Ser. No. 15/770,032, incorporated herein by reference in its entirety (see above), the illustration and discussion of FIG. 116 provide an example of a method that includes using different signal characteristics to communicate power and/or data signals to different target devices at different times. In the example of FIG. 116, the external device can receive a remote field signal over a field interval Δt0. The remote field signal can include power and/or data for use by an external device to facilitate communication from the external device to at least first and second target devices (e.g., implanted or implantable midfield receiver devices). FIG. 116 illustrates a series of signals, including first, second, third, and fourth signals S1, S2, S3, and S4, respectively, that are sequentially transmitted from the external device to one or the other of first and second target devices. FIG. 116 illustrates how various ones of the tunable devices (e.g., tunable devices 3006 from the example of FIG. 30 in the instant document) or elements can be configured during different signal transmission intervals. By selecting different parameter values for the various elements (e.g., Elements 1-4 in the example of FIG. 116 of U.S. patent application Ser. No. 15/770,032), the external device can be configured to receive different remote field signals and/or to transmit different signals to one or more target devices by differently modulating an evanescent field.

Figure 32:
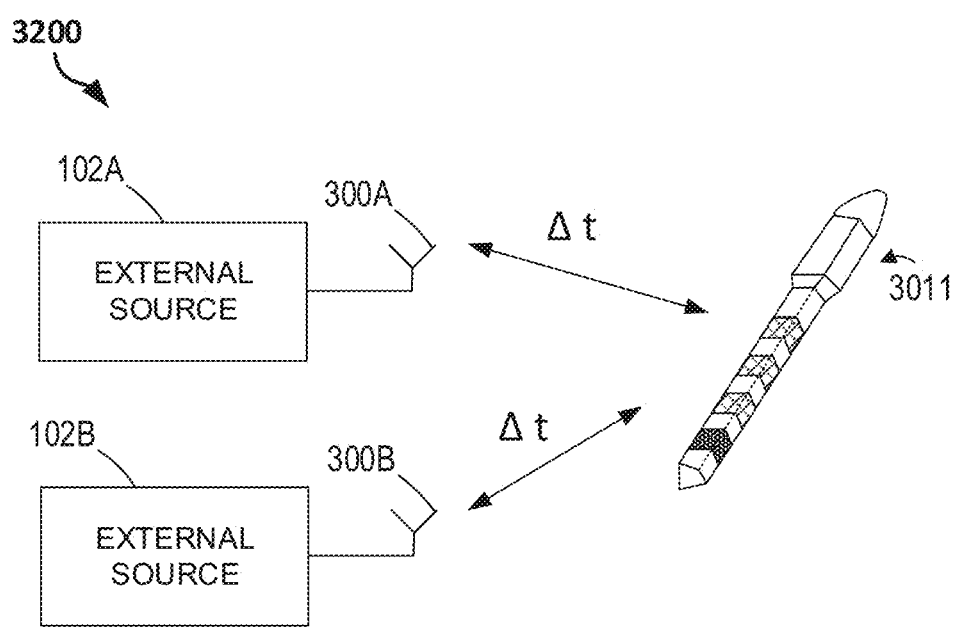
FIG. 32 illustrates, by way of example, a diagram of an embodiment of a system that includes multiple external midfield transceivers.

FIG. 32 illustrates, by way of example, a diagram of an embodiment of a system 3200 that includes multiple external midfield transceivers (e.g., multiple source devices). For example, the system 3200 includes a first external source 102A and a separate second external source 102B. Each of the first and second external sources 102A and 102B can have a respective antenna, such as a first antenna 300A and a second antenna 300B. The first and second antennas 300A and 300B can have the same or similar features as in one or more of the other external source devices described herein.

Both of the first and second external midfield antennas 300A and 300B can be configured to transmit power and/or data signals to the first target device 3011. In one or more embodiments, both of the first and second antennas 300A and 300B are configured to transmit a separate power signal to the first target device 3011 concurrently, that is, during a common interval Δt. In one or more embodiments, the transmitted power signals from the first and second antennas 300A and 300B are selected to interfere constructively and a resulting or combined field is received by the first target device 3011. In one or more embodiments, the first and second antennas 300A and 300B comprise two of multiple external transceivers arranged as a mesh network, wherein each of the multiple external transceivers is configured to exchange data to help coordinate power transfers or data transfers to the first target device 3011 or to other devices.

In an example, the first and second external sources 102A and 102B can be provided near a tissue surface using a wearable element or garment that is configured to hold or position multiple source devices. In an example, the wearable element includes multiple pockets provided at different body locations when the element is worn by a user, and each pocket can be configured to receive and retain a different external source device. Each pocket can be configured to include, or to be adjacent to, a dielectric member or dielectric insert provided between a body tissue surface and an external source.

Figure 33:
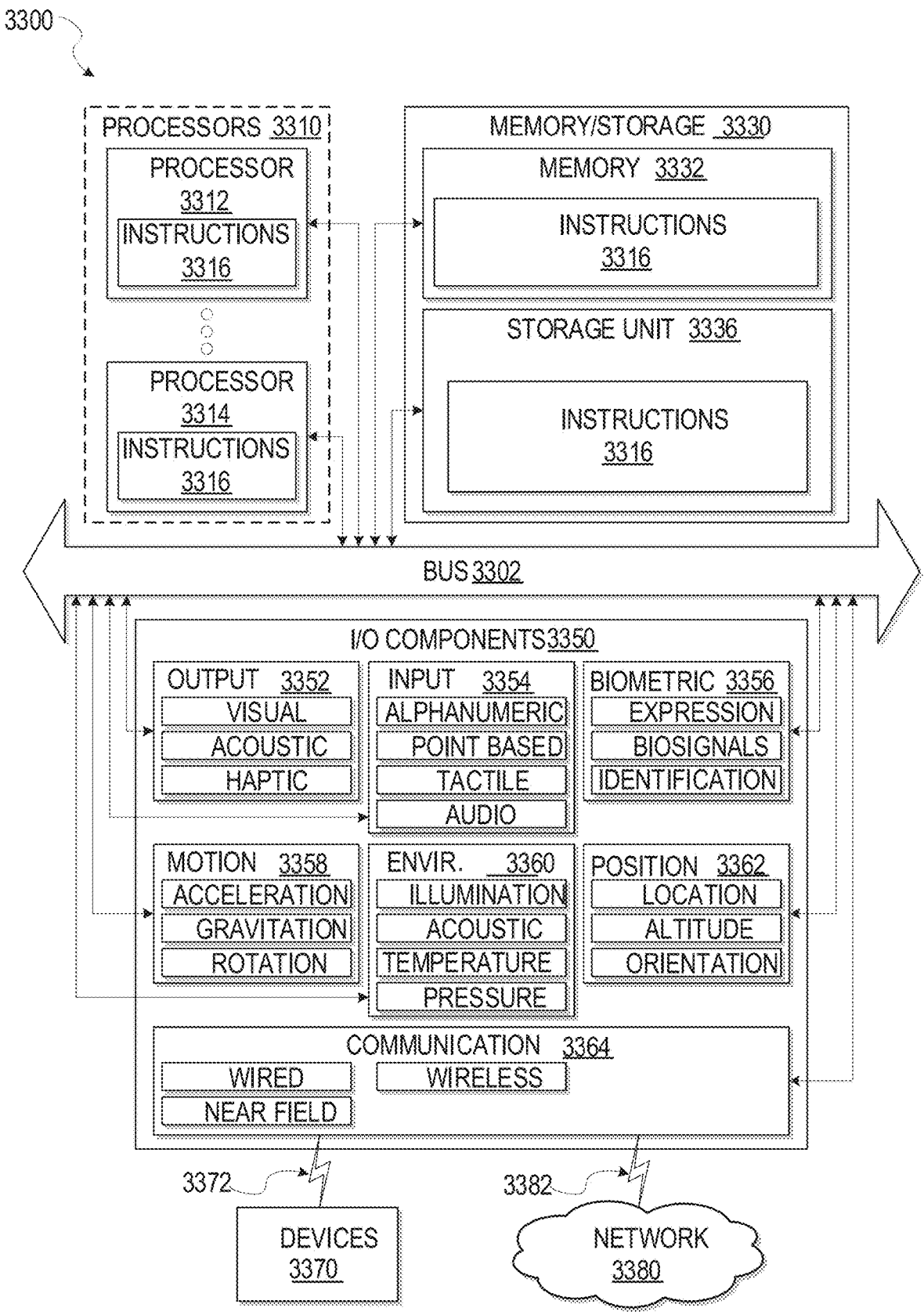
FIG. 33 illustrates, by way of example, a system with which one or more methods discussed herein can be performed.

FIG. 33 illustrates, by way of example, a block diagram of an embodiment of a machine 3300 with which one or more methods discussed herein can be performed or in conjunction with one or more systems or devices described herein may be used. In one or more embodiments, the implantable device 110, the source 102, the sensor 107, the processor circuitry 210, the digital controller 548, circuitry in the circuitry housing, system control circuitry, power management circuitry, a controller, stimulation circuitry, energy harvest circuitry, synchronization circuitry, the external device, control circuitry, feedback control circuitry, the implanted device, location circuitry, other circuitry of the implantable device, and/or circuitry that is a part of or connected to the external source, can include one or more of the items of the machine 3300. The machine 3300, according to some example embodiments, is able to read instructions from a machine-readable medium (e.g., a machine-readable storage medium) and to perform any one or more of the methodologies, one or more operations of the methodologies, or one or more circuitry functions discussed herein, such as the methods described with regard to FIGS. 18A, 18B, 18C, and/or 18D. For example, FIG. 33 shows a diagrammatic representation of the machine 3300 in the example form of a computer system, within which instructions 3316 (e.g., software, a program, an application, an applet, an app, or other executable code) for causing the machine 3300 to perform any one or more of the methodologies discussed herein can be executed. The instructions transform the general, non-programmed machine into a particular machine programmed to carry out the described and illustrated functions in the manner described. In alternative embodiments, the machine 3300 operates as a stand-alone device or can be coupled (e.g., networked) to other machines. In a networked deployment, the machine 3300 can operate in the capacity of a server machine or a client machine in a server-client network environment, or as a peer machine in a peer-to-peer (or distributed) network environment. Various portions of the machine 3300 can be included in, or used with, one or more of the external source 102 and the implantable device 110. In one or more embodiments, different instantiations or different physical hardware portions of the machine 3300 are separately implanted at the external source 102 and the implantable device 110.

In one or more embodiments, the machine 3300 can comprise, but is not limited to, a server computer, a client computer, a personal computer (PC), a tablet computer, a laptop computer, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 3316, sequentially or otherwise, that specify actions to be taken by machine 3300. Further, while only a single machine 3300 is illustrated, the term "machine" shall also be taken to include a collection of machines 3300 that individually or jointly execute the instructions 3316 to perform any one or more of the methodologies discussed herein.

The machine 3300 can include processors 3310, memory 3330, or I/O components 3350, which can be configured to communicate with each other such as via a bus 3302. In one or more embodiments embodiment, the processors 3310 (e.g., a Central Processing Unit (CPU), a Reduced Instruction Set Computing (RISC) processor, a Complex Instruction Set Computing (CISC) processor, a Graphics Processing Unit (GPU), a Digital Signal Processor (DSP), an Application Specific Integrated Circuitry (ASIC), a Radio-Frequency Integrated Circuitry (RFIC), another processor, or any suitable combination thereof) can include, for example, processor 3312 and processor 3314 that can execute instructions 3316. The term "processor" is intended to include multi-core processors that can include two or more independent processors (sometimes referred to as "cores") that can execute instructions contemporaneously. Although FIG. 33 shows multiple processors, the machine 3300 can include a single processor with a single core, a single processor with multiple cores (e.g., a multi-core process), multiple processors with a single core, multiple processors with multiples cores, or any combination thereof.

The memory/storage 3330 can include a memory 3332, such as a main memory, or other memory storage, and a storage unit 3336, both accessible to the processors 3310 such as via the bus 3302. The storage unit 3336 and memory 3332 store the instructions 3316 embodying any one or more of the methodologies or functions described herein. The instructions 3316 can also reside, completely or partially, within the memory 3332, within the storage unit 3336, within at least one of the processors 3310 (e.g., within the processor's cache memory), or any suitable combination thereof, during execution thereof by the machine 3300. Accordingly, the memory 3332, the storage unit 3336, and the memory of processors 3310 are examples of machine-readable media.

As used herein, "machine-readable medium" means a device able to store instructions and data temporarily or permanently and can include, but is not be limited to, random-access memory (RAM), read-only memory (ROM), buffer memory, flash memory, optical media, magnetic media, cache memory, other types of storage (e.g., Erasable Programmable Read-Only Memory (EEPROM)) and/or any suitable combination thereof. The term "machine-readable medium" should be taken to include a single medium or multiple media (e.g., a centralized or distributed database, or associated caches and servers) able to store instructions 3316. The term "machine-readable medium" shall also be taken to include any medium, or combination of multiple media, that is capable of storing instructions (e.g., instructions 3316) for execution by a machine (e.g., machine 3300), such that the instructions, when executed by one or more processors of the machine 3300 (e.g., processors 3310), cause the machine 3300 to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

The I/O components 3350 can include a wide variety of components to receive input, provide output, produce output, transmit information, exchange information, capture measurements, and so on. The specific I/O components 3350 that are included in a particular machine will depend on the type of machine. For example, portable machines such as mobile phones will likely include a touch input device or other such input mechanisms, while a headless server machine will likely not include such a touch input device. It will be appreciated that the I/O components 3350 can include many other components that are not shown. The I/O components 3350 are grouped according to functionality merely for simplifying the following discussion and the grouping is in no way limiting. In various example embodiments, the I/O components 3350 can include output components 3352 and input components 3354. The output components 3352 can include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 3354 can include alphanumeric input components (e.g., a keyboard, a touch screen configured to receive alphanumeric input, a photo-optical keyboard, or other alphanumeric input components), point based input components (e.g., a mouse, a touchpad, a trackball, a joystick, a motion sensor, or other pointing instrument), tactile input components (e.g., a physical button, a touch screen that provides location and/or force of touches or touch gestures, or other tactile input components), audio input components (e.g., a microphone), and the like.

In further example embodiments, the I/O components 3350 can include biometric components 3356, motion components 3358, environmental components 3360, or position components 3362 among a wide array of other components. For example, the biometric components 3356 can include components to detect expressions (e.g., hand expressions, facial expressions, vocal expressions, body gestures, or eye tracking), measure physiologic signals (e.g., blood pressure, heart rate, body temperature, perspiration, or brain waves, neural activity, or muscle activity), identify a person (e.g., voice identification, retinal identification, facial identification, fingerprint identification, or electroencephalogram based identification), and the like.

The motion components 3358 can include acceleration sensor components (e.g., accelerometer), gravitation sensor components, rotation sensor components (e.g., gyroscope), and so forth. In one or more embodiments, one or more of the motion components 3358 can be incorporated with the external source 102 or the implantable device 110, and can be configured to detect motion or a physical activity level of a patient. Information about the patient's motion can be used in various ways, for example, to adjust a signal transmission characteristic (e.g., amplitude, frequency, etc.) when a physical relationship between the external source 102 and the implantable device 110 changes or shifts.

The environmental components 3360 can include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that can provide indications, measurements, or signals corresponding to a surrounding physical environment. The position components 3362 can include location sensor components (e.g., a Global Position System (GPS) receiver component), altitude sensor components (e.g., altimeters or barometers that detect air pressure from which altitude can be derived), orientation sensor components (e.g., magnetometers), and the like. In one or more embodiments, the I/O component(s) 3350 can be a part of the implantable device 110 and/or the external source 102.

Communication can be implemented using a wide variety of technologies. The I/O components 3350 can include communication components 3364 operable to couple the machine 3300 to a network 3380 or devices 3370 via coupling 3382 and coupling 3372 respectively. For example, the communication components 3364 can include a network interface component or other suitable device to interface with the network 3380. In further examples, communication components 3364 can include wired communication components, wireless communication components, cellular communication components, Near Field (nearfield) Communication (NFC) components, midfield communication components, farfield communication components, and other communication components to provide communication via other modalities. The devices 3370 can be another machine or any of a wide variety of peripheral devices.

Moreover, the communication components 3364 can detect identifiers or include components operable to detect identifiers. For example, the communication components 3364 can include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra. Code, UCC RSS-2D bar code, and other optical codes), or acoustic detection components (e.g., microphones to identify tagged audio signals). In addition, a variety of information can be derived via, the communication components 3364, such as, location via Internet Protocol (IP) geo-location, location via Wi-Fi® signal triangulation, location via detecting a NFC beacon signal that can indicate a particular location, and so forth. In an example, the verification device 1701 can include or use one or more of the communication components 3364.

In some embodiments, the systems comprise various features that are present as single features (as opposed to multiple features). For example, in one embodiment, the system includes a single external source and a single implantable device or stimulation device with a single antenna. Multiple features or components are provided in alternate embodiments. In some embodiments, the system comprises one or more of the following: means for tissue stimulation (e.g., an implantable stimulation device), means for powering (e.g., a midfield powering device or midfield coupler), means for receiving (e.g., a receiver), means for transmitting (e.g., a transmitter), means for controlling (e.g., a processor or control unit), or means for receiving and positioning an external transmitter device proximal to an implanted device, etc.

The following Aspects provide a non-limiting overview of the garments, garment features, systems, and methods for controlling therapy discussed herein.

Aspect 1 can include or use subject matter (such as an apparatus, a system, a device, a method, a means for performing acts, or a device readable medium including instructions that, when performed by the device, can cause the device to perform acts, or an article of manufacture), such as can include or use a garment for receiving and positioning an external transmitter device proximal to an implanted device. In Aspect 1, the garment can include a garment body comprising a flexible material, wherein the flexible material has a first relative permittivity characteristic, a first receptacle coupled with, or comprising a portion of, the garment body and configured to receive and position the external transmitter device near a tissue interface when the garment is worn by a user, and a dielectric portion provided between the first receptacle and the tissue interface, wherein the dielectric portion has a second relative permittivity characteristic, wherein the second relative permittivity characteristic is approximately the same as the relative permittivity of air and is different from the first relative permittivity characteristic of the flexible material.

Aspect 2 can include or use, or can optionally be combined with the subject matter of Aspect 1, to optionally include or use the dielectric portion including a compressible material having a relative permittivity that is approximately the same as the relative permittivity of air when the material is compressed or uncompressed.

Aspect 3 can include or use, or can optionally be combined with the subject matter of one or any combination of Aspects 1 or 2 to optionally include or use the dielectric portion including a polychloroprene rubber having a relative permittivity that is approximately the same as the relative permittivity of air when the polychloroprene rubber is compressed or uncompressed.

Aspect 4 can include or use, or can optionally be combined with the subject matter of one or any combination of Aspects 1 through 3 to optionally include or use a second receptacle adjacent to the first receptacle and configured to receive the dielectric portion.

Aspect 5 can include or use, or can optionally be combined with the subject matter of Aspect 4, to optionally include or use the first and second receptacles configured to share a common sidewall.

Aspect 6 can include or use, or can optionally be combined with the subject matter of one or any combination of Aspects 1 through 5 to optionally include or use the dielectric portion dimensioned to separate the first receptacle from the tissue interface by at least a specified minimum separation distance, the specified minimum separation distance selected to avoid exceeding a defined maximum loading on a transmission antenna of the external transmitter device.

Aspect 7 can include or use, or can optionally be combined with the subject matter of one or any combination of Aspects 1 through 6 to optionally include or use the dielectric portion dimensioned to separate the first receptacle from the tissue interface by at least a specified minimum separation distance, the specified minimum separation distance selected to reduce a rate at which electromagnetic energy is absorbed by patient tissue at or near the tissue interface.

Aspect 8 can include or use, or can optionally be combined with the subject matter of one or any combination of Aspects 1 through 7 to optionally include or use the dielectric portion configured to inhibit heat transfer from the first receptacle to the tissue interface.

Aspect 9 can include or use, or can optionally be combined with the subject matter of one or any combination of Aspects 1 through 8 to optionally include or use the first receptacle including at least a first wall provided adjacent to the dielectric portion, and wherein the first wall and the dielectric portion have different relative permittivity characteristics.

Aspect 10 can include or use, or can optionally be combined with the subject matter of Aspect 9, to optionally include or use the first wall comprising one or more of a woven fabric, non-woven fabric, mesh, or nylon material.

Aspect 11 can include or use, or can optionally be combined with the subject matter of one or any combination of Aspects 1 through 10 to optionally include or use the garment body including an elastic waistband or chest band coupled to the first receptacle.

Aspect 12 can include or use, or can optionally be combined with the subject matter of Aspect 11, to optionally include or use a waistband, wherein the waistband is configured to position the first receptacle at or near an S3 foramen when the garment is worn by the user.

Aspect 13 can include or use, or can optionally be combined with the subject matter of Aspect 11, to optionally include or use the elastic waistband or chest band having thermally conductive fibers configured to sink heat energy from the first receptacle.

Aspect 14 can include or use, or can optionally be combined with the subject matter of one or any combination of Aspects 1 through 13 to optionally include or use a verification device, wherein the verification device communicates with the external transmitter device to enable one or more functions of the external transmitter device.

Aspect 15 can include or use, or can optionally be combined with the subject matter of Aspect 14, to optionally include or use the verification device including an RFID tag.

Aspect 16 can include or use, or can optionally be combined with the subject matter of one or any combination of Aspects 1 through 15 to optionally include or use the receptacle including one or more through-holes configured to receive respective electrodes protruding from the external transmitter device toward a body tissue surface.

Aspect 17 can include or use, or can optionally be combined with any portion or combination of any portions of any one or more of Aspects 1 through 16 to include or use a system that includes an external midfield transmitter device with one or more structures excitable by a voltage or current source to manipulate evanescent fields outside of tissue to generate a propagating and focused field in the tissue and thereby communicate power and/or data signals from the external midfield transmitter device to the implanted midfield receiver device. In Aspect 17, the system can include a garment comprising at least one receptacle configured to receive the external midfield transmitter device and position it near a tissue interface, and a dielectric portion provided between the receptacle and the tissue interface, wherein a dielectric permittivity characteristic of the dielectric portion is approximately the same as the relative permittivity of air.

Aspect 18 can include or use, or can optionally be combined with the subject matter of Aspect 17, to optionally include or use the receptacle including at least a first wall provided adjacent to the dielectric portion, and wherein the first wall and the dielectric portion have different relative permittivity characteristics.

Aspect 19 can include or use, or can optionally be combined with the subject matter of one or any combination of Aspects 17 or 18 to optionally include or use the garment including an underwear garment configured to be worn at or about the waist of a patient, and wherein the receptacle is configured to position the external midfield transmitter device at a lower spine region of the patient when the underwear garment is worn by the patient.

Aspect 20 can include or use, or can optionally be combined with the subject matter of Aspect 19, to optionally include or use one or more signals from the external midfield transmitter device configured to control delivery of an electrostimulation therapy from the implanted midfield receiver device to a neural target in a pelvic region of the patient.

Aspect 21 can include or use, or can optionally be combined with the subject matter of Aspect 19, to optionally include or use the external midfield transmitter device is configured to cause the implanted midfield receiver device to provide a therapy to the patient when the garment is worn by the patient, the therapy configured to inhibit or interfere with patient urination when the garment is worn.

Aspect 22 can include or use, or can optionally be combined with the subject matter of Aspect 21, to optionally include or use the garment configured to be displaced away from the waist of the patient when the patient urinates to thereby interrupt the therapy.

Aspect 23 can include or use, or can optionally be combined with the subject matter of one or any combination of Aspects 19 through 22 to optionally include or use the external midfield transmitter device configured to cause the implanted midfield receiver device to provide a therapy to the patient only when (1) the garment is worn by the patient, (2) the receptacle retains the external midfield transmitter device, and (3) the external midfield transmitter actively communicates the power and/or data signals to the implanted midfield receiver device, and Wherein the therapy is configured to inhibit or interfere with patient urination.

Aspect 24 can include or use, or can optionally be combined with the subject matter of one or any combination of Aspects 17 through 23 to optionally include or use the external midfield transmitter device configured to coordinate a chronic stimulation therapy provided by the implanted midfield receiver device to a target region at or near the pudendal nerve, the genitofemoral nerve, or the sciatic nerve.

Aspect 25 can include or use, or can optionally be combined with the subject matter of one or any combination of Aspects 17 through 24 to optionally include or use the external midfield transmitter device including circuitry configured to determine whether a minimum power transmission efficiency exists between the external midfield transmitter device and the implanted midfield receiver device.

Aspect 26 can include or use, or can optionally be combined with the subject matter of one or any combination of Aspects 17 through 25 to optionally include or use the external midfield transmitter device including circuitry configured to determine a garment status including whether the garment is being worn by a patient and the circuitry is configured to enable or disable a patient therapy based on the determined garment status.

Aspect 27 can include or use, or can optionally be combined with the subject matter of Aspect 26, to optionally include or use the circuitry configured to determine a garment status including a position sensor.

Aspect 28 can include or use, or can optionally be combined with the subject matter of one or any combination of Aspects 17 through 27 to optionally include or use the external midfield transmitter device including control circuitry configured to determine whether a patient voiding event is about to occur, and, when the control circuitry determines that a patient voiding event is about to occur, then the control circuitry is configured to inhibit delivery of a neural stimulation therapy from the implanted midfield receiver device.

Aspect 29 can include or use, or can optionally be combined with the subject matter of one or any combination of Aspects 17 through 28 to optionally include or use the dielectric portion including a compressible neoprene insert having approximately the same relative permittivity as air.

Aspect 30 can include or use, or can optionally be combined with the subject matter of one or any combination of Aspects 17 through 29 to optionally include or use the dielectric portion is configured to separate the receptacle from the tissue interface by at least a specified minimum separation distance, the specified minimum separation distance selected to (1) reduce loading on the one or more excitable structures of the external midfield transmitter device, or (2) reduce a rate at which electromagnetic energy is absorbed by the tissue at or near the tissue interface.

Aspect 31 can include or use, or can optionally be combined with any portion or combination of any portions of any one or more of Aspects 1 through 30 to include or use, a method for controlling delivery of neural stimulation therapy using a system that includes an implanted midfield device and external midfield transmitter device, wherein the external midfield transmitter device includes one or more structures excitable to manipulate evanescent fields outside of tissue to generate a propagating and focused field in the tissue and thereby communicate power and/or data signals to the implanted midfield device, wherein the implanted midfield device includes one or more electrodes for delivering an electrostimulation therapy to a neural target, and the delivered therapy uses, at least in part, energy received from the external midfield transmitter device. In Aspect 31, the method can include positioning the external midfield transmitter device at or near a tissue interface and the implanted midfield device using a garment, using energy received from the external midfield transmitter device, providing a stimulation therapy at or near a neural target in a pelvic region of a patient using the implanted midfield device, and determining, using a control circuit, whether a voiding event is, or is likely to be, imminent or occurring for the patient. Aspect 31 can further include enhancing voiding efficiency for the patient, including inhibiting or ceasing the stimulation therapy provided to the neural target when the voiding event is determined to be, or is determined to be likely to be, imminent or occurring for the patient.

Aspect 32 can include or use, or can optionally be combined with the subject matter of Aspect 31, to optionally include or use the determining whether the voiding event is, or is likely to be, imminent or occurring for the patient, including using the control circuit to determine a void interval for the patient based on information from one or more sensors configured to determine a fullness characteristic about the patient's bladder.

Aspect 33 can include or use, or can optionally be combined with the subject matter of one or any combination of Aspects 31 through 32 to optionally include or use the determining whether the voiding event is, or is likely to be, imminent or occurring for the patient, including using the control circuit to identify noncommunication between the external midfield transmitter device and the implanted midfield device.

Aspect 34 can include or use, or can optionally be combined with the subject matter of one or any combination of Aspects 31 through 33 to optionally include or use the determining whether the voiding event is, or is likely to be, imminent or occurring for the patient, including using a control circuit provided in one or both of the implanted midfield device and the external midfield transmitter device.

Aspect 35 can include or use, or can optionally be combined with the subject matter of Aspect 34, to optionally include or use the determining whether the voiding event is, or is likely to be, imminent or occurring for the patient, including using information from a position sensor coupled to the external midfield transmitter device, wherein the position sensor is configured to determine when the external midfield transmitter device moves away from the tissue interface.

Aspect 36 can include or use, or can optionally be combined with the subject matter of Aspect 34, to optionally include or use the control circuit provided in the implanted midfield device, and wherein determining whether the voiding event is, or is likely to be, imminent or occurring for the patient includes using information from the implanted midfield device about whether it is receiving a substantially continuous power signal from the external midfield transmitter device.

Aspect 37 can include or use, or can optionally be combined with any portion or combination of any portions of any one or more of Aspects 1 through 36 to include or use, subject matter that can include a garment for receiving and positioning an external transmitter device proximal to an implanted device. In Aspect 37, the garment can include a garment body comprising a flexible material configured to be worn by a user, a first receptacle comprising a portion of the garment body and configured to receive and position the external transmitter device near a tissue interface when the garment is worn by the user, and a dielectric portion provided between the first receptacle and the tissue interface to electrically decouple contents of the first receptacle from tissue at the tissue interface, wherein the dielectric portion has a first relative permittivity that is different from a relative permittivity of the tissue at the tissue interface.

Aspect 38 can include or use, or can optionally be combined with the subject matter of Aspect 37, to optionally include or use the dielectric portion comprises a compressible polychloroprene rubber having a relative permittivity that is approximately the same as the relative permittivity of air when the polychloroprene rubber is compressed or uncompressed.

Aspect 39 can include or use, or can optionally be combined with the subject matter of one or any combination of Aspects 37 or 38 to optionally include or use the dielectric portion dimensioned to separate the first receptacle from the tissue interface by at least a specified minimum separation distance, the specified minimum separation distance selected to (1) avoid exceeding a defined maximum loading on a transmission antenna of the external transmitter device and/or to (2) reduce a rate at which electromagnetic energy is absorbed by patient tissue at or near the tissue interface.

Aspect 40 can include or use, or can optionally be combined with the subject matter of one or any combination of Aspects 37 through 39 to optionally include or use the dielectric portion configured to inhibit heat transfer from the first receptacle to the tissue interface.

Aspect 41 can include or use, or can optionally be combined with the subject matter of one or any combination of Aspects 37 through 40 to optionally include or use the garment body comprises an elastic waistband coupled to the first receptacle, and the waistband is configured to position the first receptacle at or near an S3 foramen when the garment is worn by the user.

Each of these non-limiting examples or aspects can stand on its own, or can be combined in various permutations or combinations with one or more of the other examples or aspects herein.

Although various general and specific embodiments are described herein, it will be evident that various modifications and changes can be made to these embodiments without departing from the broader spirit and scope of the present disclosure. Accordingly, the specification and drawings are to be regarded in an illustrative rather than a restrictive sense. The accompanying drawings that form a part of this application show, by way of illustration, and not of limitation, specific embodiments in which the subject matter can be practiced. The embodiments illustrated are described in sufficient detail to enable those skilled in the art to practice the teachings disclosed herein. Other embodiments can be used or derived therefrom, such that structural and logical substitutions and changes can be made without departing from the scope of this disclosure. This Detailed Description, therefore, is not to be taken in a limiting sense, and the scope of various embodiments is defined only by the appended claims, along with the full range of equivalents to which such claims are entitled. Specific embodiments or examples are illustrated and described herein, however, it should be appreciated that any arrangement calculated to achieve the same purpose can be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The above detailed description includes references to the accompanying drawings, which form a part of the detailed description. The drawings show, by way of illustration, specific embodiments in which methods, apparatuses, and systems discussed herein can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 kHz" includes "10 kHz." Terms or phrases preceded by a term such as "substantially" or "generally" include the recited term or phrase. For example, "substantially parallel" includes "parallel" and "generally cylindrical" includes cylindrical.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention(s) and embodiments should be determined with reference to the appended claims, along with the full scope of equivalents to which such claims are entitled.

What is claimed is:

1. A garment for receiving and positioning an external transmitter device proximal to an implanted device that is configured to provide a stimulation therapy at or near a neural target in a pelvic region of a patient, wherein the external transmitter device includes source structures that are configured to be excitable to generate a propagating and focused field in body tissue to communicate power or data to the implanted device, the garment comprising:
   a garment body comprising a flexible material configured to be worn by a user;
   a first receptacle comprising a portion of the garment body and configured to receive and position the external transmitter device near a tissue interface when the garment is worn by the user; and
   a dielectric member provided between the first receptacle and the tissue interface and configured to increase efficiency of wireless energy communications from the external transmitter device, through the dielectric member and body tissue, to the implanted device, wherein the dielectric member has a first relative permittivity that is approximately the same as the relative permittivity of air and the first relative permittivity is different from a relative permittivity of the tissue at the tissue interface, and the first relative permittivity is different from a relative permittivity of the garment body.

2. The garment of claim 1, wherein the dielectric member comprises a compressible polychloroprene rubber having a relative permittivity that is approximately the same as the relative permittivity of air when the polychloroprene rubber is compressed and when the polychloroprene rubber is uncompressed.

3. The garment of claim 1, wherein the dielectric member is dimensioned to separate the first receptacle from the tissue interface by at least a specified minimum separation distance, the specified minimum separation distance selected to (1) avoid exceeding a defined maximum loading on a transmission antenna of the external transmitter device and/or to (2) reduce a rate at which electromagnetic energy is absorbed by patient tissue at or near the tissue interface.

4. The garment of claim 1, wherein the dielectric member is configured to inhibit heat transfer from the first receptacle to the tissue interface.

5. The garment of claim 1, wherein the garment body comprises an elastic waistband coupled to the first receptacle, and the waistband is configured to position the first receptacle at or near an S3 foramen when the garment is worn by the user.

6. A garment for receiving and positioning an external transmitter device proximal to an implanted device that is configured to provide a stimulation therapy at or near a neural target in a pelvic region of the patient, wherein the external transmitter device includes one or more source structures on a source substrate and the source structures are configured to be excitable to generate a propagating field in body tissue and thereby communicate power or data signals to the implanted device, the garment comprising:
   a garment body comprising a flexible material, wherein the flexible material has a first relative permittivity characteristic;
   a first receptacle coupled with or comprising a portion of the garment body and configured to receive and position the external transmitter device near a tissue interface when the garment is worn by a user; and
   a dielectric member provided between the first receptacle and the tissue interface, wherein the dielectric member has a second relative permittivity characteristic that is approximately the same as the relative permittivity of air and is different from the first relative permittivity characteristic of the flexible material, and the second relative permittivity characteristic is different from a permittivity of the source substrate, and wherein the second relative permittivity characteristic is different from a relative permittivity of the tissue at the tissue interface.

7. The garment of claim 6, wherein the dielectric member comprises a compressible material having a relative permittivity that is approximately the same as the relative permittivity of air when the material is compressed and when the material is uncompressed.

8. The garment of claim 6, further comprising a second receptacle adjacent to the first receptacle and configured to receive the dielectric member.

9. The garment of claim 6, wherein the dielectric member is dimensioned to separate the first receptacle from the tissue interface by at least a specified minimum separation distance, the specified minimum separation distance selected to avoid exceeding a defined maximum loading on a transmission antenna of the external transmitter device.

10. The garment of claim 6, wherein the dielectric member is dimensioned to separate the first receptacle from the tissue interface by at least a specified minimum separation distance, the specified minimum separation distance selected to reduce a rate at which electromagnetic energy is absorbed by patient tissue at or near the tissue interface.

11. The garment of claim 6, wherein the dielectric member is configured to inhibit heat transfer from the first receptacle to the tissue interface.

12. The garment of claim 6, wherein the first receptacle includes at least a first wall provided adjacent to the dielectric member, and wherein the first wall and the dielectric member have different relative permittivity characteristics.

13. The garment of claim 6, wherein the garment body comprises an elastic waistband configured to position the first receptacle at or near an S3 foramen when the garment is worn by the user.

14. The garment of claim 6, further comprising a verification device, wherein the verification device communicates with the external transmitter device to enable one or more functions of the external transmitter device.

15. A method for controlling delivery of neural stimulation therapy using a system that includes an implanted midfield device and external midfield transmitter device, wherein the external midfield transmitter device includes one or more source structures on a source substrate that are configured to be excitable to manipulate evanescent fields outside of tissue to generate a propagating and focused field in the tissue and thereby communicate power and/or data signals to the implanted midfield device, wherein the implanted midfield device includes one or more electrodes for delivering an electrostimulation therapy to a neural target, the delivered therapy using energy received from the external midfield transmitter device, the method comprising:
   positioning the external midfield transmitter device at or near a tissue interface and the implanted midfield device using a garment that includes a garment body comprising a flexible material configured to be worn by a user, a receptacle comprising a portion of the garment body and configured to receive and position the external midfield transmitter device near the tissue interface when the garment is worn, and a dielectric member provided between the first receptacle and the tissue interface to electrically decouple contents of the first receptacle from tissue at the tissue interface, wherein the dielectric member has a first relative permittivity that is approximately the same as the relative permittivity of air and is different from a relative permittivity of the tissue at the tissue interface and is different from a relative permittivity of the flexible material and is different from a permittivity of the source substrate of the external midfield transmitter device;

using energy received from the external midfield transmitter device, providing a stimulation therapy at or near a neural target in a pelvic region of a patient using the implanted midfield device;

determining, using a control circuit, whether a voiding event is, or is likely to be, imminent or occurring for the patient; and enhancing voiding efficiency for the patient, including inhibiting or ceasing the stimulation therapy provided to the neural target when the voiding event is determined to be, or is determined likely to be, imminent or occurring for the patient.

16. The method of claim 15, wherein the determining whether the voiding event is, or is likely to be, imminent or occurring for the patient includes using the control circuit to determine a void interval for the patient based on information from one or more sensors configured to determine a fullness characteristic about the patient's bladder.

17. The method of claim 15, wherein the determining whether the voiding event is, or is likely to be, imminent or occurring for the patient includes using the control circuit to identify noncommunication between the external midfield transmitter device and the implanted midfield device.

18. The method of claim 15, wherein the determining whether the voiding event is, or is likely to be, imminent or occurring for the patient includes using a control circuit provided in one or both of the implanted midfield device and the external midfield transmitter device.

19. The method of claim 18, wherein the determining whether the voiding event is, or is likely to be, imminent or occurring for the patient includes using information from a position sensor coupled to the external midfield transmitter device, wherein the position sensor is configured to determine when the external midfield transmitter device moves away from the tissue interface.

20. The method of claim 18, wherein the control circuit is provided in the implanted midfield device, and wherein determining whether the voiding event is, or is likely to be, imminent or occurring for the patient includes using information from the implanted midfield device about whether it is receiving a substantially continuous power signal from the external midfield transmitter device.

* * * * *